United States Patent
Mounce et al.

(10) Patent No.: US 11,020,537 B2
(45) Date of Patent: *Jun. 1, 2021

(54) DRUG CASSETTE, AUTOINJECTOR, AND AUTOINJECTOR SYSTEM

(71) Applicant: AMGEN INC., Thousand Oaks, CA (US)

(72) Inventors: R. Paul Mounce, Burbank, CA (US); Clinton Judd, Oxnard, CA (US); Suhas Krishna, Simi Valley, CA (US); Neal Johnston, Dallas, TX (US); Gordon Johnston, Dallas, TX (US); Giorgio Sardo, Milan (IT); Gabriele Ganzitti, Milan (IT); Hong Jun Yeh, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,925

(22) Filed: Oct. 13, 2017

(65) Prior Publication Data

US 2018/0133106 A1    May 17, 2018

Related U.S. Application Data

(63) Continuation of application No. 14/777,255, filed as application No. PCT/US2014/027950 on Mar. 14, 2014.

(Continued)

(51) Int. Cl.
*A61M 5/32*    (2006.01)
*A61M 5/24*    (2006.01)
(Continued)

(52) U.S. Cl.
CPC ............ *A61M 5/3271* (2013.01); *A61M 5/20* (2013.01); *A61M 5/24* (2013.01); *A61M 5/3202* (2013.01);
(Continued)

(58) Field of Classification Search
CPC .... A61M 5/20; A61M 5/3202; A61M 5/3271; A61M 5/24; A61M 2005/2414;
(Continued)

(56) References Cited

U.S. PATENT DOCUMENTS 2,525,398 A    10/1950    Collins
2,565,081 A    8/1951    Maynes
(Continued)

FOREIGN PATENT DOCUMENTS

AU    2009249027 B2    8/2014
CA    2074565 A1    1/1993
(Continued)

OTHER PUBLICATIONS

Australian Patent Application No. 2009249027, Notice of Acceptance, dated Aug. 7, 2014.
(Continued)

*Primary Examiner* — Theodore J Stigell
(74) *Attorney, Agent, or Firm* — Marshall, Gerstein & Borun LLP

(57) ABSTRACT

A cassette for use with an injector has a housing, and a cassette identification arrangement (cassette ID) defining a code containing information about the cassette that is detectable and decipherable by an injector. The cassette may further have a sleeve movably disposed within the housing, for holding a drug container, and a locking arrangement for interlocking the sleeve with the housing. The cassette may further have an aperture in the housing, and a cassette cap for removing a needle shield of the drug container. The cassette
(Continued)

may have an anti-bending structure to prevent bending or flexing of the cassette cap. The injector may have a processor for controlling operational parameters of the injector and a detector communicatively coupled with the processor for detesting and communicating the cassette ID to the microprocessor to decipher the code defined therein. Also, a method of injecting a drug into a patient with an injector, wherein the sequence of actions performed by the user are controlled. Still further, a method of treating a patient in need thereof wherein a cassette containing a drug is provided and administered to the patient using an injector.

21 Claims, 32 Drawing Sheets

Related U.S. Application Data

(60) Provisional application No. 61/800,000, filed on Mar. 15, 2013.

(51) Int. Cl.
*A61M 5/20* (2006.01)
*A61M 5/48* (2006.01)
*A61J 1/18* (2006.01)
*A61M 5/42* (2006.01)
*A61M 5/46* (2006.01)
*G09B 23/28* (2006.01)

(52) U.S. Cl.
CPC .............. *A61J 1/18* (2013.01); *A61J 2205/60* (2013.01); *A61M 5/3204* (2013.01); *A61M 5/427* (2013.01); *A61M 5/46* (2013.01); *A61M 5/482* (2013.01); *A61M 2005/206* (2013.01); *A61M 2005/208* (2013.01); *A61M 2005/2407* (2013.01); *A61M 2005/2414* (2013.01); *A61M 2005/2481* (2013.01); *A61M 2005/2496* (2013.01); *A61M 2005/3247* (2013.01); *A61M 2205/14* (2013.01); *A61M 2205/192* (2013.01); *A61M 2205/50* (2013.01); *A61M 2205/581* (2013.01); *A61M 2205/6018* (2013.01); *A61M 2205/6027* (2013.01); *A61M 2205/6036* (2013.01); *A61M 2205/6054* (2013.01); *A61M 2205/6063* (2013.01); *A61M 2205/6072* (2013.01); *A61M 2205/6081* (2013.01); *G09B 23/285* (2013.01)

(58) Field of Classification Search
CPC .......... A61M 5/427; A61M 2005/2481; A61M 5/3204; A61M 5/482; A61M 2005/206; A61M 2005/2496; A61M 2005/3247; A61M 2205/6063; A61M 5/46; A61M 2005/208; A61M 2005/2407; A61J 1/18; A61J 2205/60
See application file for complete search history.

(56) References Cited

U.S. PATENT DOCUMENTS

| | | | |
|---|---|---|---|
| 2,701,566 A | 2/1955 | Krug | |
| 2,702,547 A | 2/1955 | Glass | |
| 3,051,173 A | 8/1962 | Johnson et al. | |
| 3,064,650 A | 11/1962 | Lewis | |
| 3,203,269 A | 8/1965 | Perrine | |
| 3,212,685 A | 10/1965 | James et al. | |
| 3,623,474 A | 11/1971 | Heilman et al. | |
| 3,720,211 A | 3/1973 | Kyrias | |
| 3,859,996 A | 1/1975 | Mizzy et al. | |
| 3,964,481 A | 6/1976 | Gourlandt et al. | |
| 4,108,177 A | 8/1978 | Pistor | |
| 4,231,368 A | 11/1980 | Becker | |
| 4,273,122 A | 6/1981 | Whitney et al. | |
| 4,276,879 A | 7/1981 | Yiournas | |
| 4,373,526 A | 2/1983 | Kling | |
| 4,421,107 A | 12/1983 | Estes et al. | |
| 4,465,478 A | 8/1984 | Sabelman et al. | |
| 4,493,704 A | 1/1985 | Beard et al. | |
| 4,502,488 A | 3/1985 | Degironimo et al. | |
| 4,504,263 A | 3/1985 | Steuer et al. | |
| 4,515,590 A | 5/1985 | Daniel | |
| 4,573,975 A | 3/1986 | Frist et al. | |
| 4,585,439 A | 4/1986 | Michel | |
| 4,613,328 A | 9/1986 | Boyd | |
| 4,617,016 A | 10/1986 | Blomberg | |
| 4,636,201 A | 1/1987 | Ambrose et al. | |
| 4,685,903 A | 8/1987 | Cable et al. | |
| 4,758,227 A | 7/1988 | Lancaster, Jr. et al. | |
| 4,787,893 A | 11/1988 | Villette | |
| 4,790,823 A | 12/1988 | Charton et al. | |
| 4,838,857 A | 6/1989 | Strowe et al. | |
| 4,877,034 A | 10/1989 | Atkins et al. | |
| 4,902,279 A | 2/1990 | Schmidtz et al. | |
| 4,919,596 A | 4/1990 | Slate et al. | |
| 4,986,818 A | 1/1991 | Imbert et al. | |
| 5,013,299 A | 5/1991 | Clark | |
| 5,024,616 A | 6/1991 | Ogle, II | |
| 5,034,003 A | 7/1991 | Denance | |
| 5,080,104 A | 1/1992 | Marks et al. | |
| 5,085,641 A | 2/1992 | Sarnoff et al. | |
| 5,092,843 A | 3/1992 | Monroe et al. | |
| 5,098,400 A | 3/1992 | Crouse et al. | |
| 5,112,317 A | 5/1992 | Michel | |
| 5,114,404 A | 5/1992 | Paxton et al. | |
| 5,114,406 A | 5/1992 | Gabriel et al. | |
| 5,176,643 A | 1/1993 | Kramer et al. | |
| 5,180,371 A | 1/1993 | Spinello | |
| 5,200,604 A | 4/1993 | Rudko et al. | |
| 5,221,268 A | 6/1993 | Barton et al. | |
| 5,271,413 A | 12/1993 | Dalamagas et al. | |
| 5,300,029 A | 4/1994 | Denance | |
| 5,318,522 A | 6/1994 | D'Antonio | |
| 5,352,196 A | 10/1994 | Haber et al. | |
| 5,354,286 A | 10/1994 | Mesa et al. | |
| 5,354,287 A | 10/1994 | Wacks | |
| 5,382,785 A | 1/1995 | Rink | |
| 5,393,497 A | 2/1995 | Haber et al. | |
| 5,425,715 A | 6/1995 | Dalling et al. | |
| 5,431,627 A | 7/1995 | Pastrone et al. | |
| 5,451,210 A | 9/1995 | Kramer et al. | |
| 5,456,670 A | 10/1995 | Neer et al. | |
| 5,458,263 A | 10/1995 | Ciammitti et al. | |
| 5,478,316 A | 12/1995 | Bitdinger et al. | |
| 5,540,664 A | 7/1996 | Wyrick | |
| 5,569,190 A | 10/1996 | D'Antonio | |
| 5,569,197 A | 10/1996 | Helmus et al. | |
| 5,569,212 A | 10/1996 | Brown | |
| 5,578,014 A | 11/1996 | Erez et al. | |
| 5,584,815 A | 12/1996 | Pawelka et al. | |
| 5,593,390 A | 1/1997 | Castellano et al. | |
| 5,599,302 A | 2/1997 | Lilley et al. | |
| 5,616,132 A | 4/1997 | Newman | |
| 5,647,851 A | 7/1997 | Pokras | |
| 5,647,853 A | 7/1997 | Feldmann et al. | |
| 5,665,071 A | 9/1997 | Wyrick | |
| 5,681,291 A | 10/1997 | Galli | |
| 5,690,618 A | 11/1997 | Smith et al. | |
| 5,695,472 A | 12/1997 | Wyrick | |
| 5,698,189 A | 12/1997 | Rowe et al. | |
| 5,709,662 A | 1/1998 | Olive et al. | |
| 5,720,729 A | 2/1998 | Kriesel | |
| 5,728,074 A | 3/1998 | Castellano et al. | |
| 5,746,714 A | 5/1998 | Salo et al. | |
| 5,779,683 A * | 7/1998 | Meyer | A61M 5/2429 604/110 |
| 5,807,346 A | 9/1998 | Frezza | |
| 5,843,036 A | 12/1998 | Olive et al. | |
| 5,868,711 A | 2/1999 | Kramer et al. | |
| 5,911,703 A | 6/1999 | Slate et al. | |

(56) References Cited

U.S. PATENT DOCUMENTS

| | | |
|---|---|---|
| 5,919,159 A | 7/1999 | Lilley et al. |
| 5,921,963 A | 7/1999 | Erez et al. |
| 5,921,966 A | 7/1999 | Bendek et al. |
| 5,928,158 A | 7/1999 | Aristides |
| 5,945,046 A | 8/1999 | Hehl et al. |
| 5,957,897 A | 9/1999 | Jeffrey |
| 5,968,063 A | 10/1999 | Chu et al. |
| 5,993,423 A | 11/1999 | Choi |
| 6,019,745 A | 2/2000 | Gray |
| 6,019,747 A | 2/2000 | McPhee |
| 6,051,896 A | 4/2000 | Shibuya et al. |
| 6,090,082 A | 7/2000 | King et al. |
| 6,099,503 A | 8/2000 | Stradella |
| 6,104,941 A | 8/2000 | Huey et al. |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,190,361 B1 | 2/2001 | Gettig et al. |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,241,709 B1 | 6/2001 | Bechtold et al. |
| 6,245,043 B1 | 6/2001 | Villette |
| 6,248,093 B1 | 6/2001 | Moberg |
| 6,270,479 B1 | 8/2001 | Bergens et al. |
| 6,270,481 B1 | 8/2001 | Mason et al. |
| 6,280,421 B1 | 8/2001 | Kirchhofer et al. |
| 6,290,683 B1 | 9/2001 | Erez et al. |
| 6,344,030 B1 | 2/2002 | Duchon et al. |
| 6,344,032 B1 | 2/2002 | Perez et al. |
| 6,371,939 B2 | 4/2002 | Bergens et al. |
| 6,387,078 B1 | 5/2002 | Gillespie, III |
| 6,406,456 B1 | 6/2002 | Slate et al. |
| 6,447,482 B1 | 9/2002 | Ronborg et al. |
| 6,454,743 B1 | 9/2002 | Weber |
| 6,503,454 B1 | 1/2003 | Hadimioglu et al. |
| 6,520,928 B1 | 2/2003 | Junior |
| 6,540,672 B1 | 4/2003 | Simonsen et al. |
| 6,544,234 B1 | 4/2003 | Gabriel |
| 6,547,755 B1 | 4/2003 | Lippe et al. |
| 6,562,006 B1 | 5/2003 | Hjertman et al. |
| 6,569,123 B2 | 5/2003 | Alchas et al. |
| 6,569,127 B1 | 5/2003 | Fago et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Slate et al. |
| D483,116 S | 12/2003 | Castellano |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,743,202 B2 | 6/2004 | Hirschman et al. |
| 6,746,427 B2 | 6/2004 | Duchon et al. |
| 6,752,787 B1 | 6/2004 | Causey, III et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,817,986 B2 | 11/2004 | Slate et al. |
| 6,835,193 B2 | 12/2004 | Epstein et al. |
| 6,854,620 B2 | 2/2005 | Ramey |
| 6,890,319 B1 | 5/2005 | Crocker |
| 6,932,793 B1 | 8/2005 | Marshall et al. |
| 6,979,316 B1 | 12/2005 | Rubin et al. |
| 6,986,760 B2 | 1/2006 | Giambattista et al. |
| 7,008,399 B2 | 3/2006 | Larsen et al. |
| 7,011,649 B2 | 3/2006 | De La Serna et al. |
| 7,025,774 B2 | 4/2006 | Freeman et al. |
| 7,041,085 B2 | 5/2006 | Perez et al. |
| 7,066,909 B1 | 6/2006 | Peter et al. |
| 7,094,230 B2 | 8/2006 | Flaherty et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,291,132 B2 | 11/2007 | Deruntz et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,390,319 B2 | 6/2008 | Friedman |
| 7,442,185 B2 | 10/2008 | Amark et al. |
| 7,449,012 B2 | 11/2008 | Young et al. |
| 7,476,217 B2 | 1/2009 | Martin et al. |
| 7,500,963 B2 | 3/2009 | Westbye et al. |
| 7,500,966 B2 | 3/2009 | Hommann |
| 7,553,294 B2 | 6/2009 | Lazzaro et al. |
| 7,597,685 B2 | 10/2009 | Olson |
| 7,635,348 B2 | 12/2009 | Raven et al. |
| 7,635,350 B2 | 12/2009 | Scherer |
| 7,648,483 B2 | 1/2010 | Edwards et al. |
| 7,654,987 B2 | 2/2010 | Hommann et al. |
| 7,670,314 B2 | 3/2010 | Wall et al. |
| 7,686,789 B2 | 3/2010 | Nemoto et al. |
| 7,731,686 B2 | 6/2010 | Edwards et al. |
| D619,706 S | 7/2010 | Schon et al. |
| 7,749,195 B2 | 7/2010 | Hommann |
| 7,760,099 B2 | 7/2010 | Knight |
| 7,785,292 B2 | 8/2010 | Harrison |
| D625,015 S | 10/2010 | Hansen et al. |
| 7,828,776 B2 | 11/2010 | Nemoto et al. |
| D628,690 S | 12/2010 | Galbraith |
| 7,857,791 B2 | 12/2010 | Jacobs et al. |
| 7,887,513 B2 | 2/2011 | Nemoto et al. |
| 7,901,377 B1 | 3/2011 | Harrison et al. |
| 7,909,796 B2 | 3/2011 | Weber |
| 7,918,823 B2 | 4/2011 | Edwards et al. |
| 7,922,695 B2 | 4/2011 | Wiegel et al. |
| D637,713 S | 5/2011 | Nord et al. |
| 7,938,803 B2 | 5/2011 | Mernoe et al. |
| D642,261 S | 7/2011 | York et al. |
| 7,976,499 B2 | 7/2011 | Grunhut et al. |
| 8,012,120 B2 | 9/2011 | Slate et al. |
| 8,012,125 B1 | 9/2011 | Fago et al. |
| 8,016,797 B2 | 9/2011 | Gratwohl et al. |
| 8,043,262 B2 | 10/2011 | Streit et al. |
| 8,048,037 B2 | 11/2011 | Kohlbrenner et al. |
| 8,052,645 B2 | 11/2011 | Slate et al. |
| D650,070 S | 12/2011 | Mori |
| 8,088,096 B2 | 1/2012 | Lauchard et al. |
| 8,105,271 B2 | 1/2012 | Matusch |
| 8,141,417 B2 | 3/2012 | Gibson et al. |
| 8,152,779 B2 | 4/2012 | Cabiri |
| 8,177,749 B2 | 5/2012 | Slate et al. |
| 8,221,356 B2 | 7/2012 | Enggaard et al. |
| 8,226,610 B2 * | 7/2012 | Edwards ............... A61M 5/19 604/137 |
| 8,277,414 B2 | 10/2012 | Barrow-Williams et al. |
| 8,298,171 B2 | 10/2012 | Ishikawa et al. |
| 8,308,687 B2 | 11/2012 | Carrel et al. |
| 8,337,472 B2 | 12/2012 | Edginton et al. |
| D673,677 S | 1/2013 | Noda et al. |
| 8,343,103 B2 | 1/2013 | Moser |
| 8,376,985 B2 | 2/2013 | Pongpairochana et al. |
| D679,008 S | 3/2013 | Schroeder et al. |
| D679,391 S | 4/2013 | Chinowsky et al. |
| 8,491,538 B2 | 7/2013 | Kohlbrenner et al. |
| 8,523,803 B1 | 9/2013 | Favreau |
| 8,591,465 B2 | 11/2013 | Hommann |
| D694,879 S | 12/2013 | Julian et al. |
| 8,603,026 B2 | 12/2013 | Favreau |
| 8,603,027 B2 | 12/2013 | Favreau |
| 8,609,621 B2 | 12/2013 | Bedzyk et al. |
| 8,628,723 B2 | 1/2014 | Vandergaw |

(56) References Cited

U.S. PATENT DOCUMENTS

| | | |
|---|---|---|
| D702,343 S | 4/2014 | Dale et al. |
| D702,835 S | 4/2014 | Vinchon |
| 8,690,827 B2 | 4/2014 | Edwards et al. |
| 8,696,628 B2 | 4/2014 | Grunhut |
| 8,716,711 B2 | 5/2014 | Iwasaki |
| D718,439 S | 11/2014 | Woehr et al. |
| 8,900,204 B2 | 12/2014 | Geertsen |
| 8,911,410 B2 | 12/2014 | Ekman et al. |
| 8,960,827 B2 | 2/2015 | McMillin et al. |
| 8,961,473 B2 | 2/2015 | Heald |
| 8,968,255 B2 | 3/2015 | Oakland |
| 9,011,386 B2 | 4/2015 | Kronestedt et al. |
| 9,138,542 B2 | 9/2015 | Smith |
| D748,783 S | 2/2016 | Zhang et al. |
| 9,278,177 B2 | 3/2016 | Edwards et al. |
| D757,254 S | 5/2016 | Wohlfahrt et al. |
| D765,241 S | 8/2016 | Holland |
| D768,851 S | 10/2016 | Rozwadowski et al. |
| D768,852 S | 10/2016 | Rozwadowski et al. |
| 9,616,173 B2 | 4/2017 | Slate et al. |
| 9,649,443 B2 | 5/2017 | Klintenstedt et al. |
| 9,925,336 B2 | 3/2018 | Slate et al. |
| 9,974,904 B2 | 5/2018 | Burk et al. |
| 10,092,703 B2 * | 10/2018 | Mounce ............... A61M 5/20 |
| 10,092,706 B2 | 10/2018 | Denzer et al. |
| 2001/0005781 A1 | 6/2001 | Bergens et al. |
| 2001/0011163 A1 | 8/2001 | Nolan et al. |
| 2001/0018937 A1 | 9/2001 | Nemoto |
| 2001/0034502 A1 | 10/2001 | Moberg et al. |
| 2001/0047153 A1 | 11/2001 | Trocki et al. |
| 2002/0016569 A1 | 2/2002 | Critchlow et al. |
| 2002/0022066 A1 | 2/2002 | Matsubayashi et al. |
| 2002/0029018 A1 | 3/2002 | Jeffrey |
| 2002/0095120 A1 | 7/2002 | Larsen et al. |
| 2002/0099334 A1 | 7/2002 | Hanson et al. |
| 2002/0133113 A1 | 9/2002 | Madsen et al. |
| 2002/0151855 A1 | 10/2002 | Douglas et al. |
| 2002/0156426 A1 | 10/2002 | Gagnieux et al. |
| 2003/0036725 A1 | 2/2003 | Lavi et al. |
| 2003/0050592 A1 | 3/2003 | Slate et al. |
| 2003/0065536 A1 | 4/2003 | Hansen et al. |
| 2003/0105430 A1 | 6/2003 | Lavi et al. |
| 2003/0236502 A1 | 12/2003 | De La Serna et al. |
| 2004/0019326 A1 | 1/2004 | Gilbert et al. |
| 2004/0039336 A1 | 2/2004 | Amark et al. |
| 2004/0054327 A1 | 3/2004 | Gillespie |
| 2004/0068266 A1 | 4/2004 | Delmotte |
| 2004/0116861 A1 | 6/2004 | Trocki et al. |
| 2004/0129803 A1 | 7/2004 | Dolder et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0208845 A1 | 10/2004 | Michal et al. |
| 2004/0225262 A1 | 11/2004 | Fathallah et al. |
| 2004/0258756 A1 | 12/2004 | McLoughlin |
| 2005/0020979 A1 | 1/2005 | Westbye et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0148869 A1 | 7/2005 | Masuda |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0197650 A1 | 9/2005 | Sugimoto et al. |
| 2005/0203466 A1 | 9/2005 | Hommann et al. |
| 2005/0209569 A1 | 9/2005 | Ishikawa et al. |
| 2005/0261693 A1 | 11/2005 | Miller et al. |
| 2005/0277885 A1 | 12/2005 | Scherer |
| 2006/0022363 A1 | 2/2006 | Konno et al. |
| 2006/0030819 A1 | 2/2006 | Young et al. |
| 2006/0157064 A1 | 7/2006 | Davison et al. |
| 2006/0173408 A1 | 8/2006 | Wyrick |
| 2006/0251646 A1 | 11/2006 | Utku |
| 2006/0270985 A1 | 11/2006 | Hommann et al. |
| 2007/0021720 A1 | 1/2007 | Guillermo |
| 2007/0025879 A1 | 2/2007 | Vandergaw |
| 2007/0027430 A1 | 2/2007 | Hommann |
| 2007/0066938 A1 | 3/2007 | Iio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0167920 A1 | 7/2007 | Hommann |
| 2007/0173770 A1 | 7/2007 | Stamp |
| 2007/0197954 A1 | 8/2007 | Keenan |
| 2007/0197968 A1 | 8/2007 | Pongpairochana et al. |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0250010 A1 | 10/2007 | Hohlfelder et al. |
| 2007/0265568 A1 | 11/2007 | Tsals et al. |
| 2008/0015510 A1 | 1/2008 | Sandoz et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0097325 A1 | 4/2008 | Tanaka et al. |
| 2008/0132841 A1 | 6/2008 | Chiwanga et al. |
| 2008/0140007 A1 | 6/2008 | Glynn |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podaima |
| 2009/0076383 A1 | 3/2009 | Toews et al. |
| 2009/0149744 A1 | 6/2009 | Nemoto et al. |
| 2009/0254060 A1 | 10/2009 | Hetherington |
| 2009/0270672 A1 | 10/2009 | Fago |
| 2009/0281505 A1 | 11/2009 | Hansen et al. |
| 2009/0292246 A1 | 11/2009 | Slate et al. |
| 2009/0299288 A1 | 12/2009 | Sie et al. |
| 2009/0299290 A1 | 12/2009 | Moberg |
| 2009/0312705 A1 | 12/2009 | Grunhut et al. |
| 2009/0322545 A1 | 12/2009 | Gibson et al. |
| 2009/0326459 A1 | 12/2009 | Shipway et al. |
| 2010/0016793 A1 | 1/2010 | Jennings et al. |
| 2010/0016795 A1 | 1/2010 | McLoughlin |
| 2010/0021456 A1 | 1/2010 | Miossec et al. |
| 2010/0022955 A1 | 1/2010 | Slate et al. |
| 2010/0036318 A1 | 2/2010 | Raday et al. |
| 2010/0042054 A1 | 2/2010 | Elahi et al. |
| 2010/0112679 A1 | 5/2010 | Vandergaw |
| 2010/0152655 A1 | 6/2010 | Stamp |
| 2010/0152659 A1 | 6/2010 | Streit et al. |
| 2010/0160894 A1 | 6/2010 | Julian et al. |
| 2010/0198060 A1 | 8/2010 | Fago et al. |
| 2010/0268170 A1 | 10/2010 | Carrel et al. |
| 2010/0312195 A1 | 12/2010 | Johansen et al. |
| 2011/0004165 A1 | 1/2011 | Iio et al. |
| 2011/0023281 A1 | 2/2011 | Schraga |
| 2011/0044998 A1 | 2/2011 | Bedian et al. |
| 2011/0047153 A1 | 2/2011 | Betz |
| 2011/0092915 A1 | 4/2011 | Olson et al. |
| 2011/0097229 A1 | 4/2011 | Cauley, III et al. |
| 2011/0098655 A1 | 4/2011 | Jennings et al. |
| 2011/0137286 A1 | 6/2011 | Mudd et al. |
| 2011/0144594 A1 | 6/2011 | Sund et al. |
| 2011/0152781 A1 | 6/2011 | Brunnberg et al. |
| 2011/0160580 A1 | 6/2011 | Perkins et al. |
| 2011/0166512 A1 | 7/2011 | Both et al. |
| 2011/0184383 A1 | 7/2011 | Hasegawa |
| 2011/0190693 A1 | 8/2011 | Takatsuka et al. |
| 2011/0190702 A1 | 8/2011 | Stumber |
| 2011/0196339 A1 | 8/2011 | Hirschel et al. |
| 2011/0202011 A1 | 8/2011 | Wozencroft |
| 2011/0213315 A1 | 9/2011 | Sweeney et al. |
| 2011/0224616 A1 | 9/2011 | Slate et al. |
| 2011/0224620 A1 | 9/2011 | Johansen et al. |

(56) References Cited

U.S. PATENT DOCUMENTS

| | | |
|---|---|---|
| 2011/0224621 A1 | 9/2011 | Johansen et al. |
| 2011/0230833 A1 | 9/2011 | Landman et al. |
| 2011/0245761 A1 | 10/2011 | Jennings et al. |
| 2011/0257596 A1 | 10/2011 | Gaudet |
| 2011/0257604 A1 | 10/2011 | Banik |
| 2011/0264046 A1 | 10/2011 | Nyholm et al. |
| 2011/0270220 A1 | 11/2011 | Genosar |
| 2012/0035472 A1 | 2/2012 | Bruce et al. |
| 2012/0035538 A1 | 2/2012 | Elmen et al. |
| 2012/0056019 A1 | 3/2012 | Renz et al. |
| 2012/0059319 A1 | 3/2012 | Segal |
| 2012/0089119 A1 | 4/2012 | Slate et al. |
| 2012/0101439 A9* | 4/2012 | Slate ............... A61M 5/20 604/154 |
| 2012/0172815 A1 | 7/2012 | Holmqvist |
| 2012/0238961 A1 | 9/2012 | Julian et al. |
| 2012/0253314 A1 | 10/2012 | Harish et al. |
| 2012/0265142 A1 | 10/2012 | Slate et al. |
| 2012/0296286 A1 | 11/2012 | Raab et al. |
| 2012/0323176 A1 | 12/2012 | Watanabe et al. |
| 2013/0018313 A1* | 1/2013 | Kramer ............ A61M 5/2033 604/131 |
| 2013/0018315 A1 | 1/2013 | Blomquist |
| 2013/0030383 A1 | 1/2013 | Keitel |
| 2013/0035647 A1 | 2/2013 | Veasey et al. |
| 2013/0046248 A1 | 2/2013 | Raab |
| 2013/0110049 A1 | 5/2013 | Cronenberg et al. |
| 2013/0110054 A1 | 5/2013 | Raab et al. |
| 2013/0112521 A1 | 5/2013 | Ekman et al. |
| 2013/0131595 A1 | 5/2013 | Ekman et al. |
| 2013/0131601 A1 | 5/2013 | Pommereau et al. |
| 2013/0190719 A1 | 7/2013 | Smith et al. |
| 2013/0190721 A1 | 7/2013 | Kemp et al. |
| 2013/0204198 A1 | 8/2013 | Burnell et al. |
| 2013/0204204 A1 | 8/2013 | Butler et al. |
| 2013/0218092 A1 | 8/2013 | Davies et al. |
| 2013/0226091 A1 | 8/2013 | Nzike et al. |
| 2013/0261558 A1 | 10/2013 | Hourmand et al. |
| 2013/0274668 A1 | 10/2013 | Barrow-Williams et al. |
| 2013/0289491 A1 | 10/2013 | Kramer et al. |
| 2013/0310744 A1 | 11/2013 | Brereton et al. |
| 2013/0310761 A1 | 11/2013 | Plumptre |
| 2013/0317430 A1 | 11/2013 | Brereton et al. |
| 2013/0317480 A1 | 11/2013 | Reber et al. |
| 2013/0324935 A1 | 12/2013 | Brereton et al. |
| 2013/0338601 A1 | 12/2013 | Cowe |
| 2014/0046259 A1 | 2/2014 | Reber et al. |
| 2014/0148784 A1 | 5/2014 | Anderson et al. |
| 2014/0194854 A1 | 7/2014 | Tsals |
| 2014/0236087 A1 | 8/2014 | Alderete et al. |
| 2014/0257197 A1 | 9/2014 | Madsen et al. |
| 2014/0276448 A1 | 9/2014 | Muller-Pathle et al. |
| 2014/0296825 A1 | 10/2014 | Lemaire et al. |
| 2014/0303556 A1 | 10/2014 | Travanty |
| 2014/0316369 A1 | 10/2014 | Centeno et al. |
| 2014/0330203 A1 | 11/2014 | McLoughlin et al. |
| 2014/0330216 A1 | 11/2014 | Weaver et al. |
| 2014/0336590 A1 | 11/2014 | Hourmand et al. |
| 2014/0364808 A1 | 12/2014 | Niklaus et al. |
| 2015/0045729 A1 | 2/2015 | Denzer et al. |
| 2015/0080809 A1 | 3/2015 | Dasbach et al. |
| 2015/0136809 A1 | 5/2015 | Hamann et al. |
| 2015/0141923 A1 | 5/2015 | Wurmbauer et al. |
| 2015/0151046 A1 | 6/2015 | Nagel et al. |
| 2015/0165130 A1 | 6/2015 | Butler et al. |
| 2015/0217057 A1 | 8/2015 | Hogdahl |
| 2016/0022914 A1 | 1/2016 | Mounce et al. |
| 2016/0120751 A1 | 5/2016 | Mounce et al. |
| 2016/0271326 A1 | 9/2016 | Slate et al. |
| 2017/0043105 A1 | 2/2017 | Elmen |
| 2017/0157326 A1 | 6/2017 | Slate et al. |

FOREIGN PATENT DOCUMENTS

| | | |
|---|---|---|
| CA | 2594627 A1 | 8/2006 |
| DE | 102007061775 A1 | 7/2009 |
| EP | 1219312 A2 | 7/2002 |
| EP | 1227423 A1 | 7/2002 |
| EP | 1518575 A1 | 3/2005 |
| ES | 2121536 A1 | 11/1998 |
| FR | 2390175 A2 | 12/1978 |
| FR | 2581548 A1 | 11/1986 |
| FR | 2592307 A1 | 7/1987 |
| FR | 2622457 A1 | 5/1989 |
| FR | 2716375 A1 | 8/1995 |
| IL | 87559 A | 6/1993 |
| IL | 877559 | 6/1993 |
| JP | S63139563 A | 6/1988 |
| JP | 2008157 | 1/1990 |
| JP | H07503384 A | 4/1995 |
| JP | H07185000 A | 7/1995 |
| JP | H11-276583 A | 10/1999 |
| JP | 2000-237309 A | 9/2000 |
| JP | 2001518366 A | 10/2001 |
| JP | 20020531228 A | 9/2002 |
| JP | 2002543931 A | 12/2002 |
| JP | 2003-180828 A | 7/2003 |
| JP | 2003220142 A | 8/2003 |
| JP | 2005-131007 A | 5/2005 |
| JP | 2005514082 A | 5/2005 |
| JP | 2005-287676 A | 10/2005 |
| JP | 2006507061 A | 3/2006 |
| JP | 2006-523507 A | 10/2006 |
| JP | 2006528040 A | 12/2006 |
| JP | 2007500561 A | 1/2007 |
| JP | 2007-507260 A | 3/2007 |
| JP | 2007-127086 A | 5/2007 |
| JP | 2007111518 A | 5/2007 |
| JP | 2007529243 A | 10/2007 |
| JP | 2008508961 A | 3/2008 |
| JP | 2010-051828 A | 3/2010 |
| JP | 2010511414 A | 4/2010 |
| JP | 2015186876 A | 10/2015 |
| JP | 2017-023813 A | 2/2017 |
| TW | 200833383 A | 8/2008 |
| TW | 200833387 A | 8/2008 |
| TW | 200836787 A | 9/2008 |
| TW | 200840606 A | 10/2008 |
| TW | 201004667 A | 2/2010 |
| TW | 201004668 A | 2/2010 |
| WO | WO-1986006967 A1 | 12/1986 |
| WO | WO-1987003494 A1 | 6/1987 |
| WO | WO-1987007160 A1 | 12/1987 |
| WO | WO-1991018634 A1 | 12/1991 |
| WO | WO-1992006725 A1 | 4/1992 |
| WO | WO-1992008506 A1 | 5/1992 |
| WO | WO-1992021392 A1 | 12/1992 |
| WO | WO-1993002728 A1 | 2/1993 |
| WO | WO-1993013817 A1 | 7/1993 |
| WO | WO-1993024160 A1 | 12/1993 |
| WO | WO-1993025256 A1 | 12/1993 |
| WO | WO-1994006494 A1 | 3/1994 |
| WO | 94/07553 A1 | 4/1994 |
| WO | WO-1995021645 A1 | 8/1995 |
| WO | WO-1995025555 A1 | 9/1995 |
| WO | WO-1995031235 A1 | 11/1995 |
| WO | WO-1995034333 A2 | 12/1995 |
| WO | WO-1996000594 A1 | 1/1996 |
| WO | WO-1996021482 A2 | 7/1996 |
| WO | WO-1996026754 A2 | 9/1996 |
| WO | WO-1996038190 A1 | 12/1996 |
| WO | WO-1997007839 A1 | 3/1997 |
| WO | WO-1997031665 A1 | 9/1997 |
| WO | WO-1998013077 A2 | 4/1998 |
| WO | WO-1998017332 A2 | 4/1998 |
| WO | WO-1998021408 A1 | 5/1998 |
| WO | 98/28032 A1 | 7/1998 |
| WO | WO-99/17823 A1 | 4/1999 |
| WO | WO-1999017823 A1 | 4/1999 |
| WO | WO-1999020327 A2 | 4/1999 |
| WO | WO-1999021600 A2 | 5/1999 |

(56) References Cited

FOREIGN PATENT DOCUMENTS

| | | |
|---|---|---|
| WO | WO-99/65548 A1 | 12/1999 |
| WO | WO-2000002605 | 1/2000 |
| WO | WO-2000009186 A2 | 2/2000 |
| WO | WO-2000024441 | 5/2000 |
| WO | WO-2000025846 | 5/2000 |
| WO | WO-2001000261 | 1/2001 |
| WO | WO-2001037903 | 5/2001 |
| WO | WO-01/41835 A2 | 6/2001 |
| WO | WO-2001041835 | 6/2001 |
| WO | WO-01/089634 A2 | 11/2001 |
| WO | WO-2001089634 | 11/2001 |
| WO | WO-02/07812 A2 | 1/2002 |
| WO | WO-2002007812 | 1/2002 |
| WO | WO-2002/11792 A1 | 2/2002 |
| WO | WO-02/49691 A2 | 6/2002 |
| WO | WO-2002049691 | 6/2002 |
| WO | WO-2002/060513 A2 | 8/2002 |
| WO | WO-02/092153 A2 | 11/2002 |
| WO | WO-2002092153 | 11/2002 |
| WO | 03/03934 A1 | 1/2003 |
| WO | WO-03/006099 A1 | 1/2003 |
| WO | WO-03/008023 A1 | 1/2003 |
| WO | WO-2003006099 | 1/2003 |
| WO | WO-2003008023 | 1/2003 |
| WO | WO-2003/024385 A1 | 3/2003 |
| WO | WO-03/039634 A1 | 5/2003 |
| WO | WO-03/047663 A2 | 6/2003 |
| WO | WO-2003/047659 A1 | 6/2003 |
| WO | WO-2003047663 | 6/2003 |
| WO | WO-03/90509 A2 | 11/2003 |
| WO | WO-2003090509 | 11/2003 |
| WO | WO-03/103749 A2 | 12/2003 |
| WO | WO-2003103749 | 12/2003 |
| WO | WO-2004/004809 A1 | 1/2004 |
| WO | WO-2004/004825 A2 | 1/2004 |
| WO | WO-2004/069303 A2 | 8/2004 |
| WO | 2004/084795 A1 | 10/2004 |
| WO | WO-2004/108193 A1 | 12/2004 |
| WO | WO-2005/032449 A1 | 4/2005 |
| WO | WO-2005/053771 A2 | 6/2005 |
| WO | WO-2005/070481 A1 | 8/2005 |
| WO | WO-2005/079440 A2 | 9/2005 |
| WO | WO-2005089831 A1 | 9/2005 |
| WO | WO-2005/094923 A1 | 10/2005 |
| WO | WO-2006015501 A1 | 2/2006 |
| WO | WO-2006017732 A2 | 2/2006 |
| WO | WO-2006020609 A1 | 2/2006 |
| WO | WO-2006062788 A2 | 6/2006 |
| WO | WO-2006063015 A2 | 6/2006 |
| WO | WO-2006084821 A2 | 8/2006 |
| WO | WO-2006086774 A2 | 8/2006 |
| WO | WO-2007002053 A2 | 1/2007 |
| WO | WO-2007044980 A2 | 4/2007 |
| WO | WO-2007047200 A1 | 4/2007 |
| WO | WO-2007053779 A2 | 5/2007 |
| WO | WO-2007075677 A2 | 7/2007 |
| WO | WO-2007099044 A1 | 9/2007 |
| WO | WO-2007126851 A2 | 11/2007 |
| WO | WO-2007138299 A1 | 12/2007 |
| WO | WO-2007138313 A1 | 12/2007 |
| WO | WO-2007140610 A1 | 12/2007 |
| WO | WO-2008/004670 A1 | 1/2008 |
| WO | WO-2008021776 A2 | 2/2008 |
| WO | WO-2008024810 A2 | 2/2008 |
| WO | WO-2008048750 A2 | 4/2008 |
| WO | WO-2008064092 A2 | 5/2008 |
| WO | WO-2008075033 A1 | 6/2008 |
| WO | WO-2008083313 A2 | 7/2008 |
| WO | WO-2008093063 A2 | 8/2008 |
| WO | WO-2008094984 A2 | 8/2008 |
| WO | WO-2008095124 A1 | 8/2008 |
| WO | 2008/113772 A1 | 9/2008 |
| WO | WO-2008107670 A2 | 9/2008 |
| WO | WO-2008139458 A2 | 11/2008 |
| WO | WO-2008139460 A2 | 11/2008 |
| WO | WO-2008146021 A1 | 12/2008 |
| WO | WO-2009006725 A1 | 1/2009 |
| WO | WO-2009019437 A1 | 2/2009 |
| WO | WO-2009097325 | 8/2009 |
| WO | WO-2009125879 A1 | 10/2009 |
| WO | WO-2009143255 A1 | 11/2009 |
| WO | WO-2010023481 A1 | 3/2010 |
| WO | WO-2010026414 A1 | 3/2010 |
| WO | WO-2010076275 A1 | 7/2010 |
| WO | WO-2010091133 A2 | 8/2010 |
| WO | WO-2010/099850 A1 | 9/2010 |
| WO | WO-2010100213 A1 | 9/2010 |
| WO | WO-2010127449 A1 | 11/2010 |
| WO | WO-2011/014525 A2 | 2/2011 |
| WO | 2011/056888 A2 | 5/2011 |
| WO | WO-2011057065 A1 | 5/2011 |
| WO | 2011/089206 A2 | 7/2011 |
| WO | WO-2012000871 A1 | 1/2012 |
| WO | WO-2012000940 A2 | 1/2012 |
| WO | 2012/022771 A2 | 2/2012 |
| WO | 2012/080481 A | 6/2012 |
| WO | WO-2012/103140 A1 | 8/2012 |
| WO | WO-2012145685 A1 | 10/2012 |
| WO | WO-2012164389 A2 | 12/2012 |
| WO | WO-2012164394 A2 | 12/2012 |
| WO | WO-2012164397 A1 | 12/2012 |
| WO | WO-2013001378 A2 | 1/2013 |
| WO | WO-2013034984 A2 | 3/2013 |
| WO | WO-2013034986 A2 | 3/2013 |
| WO | WO-2013065055 A1 | 5/2013 |
| WO | WO-2014143815 A2 | 9/2014 |
| WO | WO-2014144096 A1 | 9/2014 |

OTHER PUBLICATIONS

Australian Patent Application No. 2009249027, Office Action, dated Jul. 24, 2013.
Australian Patent Application No. 2012245231, First Examination Report, dated Oct. 19, 2015.
Australian Patent Application No. 2012245231, Notice of Allowance, dated Oct. 4, 2016.
Australian Patent Application No. 2012245231, Office Action, dated Jul. 5, 2016.
Australian Patent Application No. 2014268139, Office Action, dated Jul. 19, 2016.
Australian Patent Application No. 2014268140, Office Action, dated Jul. 22, 2016.
Australian Patent Application No. 2014268140, Office Action, dated Sep. 2, 2016.
Australian Patent Application No. 2017200125, Examination Report No. 1, dated Sep. 18, 2017.
Canadian patent application No. 2724641, Examination Report, dated Dec. 15, 2016.
Canadian patent application No. 2724641, Examination Report, dated Sep. 29, 2017.
Canadian Patent Application No. 2724641, Office Action, dated Jun. 4, 2015.
Canadian patent application No. 2833748, Examination Report, dated Aug. 12, 2016.
Canadian patent application No. 2833748, Examination Report, dated May 2, 2017.
Canadian Patent Application No. 2833748, Office Action, dated Nov. 23, 2015.
European patent application No. 09751483.0, Extended Search Report, dated Aug. 1, 2013.
European Patent Application No. 09751483.0, Office Action, dated Apr. 10, 2015.
European patent application No. 09751483.0, Office Action, dated Aug. 1, 2016.
European Patent Application No. 09751483.0, Office Action, dated May 14, 2014.
European Patent Application No. 09751483.0, Office Action, dated Nov. 16, 2015.
European patent application No. 12774589.1, Extended Search Report, dated Feb. 23, 2015.

(56) References Cited

OTHER PUBLICATIONS

European Patent Application No. 12774589.1, Extended Search Report, dated Jul. 8, 2015.
European patent application No. 14763010.7, Extended Search Report and Opinion, dated Jan. 10, 2017.
European patent application No. 14763010.7, Partial Supplementary Search Report, dated Oct. 24, 2016.
European patent application No. 14765760.5, Extended Search Report, dated Jan. 11, 2017.
International Patent Application No. PCT/US2014/027950, International Preliminary Report on Patentability, dated Sep. 15, 2015.
International Patent Application No. PCT/US09/44693, International Preliminary Report on Patentability, dated Nov. 23, 2010.
International Patent Application No. PCT/US09/44693, International Search Report, dated Jul. 21, 2009.
International Patent Application No. PCT/US2012/034535, International Preliminary Report on Patentability, dated Oct. 22, 2013.
International Patent Application No. PCT/US2012/34535, International Search Report and Written Opinion, dated Aug. 17, 2012.
International Patent Application No. PCT/US2014/027950, International Search Report and Written Opinion, dated Oct. 7, 2014.
International Patent Application No. PCT/US2014/028363, International Preliminary Report on Patentability, dated Sep. 15, 2015.
International Patent Application No. PCT/US2014/028363, International Search Report and Written Opinion, dated Aug. 18, 2014.
Japanese Patent Application No. 2011-510683, Notice of Allowance, dated Oct. 5, 2015.
Japanese Patent Application No. 2011-510683, Office Action, dated Jul. 30, 2013.
Japanese Patent Application No. 2011-510683, Office Action, dated Jun. 30, 2014.
Japanese Patent Application No. 2014-021052, Final Office Action, dated Apr. 20, 2015.
Japanese Patent Application No. 2014-021052, Notice of Allowance, dated Aug. 24, 2015.
Japanese Patent Application No. 2014-021052, Office Action, dated Jan. 5, 2015.
Japanese Patent Application No. 2014-506591, Notice of Allowance, dated Oct. 3, 2016.
Japanese Patent Application No. 2014-506591, Office Action, dated Jan. 4, 2016.
Japanese Patent Application No. 2015-171851, Decision of Rejection, dated Feb. 6, 2017.
Japanese Patent Application No. 2015-186876, Office Action, dated Jul. 15, 2016.
Japanese Patent Application No. 2016-214237, Notice of Reasons for Rejection, dated Sep. 4, 2017.
Mexican Patent Application No. MX/a/2010/012691, Office Action, dated Feb. 10, 2014.
Mexican Patent Application No. MX/a/2010/012691, Office Action, dated Sep. 24, 2014.
Taiwan Patent Application No. 103109332, Office Action, dated Aug. 22, 2016.
Taiwan Patent Application No. 103109475, Office Action, dated Aug. 26, 2016.
U.S. Appl. No. 12/123,888, Nonfinal Office Action, dated Dec. 22, 2010.
U.S. Appl. No. 12/123,888, Notice of Allowance, dated Jan. 12, 2012.
U.S. Appl. No. 12/123,888, Office Action, dated Apr. 8, 2010.
U.S. Appl. No. 12/123,888, Office Action, dated Jun. 8, 2011.
U.S. Appl. No. 12/123,888, Office Action, dated Oct. 5, 2009.
U.S. Appl. No. 12/178,447, Final Office Action, dated Mar. 30, 2010.
U.S. Appl. No. 12/178,447, Non-Final Office Action, dated Dec. 22, 2010.
U.S. Appl. No. 12/178,447, Nonfinal Office Action, dated Oct. 15, 2009.
U.S. Appl. No. 12/178,447, Notice of Allowance, date Jun. 24, 2011.
U.S. Appl. No. 12/178,447, Notice of Allowance, dated Apr. 6, 2011.
U.S. Appl. No. 12/454,531, Non-Final Office Action, dated Sep. 13, 2013.
U.S. Appl. No. 12/993,163, Final Office Action, dated Feb. 22, 2016.
U.S. Appl. No. 12/993,163, Non-Final Office Action, dated Dec. 27, 2013.
U.S. Appl. No. 12/993,163, Non-Final Office Action, dated Jul. 28, 2016.
U.S. Appl. No. 12/993,163, Office Action, dated May 8, 2015.
U.S. Appl. No. 13/269,740, Office Action, dated May 20, 2013.
U.S. Appl. No. 13/269,740, Restriction Requirement, dated Apr. 2, 2013.
U.S. Appl. No. 13/269,750, Final Office Action, dated Dec. 26, 2013.
U.S. Appl. No. 13/269,750, Final Office Action, dated Oct. 18, 2016.
U.S. Appl. No. 13/269,750, Non Final Office Action, dated May 3, 2016.
U.S. Appl. No. 13/269,750, Non-Final Office Action, dated Aug. 21, 2014.
U.S. Appl. No. 13/269,750, Non-final Office Action, dated Jun. 21, 2013.
U.S. Appl. No. 13/269,750, Notice of Allowance, dated Feb. 8, 2017.
U.S. Appl. No. 13/269,750, Office Action, dated Aug. 10, 2015.
U.S. Appl. No. 13/269,750, Office Action, dated Mar. 12, 2015.
U.S. Appl. No. 13/269,750, Office Action, dated Nov. 18, 2015.
U.S. Appl. No. 13/454,531, Final Office Action, dated Sep. 23, 2016.
U.S. Appl. No. 13/454,531, Non-Final Office Action, dated Dec. 28, 2012.
U.S. Appl. No. 13/454,531, Non-Final Office Action, dated Mar. 17, 2016.
U.S. Appl. No. 13/454,531, Notice of Allowance, dated Oct. 5, 2015.
U.S. Appl. No. 13/454,531, Office Action, dated Apr. 21, 2015.
U.S. Appl. No. 13/454,531, Office Action, dated Oct. 7, 2014.
U.S. Appl. No. 14/112,479, Final Office Action, dated Feb. 27, 2017.
U.S. Appl. No. 14/112,479, Nonfinal Office Action, dated Jul. 12, 2017.
U.S. Appl. No. 14/112,479, Nonfinal Office Action, dated Jul. 29, 2016.
U.S. Appl. No. 29/548,507, Denzer et al., filed Dec. 14, 2015.
U.S. Appl. No. 29/548,508, Denzer et al., filed Feb. 14, 2015.
Search Report for Taiwan Patent Application No. 106100512, Office Action, dated Dec. 4, 2017.
"Final Office Action" dated Oct. 18, 2016 issued related U.S. Appl. No. 13/269,150.
"Office Action", dated Mar. 8, 2015, issued in related U.S. Appl. No. 13/269,750.
Australian Patent Application No. 2017202210, Examination Report No. 1, dated Oct. 25, 2018.
Australian Patent Application No. 2018253467, Examination Report No. 1, dated Dec. 6, 2019.
Australian Patent Application No. 2019202863, Examination Report No. 1, dated Sep. 13, 2019.
Canadian Patent Application No. 2724641, Office Action, dated May 27, 2019.
Canadian Patent Application No. 3021845, Examiner's Report, dated Aug. 19, 2019.
European patent application No. 12774589.1, Examination Report, dated Oct. 31, 2017.
European patent application No. 14765760.5, Partial Supplementary Search Report, dated Oct. 24, 2016.
European Search Report and Search Opinion Received for EP Application No. 19154409.7, dated Oct. 31, 2019, 9 pages.
Examiner initiated interview summary, U.S. Appl. No. 15/782,951, dated Oct. 11, 2019, 2 pages.
International Application No. PCT/US09/44693, filed May 20, 2009, entitled, "Autoinjector System", Slate, et al.

(56) References Cited

OTHER PUBLICATIONS

International Patent Application No. PCT/US09/44693, Written Opinion of the International Searching Authority, dated May 20, 2009.
Japanese Patent Application No. 2017-089529, Notice of Reasons for Rejection, dated Apr. 2, 2018.
Japanese Patent Application No. 2017-089529, Notice of Reasons for Rejection, dated Sep. 14, 2018.
Japanese Patent Application No. 2018-188224, Notice of Reasons for Rejection, dated Aug. 5, 2019.
Japanese Patent Application No. 2018-228060, Notice of Reasons for Rejection, dated Oct. 21, 2019.
Non-Final Office Action issued in related U.S. Appl. No. 12/993,163, dated Sep. 11, 2014.
Non-Final Office Action, U.S. Appl. No. 15/167,068, dated Oct. 9, 2019, 12 pages.
Notice of Allowance, U.S. Appl. No. 15/782,951, dated Oct. 11, 2019, 9 pages.
Office Action received for European Patent Application No. 14765760.5, dated Jul. 9, 2019, 4 pages.
Related International Patent Application No. PCT/US2014/028363, Mar. 14, 2014.
U.S. Appl. filed Feb. 23, 2017, John B. Slate et al., U.S. Appl. No. 15/440,420.
U.S. Appl. filed Jul. 23, 2008, John B. Slate et al., U.S. Appl. No. 12/178,447.
U.S. Appl. filed May 27, 2011, entitled, "Autoinjector System," of Slate et al., U.S. Appl. No. 12/993,163.
U.S. Appl. filed May 27, 2016, John B. Slate et al., U.S. Appl. No. 15/167,068.
U.S. Appl. No. 15/167,068, Final Office Action, dated Apr. 24, 2019.
Unpublished related U.S. Appl. No. 14/777,255.
U.S. Appl. No. 15/167,068, Non-final Office Action, dated Oct. 18, 2018.
U.S. Appl. No. 15/167,068, Non-Final Office Action, dated Oct. 9, 2019.
U.S. Appl. No. 15/782,925, Final Office Action, dated Oct. 11, 2019.
Canadian Patent Application No. 3021845, Examiner's Report, dated May 7, 2020.
U.S. Appl. No. 15/782,951, Notice of Allowance, dated May 20, 2020.
U.S. Appl. No. 15/952,296, Notice of Allowance, dated Jun. 1, 2020.
European Patent Application No. 19191313.6, European Search Report, dated Dec. 16, 2019.
Japanese Patent Application No. 2016-502669, Notice of Reasons for Rejection, dated Jan. 14, 2020., Jan. 14, 2020.
Japanese Patent Application No. 2018-086731, Decision of Rejection, dated Feb. 3, 2020.
U.S. Appl. No. 15/167,068, Nonfinal Office Action, dated Feb. 14, 2020.
U.S. Appl. No. 15/952,296, Nonfinal Office Action, date Jan. 14, 2020.
Japanese Patent Application No. 2019-070580, Notice of Reasons for Rejection, dated Feb. 25, 2020.
U.S. Appl. No. 16/026,294, Nonfinal Office Action, dated Mar. 18, 2020.
Canadian Patent Application No. 3021845, Office Action, dated Dec. 4, 2020.
Japanese Application No. 2020-041954 Notice of Reasons for Rejection dated Jan. 4, 2021.

* cited by examiner

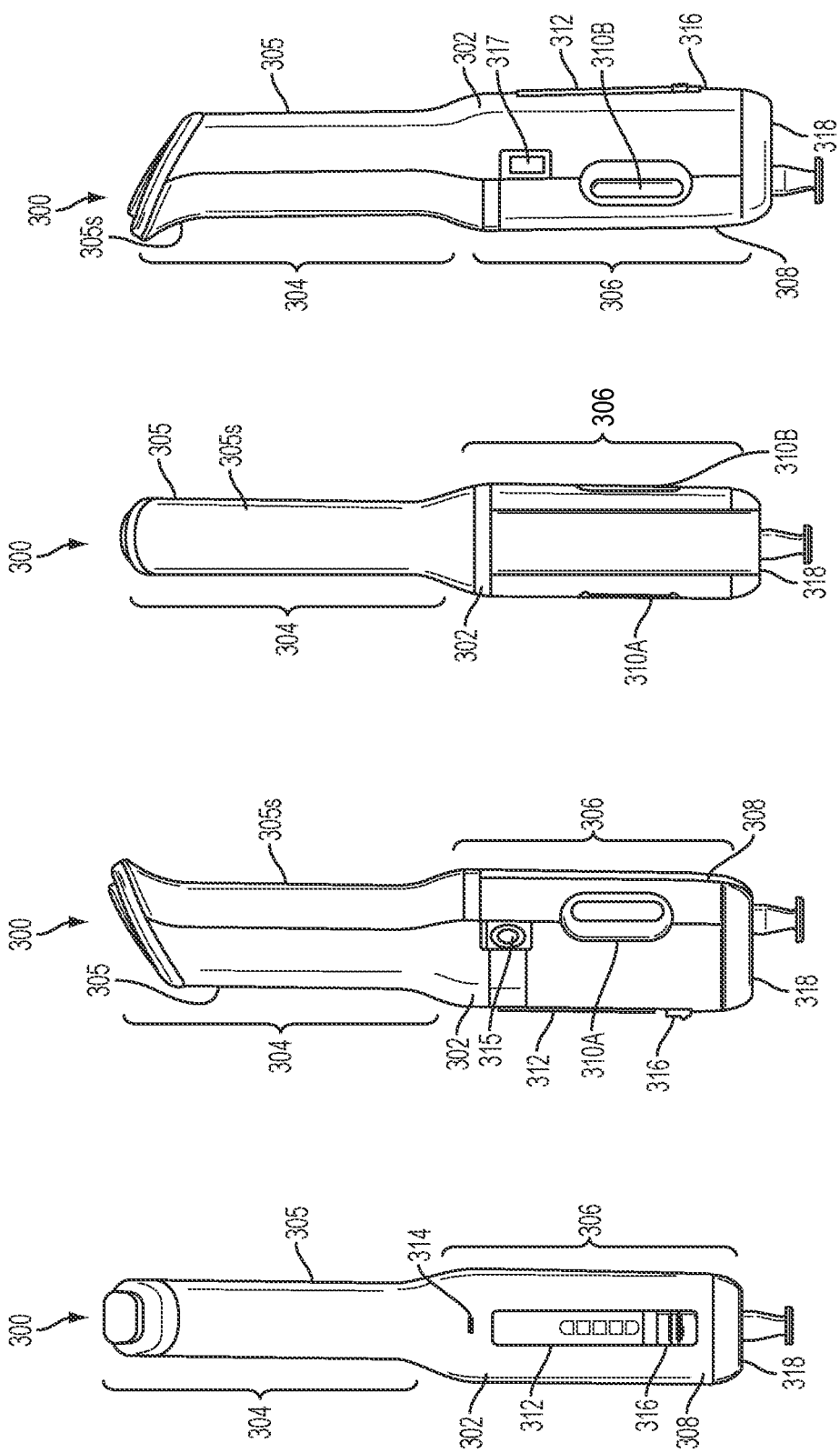

DRUG CASSETTE, AUTOINJECTOR, AND AUTOINJECTOR SYSTEM

CROSS-REFERENCE TO RELATED APPLICATIONS

This is a continuation of U.S. patent application Ser. No. 14/777,255, filed on Sep. 15, 2015, which is the US National Phase of PCT/US14/27950, filed Mar. 14, 2014, which claims the priority benefit of U.S. Provisional Patent Application 61/800,000, filed Mar. 15, 2013, the entire contents of each of which are incorporated herein by reference.

FIELD

The disclosure relates to injection systems and apparatus. More particularly, the disclosure relates to an autoinjector apparatus comprising an autoinjector and a cassette useable with the autoinjector, which conceals an injection needle of a drug container before and after an injection.

BACKGROUND

Pre-filled hypodermic syringes can be used for home-use because they may be prepared with a required dosage of a pharmaceutical product and are operated by merely advancing the stopper of the syringe. Aside from the costs of the particular medication used, pre-filled syringes may be economically manufactured.

Nevertheless, pre-filled syringes can have drawbacks. Specifically, many users are either frightened by an exposed injection needle or feel they are inherently incapable of performing an injection. Because of aversions to exposed needles, as well as health and safety issues that may be involved, various types of injectors and other devices have been developed for concealing needles from the user and automating the injection task to assist the user in performing the injection, ensure reliable delivery of the medication and ensure patient safety. See the following patents or patent applications, which are each herein incorporated by reference in its entirety: U.S. Pat. Nos. 8,052,645 and 8,177,749; U.S. Publ. No. 2012/0101439; and PCT Publ. No. WO 2012/145685.

Typically, three tasks may be performed when injecting a drug into a patient with a hypodermic syringe: 1) insertion of the needle into the patient; 2) injection of the drug from the syringe into the patient; and 3) withdrawal of the needle after the injection has been completed. For each task, the magnitude and direction of forces on the syringe, as well as the location of their application, may be different from the other tasks. For example, insertion of the needle may require the application of a minimal force on the syringe, for a very short period of time. On the other hand, injection of the medicament may require the application of a much greater force on the plunger of the syringe, and this force may need to be applied for a relatively longer period of time. Further, needle withdrawal may require the application of a force in an opposite direction from needle insertion. These, and other similar considerations, may become relevant when the injection process is to be automated.

In addition to these mechanical considerations, the design of an autoinjector may require user-friendly considerations. In particular, it may be desirable for the injection needle of the syringe to be operationally concealed from the view of a user. Preferably, this concealment is maintained before, during and after an injection procedure. Further, it may be desirable that operation of the syringe be limited to only those times when the syringe is properly positioned for an injection and/or when the appropriate sequence of actions are performed by the user.

Accordingly, an improved autoinjector apparatus is needed.

SUMMARY

Disclosed herein is a cassette for an autoinjector. It should be noted, however, that while the specification frequently refers to an autoinjector, in various embodiments the device may also be referred to as an injector. Reference to an autoinjector is often associated with a patient providing an injection to themselves, however, such an injection may also be administered by a health care provider. Similarly, use of an injector may be undertaken by either the patient or health care provider.

In various embodiments, the cassette may comprise a housing; and a cassette identification arrangement (cassette ID) defining a code containing information about the cassette, the code being detectable and decipherable by the injector, the cassette ID disposed on the housing, embedded within the housing, provided on or in a separate structure contained within the housing, or any combination thereof.

In various embodiments the cassette ID may comprise a contact system that requires contact between the cassette ID and the injector, a non-contact system that requires no contact between the cassette ID and the injector, or any combination thereof.

In various embodiments the contact system may comprise one or more tabs, one or more indentations, one or more electrically conductive strips, or any combination thereof, for contacting one or more sensing elements of a detector of the injector when the cassette is placed in or on the injector.

In various embodiments the code can be at least partially determined by the absence of one or more of the one or more tabs, indentations, electrically conductive strips, or any combination thereof.

In various embodiments the one or more tabs, indentations, electrically conductive strips, or any combination thereof are provided at various housing positions, the code at least partially determined by the various housing positions of the one or more tabs, indentations, electrically conductive strips, or any combination thereof.

In various embodiments the number of the one or more tabs, indentations, electrically conductive strips, or combination thereof, at least partially determines the code.

In various embodiments each of the one or more electrically conductive strips forms a straight or tortuous path, the code at least partially determined by the path of each of the one or more electrically conductive strips.

In various embodiments each of the one or more tabs may have a length selected from two or more different lengths, the code at least partially determined by the length of the one or more tabs.

In various embodiments each of the one or more indentations may have a depth selected from two or more different depths, the code at least partially determined by the depth of the one or more indentations.

In various embodiments the non-contact system may comprise a device for emitting a radio-frequency (RF), a device for emitting an electromagnetic field (EMF), a device for emitting a magnetic field (MF), a device for emitting a machine-readable optical representation of data (ORD), or any combination thereof, the RF, EMF, MF, ORD, or any combination thereof being sensed by a detector of the injector when the cassette is placed in or on the injector, the code at least partially determined by the RF EMF, MF, ORD, or any combination thereof.

In various embodiments the cassette may comprise a training cassette.

In various embodiments the cassette may comprise a drug cassette.

Various embodiments of the cassette may further comprise a container filled for treatment or prefilled with a drug.

In various embodiments the cassette may comprise a single-use cassette.

In various embodiments the information may comprise information that identifies the type of cassette, identifies the content of the cassette, identifies whether the cassette is an OEM cassette, identifies manufacturing data about the cassette, or any combination thereof.

In various embodiments the information that identifies the content of the cassette may comprise the quantity of drug in the container and/or drug characteristics.

In various embodiments the drug characteristics may comprise drug viscosity.

In various embodiments the information allows the injector to adjust or select its operational parameters or select one or a plurality of operational programs.

In various embodiments the operational parameters may comprise injection speed, needle insertion speed, pre and post-injection wait time, needle insertion depth, temperature limits, or any combination thereof.

In various embodiments the drug may comprise a therapeutic product.

In various embodiments the therapeutic product may be selected from the group consisting of Epogen®, Aranesp®, Enbrel® Neulasta®, Neupogen®, Nplate®, Vectibix®, Sensipar®, Xgeva® and Prolia®.

In various embodiments the therapeutic product may be an antibody to IL-17 Receptor A.

In various embodiments the therapeutic product may be an antagonist of angiopoietin-2.

In various embodiments the therapeutic product may be a TNF blocker or inhibitor.

In various embodiments the TNF blocker or inhibitor may be etanercept.

In various embodiments the TNF blocker or inhibitor may be adalimumab, certolizumab, golimumab or infliximab.

In various embodiments the therapeutic product may have a viscosity of about 19 centipoise at room temperature.

In various embodiments the therapeutic product may have a viscosity ranging between about 1 centipoise and about 320 centipoise, at room temperature.

In various embodiments the therapeutic product may have a viscosity ranging between about 5 centipoise and about 40 centipoise, at room temperature.

In various embodiments the therapeutic product may have a viscosity ranging between about 10 centipoise and about 35 centipoise, at room temperature.

In various embodiments the therapeutic product may have a viscosity ranging between about 15 centipoise and about 30 centipoise, at room temperature.

In various embodiments the therapeutic product may have a viscosity ranging between about 20 centipoise and about 25 centipoise, at room temperature.

In various embodiments the therapeutic product may have a viscosity ranging between about 16 centipoise and about 42 centipoise, at room temperature.

In various embodiments the therapeutic product may have a viscosity ranging between about 1 centipoise and about 29 centipoise, at room temperature.

In various further embodiments, the cassette may comprise a housing; a sleeve movably disposed within the housing, the sleeve for directly or indirectly holding a drug container; a locking arrangement for interlocking the sleeve with the housing, the locking arrangement comprising a spring-biased member associated with one of the housing and the sleeve, and a fixed member associated with the other one of the housing and the sleeve for interlocking with the spring-biased member.

In various embodiments the locking arrangement further may comprise a cam for unlocking the spring-bias and fixed members.

In various embodiments the cam is associated with the spring-biased member.

In various embodiments the spring-biased member may comprise at least one locking foot and the fixed member may comprise at least one slot, the at least one locking foot engaging the at least one slot in a locked position, to interlock the sleeve with the housing.

In various embodiments the at least one locking foot is disposed on a hand member.

In various embodiments the hand member is connected to the one of the housing and the sleeve by at least one flexible arm member, the at least one arm member biasing the hand member.

In various embodiments the at least one arm member biases the hand member in an unlocked position where the at least one locking foot is disengaged from the at least one slot.

In various embodiments the at least one arm member biases the hand member in the locked position where the at least one locking foot may be engaged with the at least one slot.

In various embodiments the cam may be disposed on the hand member.

In various embodiments the cam may be actuated by the injector during a needle-insertion cycle of the injector.

In various embodiments the at least one locking foot and the at least one slot have angled surfaces which engage one another if the at least one locking foot may be engaged with the at least one slot, to facilitate self-locking or self-unlocking thereof, depending upon the angle of the surfaces.

In various embodiments the locking arrangement further may comprise a second cam for preventing the spring biased member from interfering with the assembly of the sleeve to the housing.

In various embodiments the second cam may be disposed on the hand member.

In various embodiments the second cam extends forward of a leading edge of the hand member.

Various other embodiment of the cassette may further comprise a latch mechanism comprising a first member associated with the housing and a second member associated with the sleeve.

Various other embodiments of the cassette may comprise a housing having an aperture; a drug container disposed in the housing, the drug container having an injection needle and a needle shield disposed over the injection needle; a cassette cap for removing the needle shield, the cassette cap comprising a generally cylindrical body portion and a key portion disposed adjacent to the cylindrical body portion, the cylindrical body portion engaging the needle shield, the cylindrical body portion having a portion extending through the aperture in the housing that can be gripped to withdraw the cassette cap from the housing to remove the needle shield; and an anti-bending structure to prevent bending or flexing of the cassette cap, the cassette cap having at least first member associated with the key portion and the housing having at least a second member for interacting with the first member.

In various embodiments the first member may comprise a first pair of tabs.

In various embodiments the first pair tabs are disposed on side walls of the key portion.

In various embodiments the first member further may comprise a second pair of tabs spaced from the first pair of tabs.

In various embodiments the second pair tabs are disposed on side walls of the key portion.

In various embodiments the tabs extend from outer surfaces of the side walls.

In various embodiments the first pair of tabs are disposed adjacent a first end of the key portion and the second pair of tabs are disposed adjacent to a second end of the key portion.

In various embodiments the second member may comprise a pair of ribs.

In various embodiments the ribs are disposed on side walls of the housing.

In various embodiments the tabs engage surfaces of the ribs.

In various embodiments the ribs extend from interior surfaces of the side walls.

In various embodiments the portion of the cylindrical body extending through the aperture in the housing may have a gripping flange.

In various embodiments the sleeve contains a drug container filled with a drug.

In various embodiments the cassette is a disposable, single use cassette.

Further disclosed herein is an injector. In various embodiments, the injector may comprise a processor for controlling operational parameters of the injector; a surface for supporting a cassette having a cassette identification arrangement (cassette ID), the cassette ID defining a code that contains information about the cassette; and a detector communicatively coupled with the processor, the detector for detecting and communicating the cassette ID to the microprocessor to decipher the code defined therein.

In various embodiments the detector may comprise a contact system that requires contact between the cassette ID and the detector, a non-contact system that requires no contact between the cassette ID and the detector, or any combination thereof.

In various embodiments the contact system may comprise one or more switches, two or more pogo-pin connectors, or any combination thereof.

In various embodiments the one or switches can be switched into an off state and an on state.

In various embodiments the one or more switches can be switched into an off state, a first on state and at least a second on state.

In various embodiments simultaneous actuation of at least two of the two more pogo-pin connectors closes a circuit.

In various embodiments the non-contact system may comprise a device for receiving a radio-frequency (RF) electromagnetic field (EMF), a device for receiving a magnetic field (MF), a device for reading an optical representation of data, or any combination thereof.

In various embodiments the injector is reusable.

Various other embodiments of the injector may comprise a processor for controlling operational parameters of the injector; a surface for supporting a cassette having a cassette identification arrangement (cassette ID), the cassette ID defining a code that contains information about the cassette; and a detector communicatively coupled with the processor, the detector for detecting and communicating the cassette ID to the microprocessor to decipher the code defined therein in combination with the cassette embodied herein.

Further disclosed herein is a method of injecting a drug into a patient with an apparatus comprising an autoinjector and a cassette, wherein the drug may be contained in a drug container having an injection needle and a needle shield covering the injection needle, wherein the drug container may be disposed in the cassette, and wherein the cassette may be provided with a cassette cap for removing the needle. In various embodiments, the method may comprise activating a first door-open state of the injector; deactivating, in a computer process, all other operational states of the autoinjector in response to activating the first door-open state; activating, in a computer process, a device-on state of the autoinjector only after proper insertion of a valid one of the cassette into the autoinjector; activating, in a computer process, a cap-off state of the autoinjector only after removal of the cassette cap from the cassette; activating, in a computer process, a ready-to-inject state of the autoinjector only after the autoinjector is placed into stable contact with skin at an injection site; activating, in a computer process, an injection-process state of the autoinjector after activation of the autoinjector; and activating, in a computer process, a door open state of the autoinjector and maintaining the door open state and a device-on state of the autoinjector until the cassette is removed from the autoinjector.

In various embodiments the valid one of the cassette may comprise an unused cassette.

In various embodiments the device-on state allows removal of the cassette cap from the cassette and deactivates all other operational states of the autoinjector except a second manually activated door-open state that allows removal of the cassette from the autoinjector.

In various embodiments the cap-off state deactivates all other operational states of the autoinjector except a second manually activated door-open state that allows removal of the cassette from the autoinjector.

In various embodiments the proper insertion of the valid one of the cassette into the autoinjector is performed by providing a first member on the cassette that interacts with a second member in the autoinjector to allow the cassette to be inserted into the autoinjector only in the correct orientation.

In various embodiments the second member in the autoinjector may be disposed on the door of the autoinjector.

In various embodiments the first member may comprise a pin on a housing of the cassette and the second member may comprise a slot in the door of the autoinjector.

In various embodiments the first member may comprise at least the shape of a housing of the cassette and the second member may comprise at least the shape of the door, which matches the shape of the housing of the cassette.

Still further, a method is disclosed herein for treating a patient in need thereof. In various embodiments, the method may comprise providing a cassette containing a drug, and administering the drug to the patient using an injector.

In various embodiments, the method may further comprise inserting the cassette into the injector prior to administering the drug.

BRIEF DESCRIPTION OF THE DRAWINGS

The accompanying figures show embodiments according to the disclosure and are exemplary rather than limiting.

FIG. 2A is a front view of the autoinjector apparatus of FIG. 1 showing the cassette installed in the autoinjector.

FIG. 2B is a side view of a first side of the autoinjector apparatus of FIG. 1 showing the cassette installed in the autoinjector.

FIG. 2C is a rear view of the autoinjector apparatus of FIG. 1 showing the cassette installed in the autoinjector.

FIG. 2D is side view of a second side of the autoinjector apparatus of FIG. 1 showing the cassette installed in the autoinjector.

DETAILED DESCRIPTION

Figure 1:
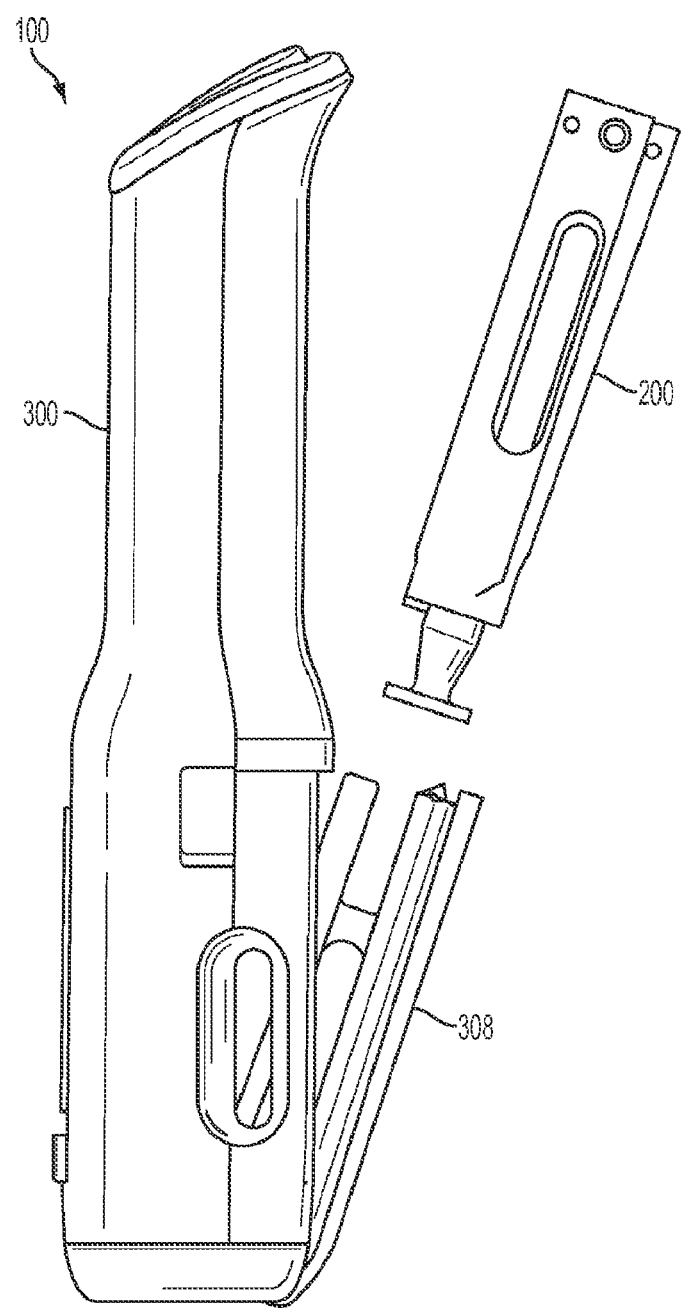
FIG. 1 is a side view of an embodiment of an autoinjector apparatus comprising a cassette and an autoinjector, showing the cassette prior to installation in the autoinjector.

FIG. 1 shows an embodiment of an autoinjector system or apparatus 100 that can be used for injecting a dose of pharmaceutical product (drug) into a patient, the injection often being self-administered by the patient (user). Alternatively, the drug can be administered by a health-care provider. As shown, the autoinjection system or apparatus 100 may comprise a removable cassette 200 and an autoinjector or injector 300. Various embodiments of the cassette 200 may be constructed to contain a drug to be injected into the user by the autoinjector 300. In various other embodiments the cassette 200 may be constructed for use in training the user to operate the autoinjector 300 (a training cassette). The autoinjector 300 may be constructed to deliver an injection automatically upon actuation by the user or some other person. Various embodiments of the autoinjector 300 may have a cassette door 308 that can be constructed to pivot between and an open position and a closed position to allow insertion of the cassette 200 into the autoinjector 300. In some embodiments, the cassette door 308 may include a "cassette" icon (not shown) that indicates the insertion entry point for the cassette 200.

Referring collectively to FIGS. 2A-2F, various embodiments of the autoinjector 300 may comprise a casing 302 having a handle section 304 and a cassette receiving section 306 inline with the handle section 304. To aid patients with manual dexterity issues, the handle section 304 of the autoinjector casing 302 may define an ergonomically shaped handle 305 with a soft grip area 305S. The cassette receiving section 306 comprises the cassette door 308 (FIGS. 2B and 2D) described earlier. The cassette door receives the cassette 200 in an open position (FIG. 1) and aligns the cassette 200 with insertion and extrusion drives, and other structures and components of the autoinjector 300 in a closed position. The cassette door 308 may include a "cassette" icon that indicates the insertion entry point for the cassette 200. The cassette receiving section 306 of the casing 302 may comprise windows 310A, 310B on sides thereof that align with windows of the cassette 200 when the cassette door 308 is closed with the cassette 200 correctly installed therein. In one or more embodiments, the windows 310A, 310B may be double-layered. One or more lights (not shown) may be provided inside the casing 302 to evenly backlight illuminate the cassette windows 212 (FIG. 5A) and the syringe 260 disposed within the inner sleeve 220 of the cassette 200 (FIG. 5B), so that the user can observe the injection cycle through the windows 310A, 310B of the autoinjector 300, i.e., observe the initial and end positions of the plunger-stopper 264 of the syringe 260 (FIG. 5B) during the syringe content (hereinafter "drug") extrusion process, as well as syringe movements within the cassette 200.

Referring still to FIGS. 2A, 2B, 2D, and 2F, the autoinjector 300 may further comprise a user interface 312 and an audio speaker (not shown). The user interface 312 (best illustrated in FIG. 2A) may be located in the cassette receiving section 306 of the casing 302, and provides various visual indicators. The audio speaker may be disposed inside the casing 302 and provides various audible indicators. The audio speaker may audibly communicate with the external environment via a speaker aperture 314 formed in the casing 302 in the cassette receiving section 306. The visual and audible indicators generated by the user interface 312 and the audio speaker can tell the user when the autoinjector 300 is ready for use, the progress of the injection process, injection completion, the occurrence of any errors, and other information. The autoinjector 300 may further comprise one or more of a settings/mute switch 315, a speed selector switch 316, a start button 307, and an eject button 317. The settings/mute switch 315 (FIG. 2B) may be located in the cassette receiving section 306 of the casing 302. The mute switch 315 may be constructed allow the user to turn on and off all synthesized sounds, except error sounds, and to respond in real-time so that if the user begins the injection process and changes the mute switch to off, the sounds are immediately muted. The mute switch 315 may also be constructed to slide toward a "mute" icon to mute the audio speaker. A light indicator may be provided to confirm the "mute" state. The speed selector switch 316 (FIGS. 2A and 2B) may be located in the cassette receiving section 306 of the casing 302. The speed selector switch 316 may be constructed to allow the user to select among a plurality of preset drug delivery (extrusion) speeds to accommodate personal patient preference. The speed selector switch 316 may comprise a three switch positions. Other embodiments of the speed selector switch may comprise two switch positions, or 4 or more switch positions. In still other embodiments, the speed selector switch may be of the infinitely variable type. In some embodiments, changing the position of the switch 316 prior to injection changes the speed of drug extrusion during injection while changing the position of the speed selector switch 316 during injection, does not change the speed of the injection in real time. The autoinjector 300 may also be provided with one or more demo cassettes to allow the user to experiment with different speeds of drug delivery. The start button 307 may be disposed at a free end of the handle 305. The button 307 may include an indentation 307I (FIG. 2F) for optimizing thumb placement on the button 307. The button 307 may be made of a translucent material that allows a lighting effect to illuminate the button as signals. The eject button 317 (FIG. 2D) may be located in the cassette receiving section 306 of the casing 302. The eject button 317 may include an indentation 317I for optimizing finger placement on the button 317. In some embodiments, the eject button 317 may be controlled by the microprocessor 350 (FIG. 2H) of the autoinjector 300, which may be programmed to eliminate accidental inputs during the injection process.

Figure 2E:
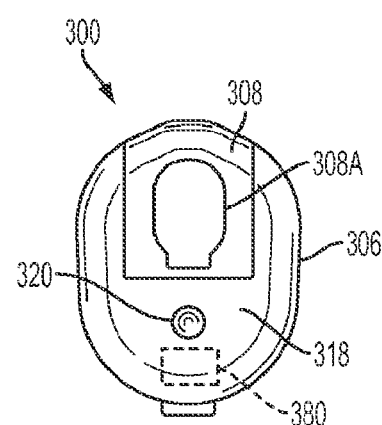
FIG. 2E is an end view of a first end of the autoinjector of the autoinjector apparatus of FIG. 1.
Figure 2F:
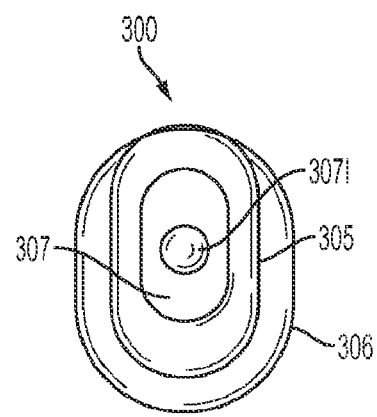
FIG. 2F is an end view of a second end of the autoinjector of the autoinjector apparatus of FIG. 1.

Referring to FIG. 2E, the cassette receiving section 306 of the casing 302 and the cassette door 308 may form a proximal end wall 318 of the autoinjector 300. The proximal end wall 318 may be configured as a broad, flat and stable base for easily positioning the autoinjector 300 on a support surface, after removal of the shield remover 240 (FIG. 5A) or when the autoinjector 300 does not contain the cassette 240. The portion of the proximal end wall 318 formed by the cassette door 308 may include an aperture 308A that is sized and shaped to allow the shield remover 240 to be removed from the cassette 200 and withdrawn through the aperture 308A, when the cassette 200 is installed in the autoinjector 300. The proximal end wall of the autoinjector 300 may further comprise a target light 320. The target light 320 may be constructed to turn on when the shield remover 240 is removed from the cassette 200 and withdrawn through the aperture 308A, thereby visually indicating that the shield remover 240 has been removed. Once turned on, the target light aids the user in visualizing and selecting an injection site.

Referring still to FIG. 2E, the autoinjector 300 may further comprise a capacitance-based skin sensor 380 (shown with broken lines) or any other suitable skin sensor. The skin sensor 380 may coupled to a microprocessor provided, for example, in the autoinjector 300 in a manner that allows signals or data to be communicated to the microprocessor, so that the autoinjector 300 can determine when the proximal end wall 318 of the autoinjector 300 touches or contacts skin without the need to provide downward pressure on the injection-site area. The skin sensor 380 may also be constructed to inform the user through audible and visual indicators generated by the speaker and user interface, when skin contact is detected. In some embodiments, the skin sensor 380 may comprise two pads or electrodes (not shown) imbedded in the proximal end wall 318 of the autoinjector 300. When an electrode is touched, its capacitance signal increases. If the increase is sufficient as determined by the microprocessor, which may be programmed with sensor decision logic, that electrode will become activated. To determine whether skin contact has been made, the microprocessor reads the capacitance of the electrodes. The microprocessor then processes the capacitance information to determine when the electrodes are both making proper contact with the skin.

Figure 2G:
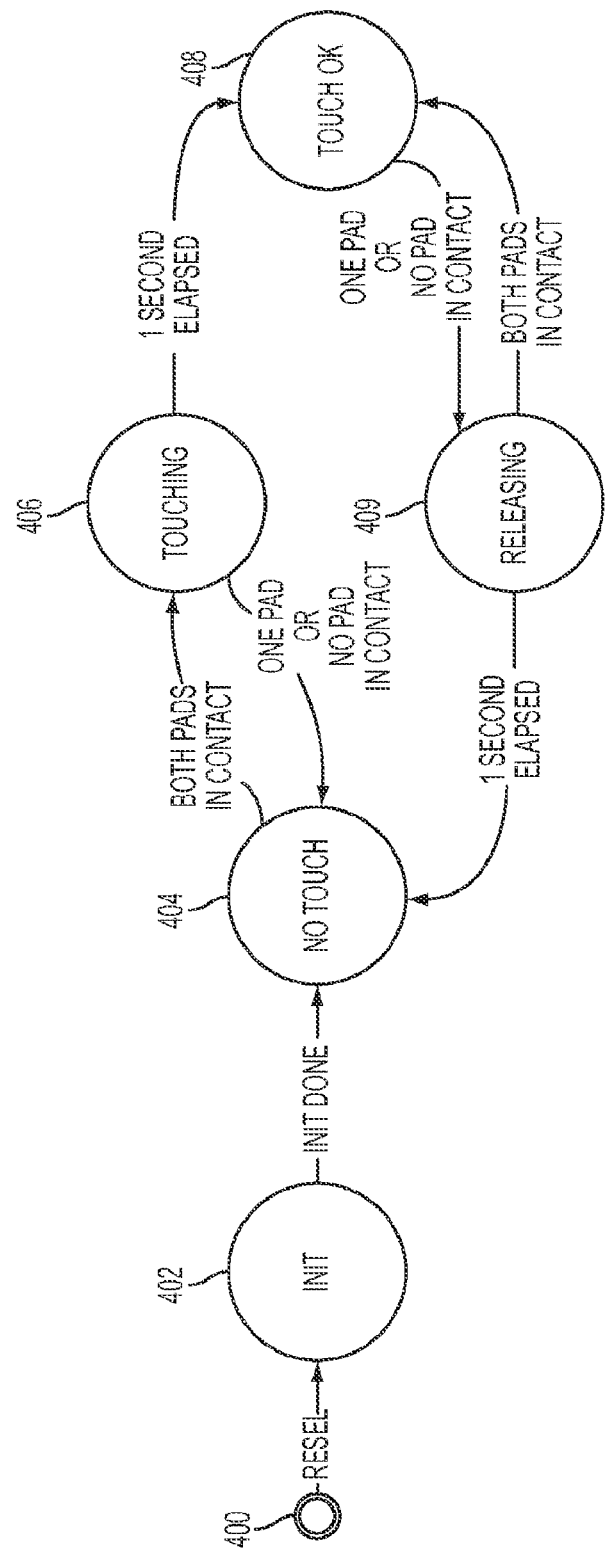
FIG. 2G is a state diagram showing an embodiment of the decision logic for controlling a skin sensor of the autoinjector apparatus of FIG. 1.

FIG. 2G is a state diagram illustrating the decision logic for controlling skin sensor 380 with the microprocessor of the autoinjector 300, according to an embodiment of the present disclosure. The process starts at 400 which represents a reset of the autoinjector. The logic then flows to state 402 which represents the initialization of the skin sensor after the reset of the autoinjector. Once initialized, the logic flows to state 404 which represents a "no-touch" state where none or only one of electrodes of the sensor touch skin. If both electrodes touch skin for less than a certain threshold time period (e.g., one second), the logic flows to state 406 which represents a "touching" state. If one or neither one of the electrodes touches skin, the logic flows back to state 404. If, however, both electrodes touch skin for a period of time equal to the threshold time period (e.g., one second), the logic flows to state 408 which represents a "touch OK" state. If one electrode or no electrodes contact skin, the logic flows to a "releasing" state 409. If both electrodes touch skin, the logic flows back to "touch OK" state 408. If one or no electrodes contact skin for more than the threshold time period (e.g., more than one second), the logic flows back to "no touch" state 404.

Figure 2H:
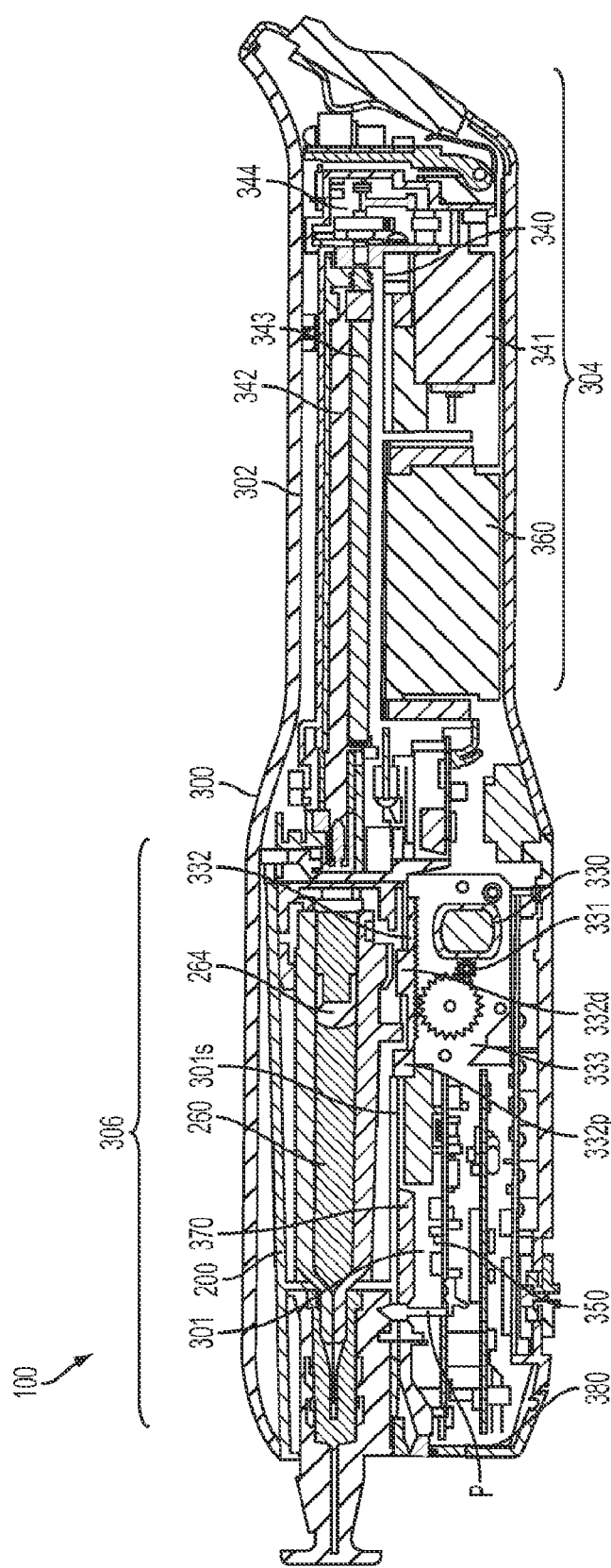
FIG. 2H is a sectional side view of an embodiment of the autoinjector apparatus showing the cassette installed in the autoinjector.

As shown in FIG. 2H, various embodiments of the autoinjector 300 may comprise a chassis 301 disposed in the casing 302 for supporting a motorized needle insertion drive 330, a motorized drug extrusion drive 340, a microprocessor 350, a battery 360 for powering the drives 330, 340 and the microprocessor 350, and the skin sensor 380. The casing 302 may define an ergonomically shaped handle section 304 and a cassette receiving section 306. The chassis 301 may include a support surface 301s for supporting one or more cassettes 200 in the autoinjector 300 and aligning the cassette 200 or a selected one of the one or more cassettes 200 with motorized needle insertion and drug extrusion drives 330 and 340, respectively. A detector 370 may be provided on or in the cassette support surface 301s for sensing the presence of and/or information about the cassette 200. The detector 370 may be coupled with the microprocessor 350 in a manner that allows signals or data to be communicated to the microprocessor 350. The insertion drive 330 may include an insertion rack 332, an insertion drive motor 331 and an insertion drive gear train 333 for transmitting rotary motion of the insertion drive motor 331 to drive the rack 332. The insertion rack may include a tab arrangement including, for example, proximal and distal tabs 332p and 332d, respectively, which interface with the cassette 200. The extrusion drive 340 may comprise an extrusion drive motor 341, a plunger rod 342, a lead screw 343, and an extrusion drive gear train 344. The plunger rod 342 is driven by the extrusion drive motor 341 through the lead screw 343 and the extrusion drive gear train 344, and may interface with a plunger 264 of a drug container 260 contained within the cassette 200. The autoinjector 300 can be used for executing multiple injections.

Referring still to FIG. 2H, the microprocessor 350 of the autoinjector 300 may be programmed with instructions that, when executed by the microprocessor 350, enable it to control and monitor the various operations and functions of the autoinjector 300. For example, but not limitation, the microprocessor 350 may be programmed with instructions for controlling the motorized insertion and extrusion drives 330, 340. Such instructions may control and monitor each step of the injection cycle and process flow, thereby automating needle insertion, drug extrusion, and needle retraction, and controlling the sequence of actions performed by the user so that the injection process and drug administration can be made more reliable, accurate, and consistent. The microprocessor 350 may also be programmed with instructions for controlling the audible and visual feedbacks to the user. An automated power-on self-test checks the operation of the autoinjector 300 and remaining battery charge.

In various other embodiments, the autoinjector 300 may include other types of needle insertion drives, drug extrusion drives, and means for activating and sequencing the drives. The insertion and extrusion drives, in such embodiments may be implemented as separate and distinct mechanisms or combined into a single mechanism. The insertion and extrusion drives of such embodiments may be powered, without limitation, by motors, mechanical mechanisms (e.g., elastic members such as springs), gas pressure mechanisms, gas releasing mechanism, or any combination thereof. Various transmission mechanisms may be used for transmitting the power to the cassette, to cause injection of the drug. In addition, the activating and sequencing means may comprise various mechanical and electromechanical arrangements, which may be combined with the microprocessor described earlier or used alone. The autoinjector in such embodiments may be constructed to be reusable for executing multiple injections or be designed for a single, disposable use.

Figure 3:
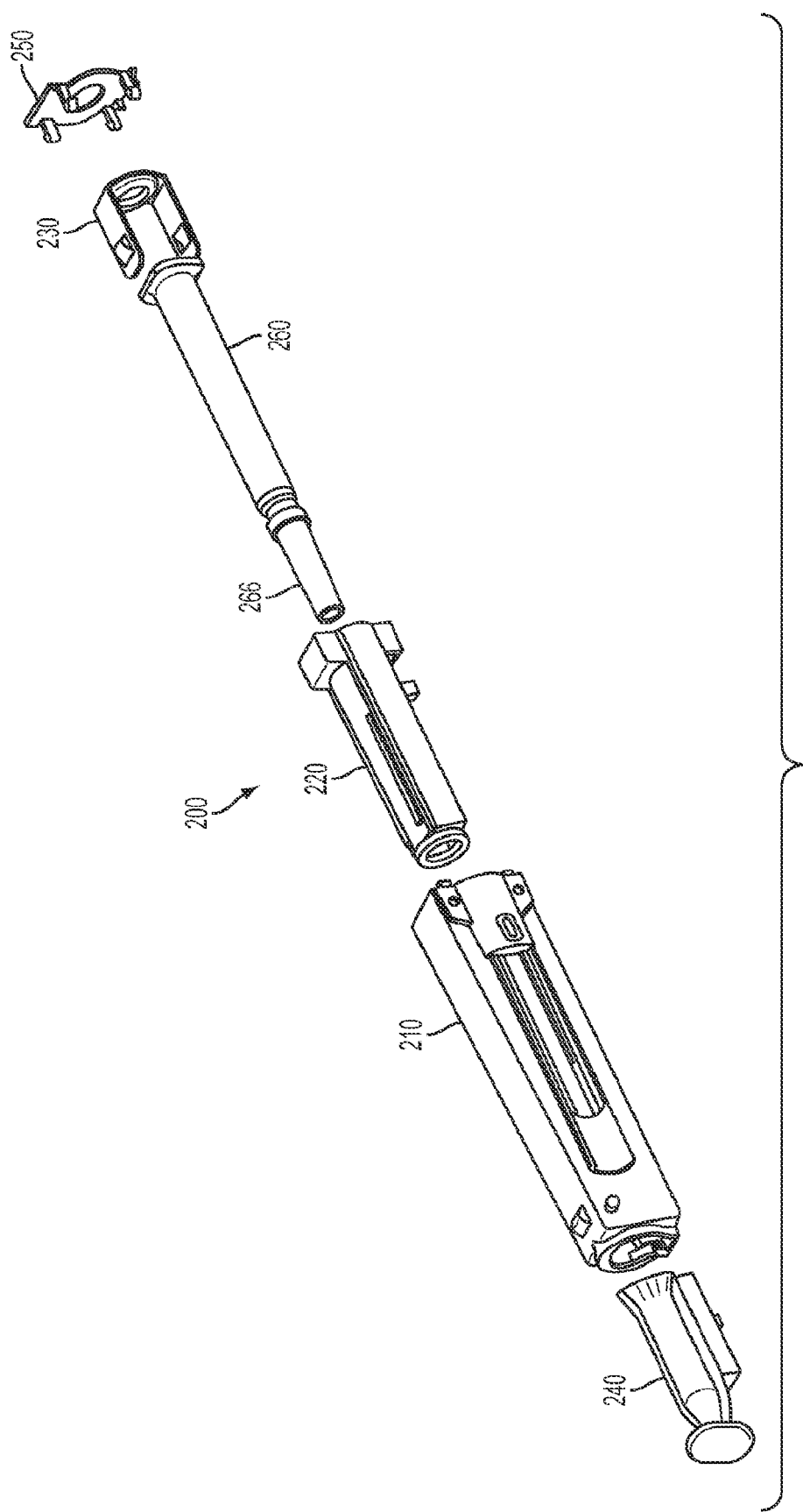
FIG. 3 is an exploded perspective view of an embodiment of the cassette.

Referring now to FIG. 3, various embodiments of the cassette 200 may comprise an outer housing 210, an inner sleeve 220, a drug container 260 for containing a drug, a cassette cap 240, a lock cap 230, and a cover 250. Such embodiments of the cassette 200 facilitate and enable easy injection of the drug with the autoinjector and can be constructed for a single, disposable use. In various embodiments, the lock cap 230 and cover 250 of the cassette 200 may be constructed to resist removal of the drug container 260 from the cassette 200, thereby preventing needle sticks before and after use of the cassette 200 and also preventing the drug container 260 from being taken out of the cassette 200 or replaced. In addition, the lock cap 230 and cover 250 protect the drug container 260 during shipment and transportation. The cassette cap 240, in various embodiments, may be constructed to remove a needle shield 266 covering an injection needle associated with the drug container 260. In various other embodiments, the cassette cap 240 may also be constructed to engage the outer housing 210 of the cassette 200, such that the cassette cap 240 cannot be rotated or twisted, thereby preventing the needle shield 266 from damaging the injection needle. Various embodiments of the inner sleeve 220 may be constructed to position the drug container 260 within the cassette housing 210 in either a needle-concealed position or a needle injection position during an injection cycle of the autoinjector. In various other embodiments, the outer housing 210 and the inner sleeve 220 of the cassette 200 may include one or more locking arrangements that protect the drug container 260 and prevent unintended needle exposure or damage. Various other embodiments of the cassette 200 may include a cassette identification arrangement that interfaces with the autoinjector to communicate the installation of the cassette 200 within the autoinjector and/or information about the cassette 200.

Figure 4:
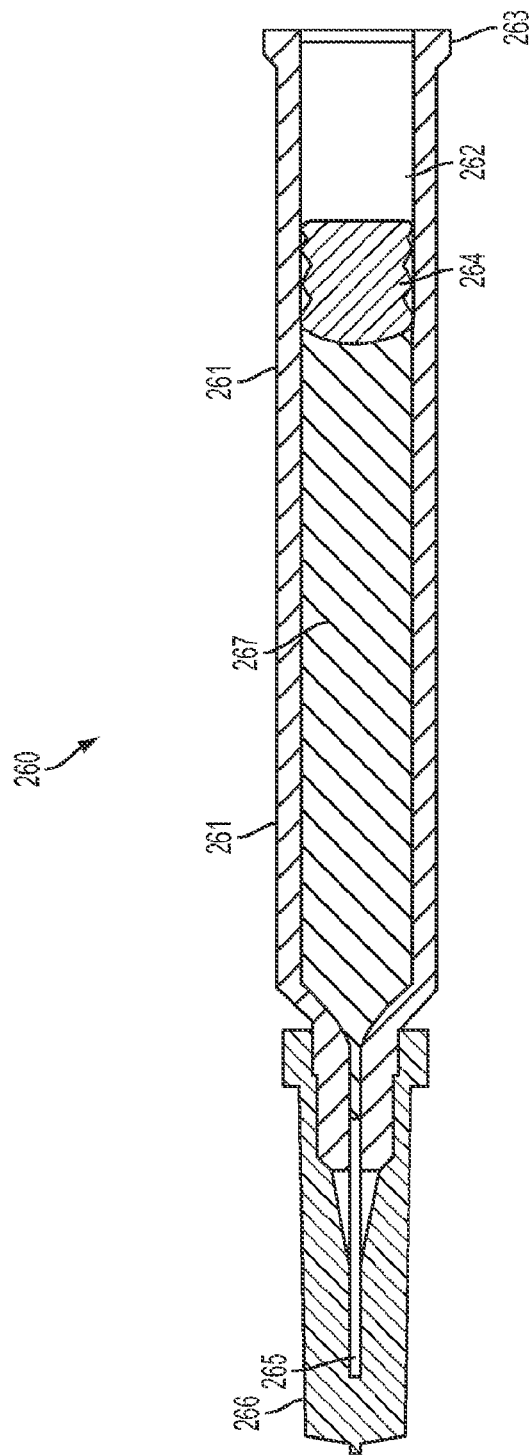
FIG. 4 is a sectional side view of an embodiment of a drug container that can be provided in the cassette.

As shown in FIG. 4, the drug container 260 may comprise a conventional glass or plastic syringe comprising a barrel 261 that defines a fluid chamber 262. The fluid chamber 262 may be filled for treatment or be prefilled with a predetermined dose of a drug 267. The drug may have a viscosity that depends on the temperature of the product. The syringe 260 may further comprise an injection needle 265 removably or fixedly disposed at a proximal end of the barrel 261, and an outwardly extending flange 263 disposed at a distal end of the barrel 261. The injection needle 265 may communicate with the fluid chamber 262 to allow dispensing of the predetermined dose of the drug 267 expelled from the fluid chamber 262 of the syringe barrel 261. The syringe 260 may further comprise a moveable plunger-stopper 264, disposed within the fluid chamber 262 of the barrel 260, for expelling the predetermined dose of the drug 267 from the chamber 261 so that it may be dispensed through the injection needle 265. A protective needle shield 266 made, for example, of a non-rigid material, may be provided for covering the injection needle 265.

In some embodiments, the drug contained in the drug container 260 may have a viscosity of about 19 centipoise, at room temperature (20 to 25° C. [68-77° F.]).

In some embodiments, the drug contained in the drug container 260 may have a viscosity ranging between about 1 centipoise and about 320 centipoise, at room temperature.

In some embodiments, the drug contained in the drug container 260 may have a viscosity ranging between about 5 centipoise and about 40 centipoise, at room temperature.

In some embodiments, the drug contained in the drug container 260 may have a viscosity ranging between about 10 centipoise and about 35 centipoise, at room temperature.

In some embodiments, the drug contained in the drug container 260 may have a viscosity ranging between about 15 centipoise and about 30 centipoise, at room temperature.

In some embodiments, the drug contained in the drug container 260 may have a viscosity ranging between about 20 centipoise and about 25 centipoise, at room temperature.

In some embodiments, the drug contained in the drug container 260 may have a viscosity ranging between about 16 centipoise and about 42 centipoise, at room temperature.

In some embodiments, the drug contained in the drug container 260 may have a viscosity ranging between about 1 centipoise and about 29 centipoise, at room temperature.

Figure 5A:
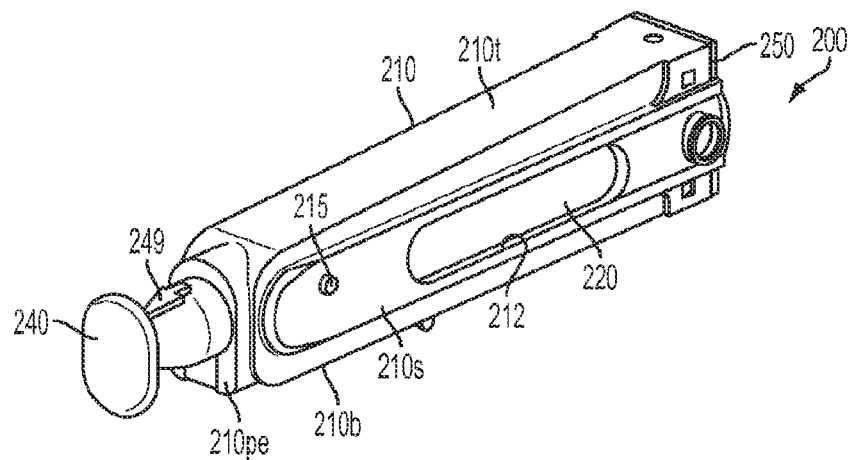
FIG. 5A is a top down front perspective view of an embodiment of the cassette.
Figure 5B:
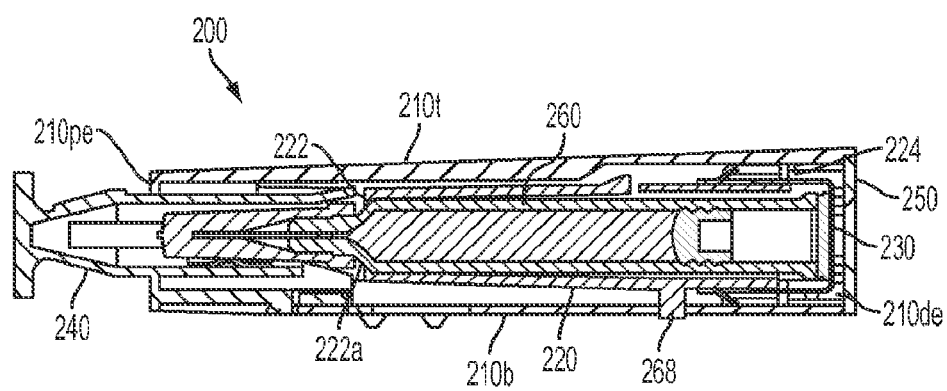
FIG. 5B is a sectional side view of the cassette of FIG. 5A.
Figure 5C:
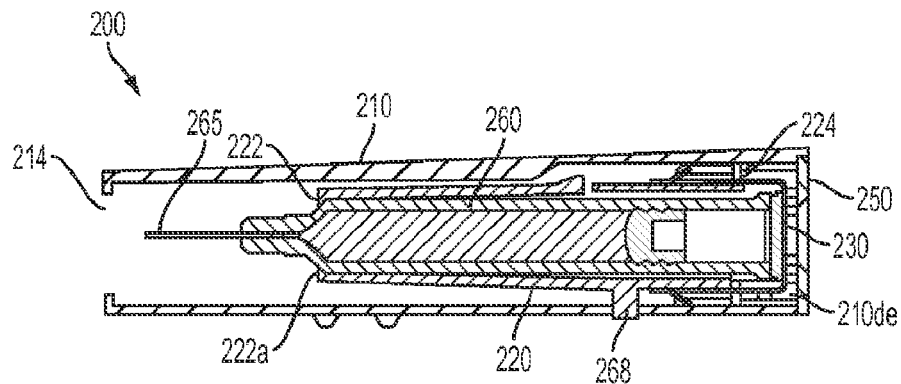
FIG. 5C is a sectional side view of the cassette of FIG. 5A after removal of a cassette cap of the cassette.

Referring collectively to FIGS. 5A-5D, various embodiments of the outer housing 210 of the cassette 200 may comprise a top wall 210t, a bottom wall 210b, side walls 210s connecting the top and bottom walls 210t and 210b, respectively, a front or proximal end wall 210pe and an open rear or distal end 210de. The proximal end wall 210pe of the outer housing 210 may include an aperture 214 (FIGS. 5C and 5D), which is constructed to removably receive the cassette cap 240. The outer housing 210 may be constructed to retain the inner sleeve 220 therein while allowing it to be freely moved within the outer housing 210 in a slidable manner after removal of the cassette cap 240 (FIG. 5C). Some embodiments of the outer housing 210 may comprise an elongated opening or window 212 in each side wall 210s thereof (FIG. 5A). The outer housing 210 of the cassette 200 may also include a pin 215 (FIG. 5A) or any other suitable mechanical structure that prevents the cassette 200 from being inserted into the cassette door in the wrong direction and/or orientation. An "arrow" icon may be provided on the outer housing 210 (not shown) to indicate the proper direction and orientation for inserting the cassette into the cassette door.

Figure 5D:
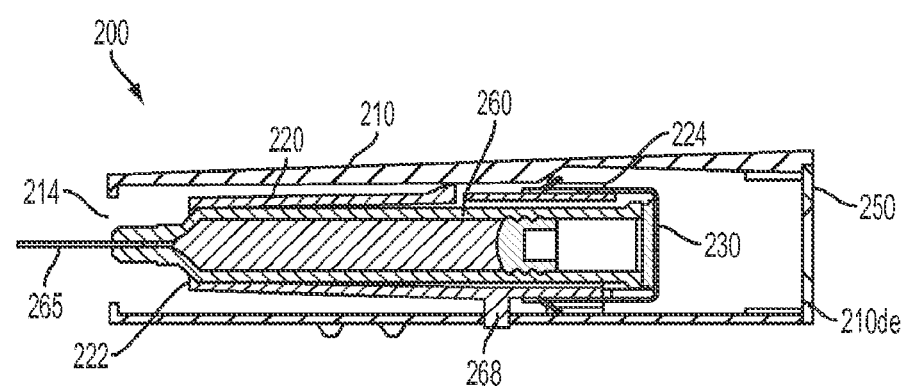
FIG. 5D is a sectional side view of the cassette of FIG. 5C showing a prefilled drug container of the cassette in a needle-injected position.

Referring still to FIGS. 5A-5D, various embodiments of the inner sleeve 220 may comprise proximal and distal ends 222 and 224, respectively. The sleeve 220 may be sized and dimensioned to directly or indirectly hold the drug container 260 therein in a secure manner. The proximal end 222 of the inner sleeve 220 may define an aperture 222a which is constructed to allow the injection needle 265 of the drug container 260 to extend therethrough (FIG. 5C). The inner sleeve 220 may further comprise a drive post 268, which allows it to be driven by the insertion drive of the autoinjector during the needle insertion cycle of the autoinjector's injection cycle. As can be seen in FIGS. 5C and 5D, the inner sleeve 220 can be driven through the outer housing 210 of the cassette 200 by the insertion drive of the autoinjector, during which the drug container 260 moves from a distal position in the outer housing 210 (FIG. 5C) to a proximal position in the outer housing 210 (FIG. 5D) and then back to the distal position. When the inner sleeve 220 is in the distal position (needle-concealed position), as shown in FIG. 5C, the injection needle of the drug container 260 is contained within the outer housing 210 of the cassette 200 and concealed from view by the user. When the inner sleeve 220 is in the proximal position (needle-injection position), as shown in FIG. 5D, the injection needle of the drug container 260 extends out through the aperture 214 in the proximal end wall 210pe the outer housing 210 of the cassette 200 and the autoinjector (not shown). The lock cap 230 closes the open distal end 224 of the inner sleeve 220 thereby locking the drug container 260 within the inner sleeve 220, so that the drug container 260 moves with the inner sleeve 220 as it is driven forward or backward through the outer housing 210 by the insertion drive of the autoinjector, during the insertion cycle of the autoinjector 300. The cover 250 closes the open distal end 210de of the outer housing 210 and prevents tampering with the drug container 260 by encasing the inner sleeve 220 and the drug container 260 within the outer housing 210 of the cassette 200, and also completes the cosmetic appearance of the cassette 200. The inner sleeve 220 may be made from a transparent, rigid material, such as a clear polycarbonate, to allow viewing of the drug container 260 through the windows 212 in the side walls 210s of the outer housing 210.

Figure 6A:
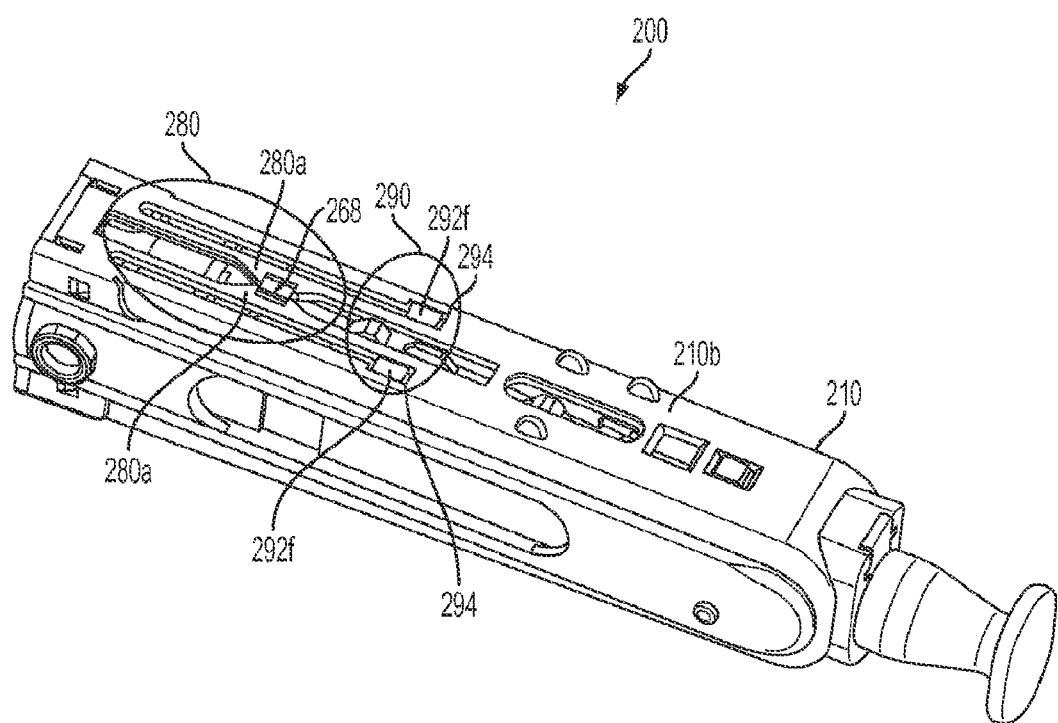
FIG. 6A is a bottom down front perspective view of an embodiment of the cassette showing an inner sleeve latch mechanism and an inner sleeve locking arrangement.
Figure 6B:
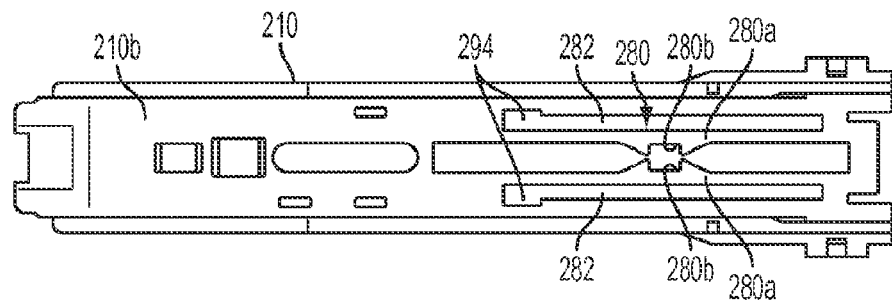
FIG. 6B is a bottom view of an embodiment of an outer housing of the cassette shown in FIG. 6A showing certain elements of the inner sleeve latch mechanism and the inner sleeve locking arrangement.

Referring collectively to FIGS. 6A and 6B, various embodiments of the outer housing 210 of the cassette 200 may comprise a latch mechanism 280 that latches the drive post 268 of the inner sleeve 220 to retain the sleeve 220 and, therefore, the injection needle of the drug container, in a needle-concealed position to protect the drug container and prevent unintentional needle exposure to the user. As best shown in FIG. 6B, the latch mechanism 280 may include a pair of resilient, opposing latch arms 280a formed in a bottom wall 210b of the outer housing 210, or any other wall of the housing 210 that allows the insertion drive to engage the drive post 268 of the inner sleeve 220. The latch arms 280a may define locking detent slots 280b (FIG. 6B) through which the drive post 268 of the inner sleeve 220 extends.

During assembly of the cassette 200, the inner sleeve 220 containing the drug container, may be inserted into the outer housing 210 so that the drive post 268 of the inner sleeve 220 spreads apart and slides between the latch arms 280a of the outer housing 210 and then enters the detents slots 280b of the latch arms 280a, where it is latched, as shown in FIG. 6A. During the needle-insertion cycle of the autoinjector, the insertion drive moves the distal tab 332d in the proximal direction thereby forcing the latch arms 280a to spread apart and unlatch the drive post 268 of the inner sleeve 220, thereby allowing proximal and distal movement of the unlatched inner sleeve 220 through the cassette outer housing 210, via the drive post 268.

Once unlatched, the insertion drive can move the inner sleeve 220 and, therefore, the drug container disposed therein from the needle-concealed position to the needle injection position. At the completion of the autoinjector's drug-extrusion cycle, the insertion drive moves the drive post 268 and, therefore, the inner sleeve 220 containing the spent drug container back to the needle-concealed position where the drive post 268 is again latched between the latch arms 280a of the latch mechanism 280.

Referring now to FIGS. 6A-6D, various other embodiments of the cassette may further comprise an inner sleeve locking arrangement 290, which prevents the inner sleeve 220 from being unintentionally moved within the outer housing 210 from the needle-concealed position. The inner sleeve locking arrangement 290 may replace the latch mechanism 280 or provide redundancy as in the embodiment shown in FIGS. 6A-6B.

The addition of the inner sleeve locking arrangement 290 provides redundancy and increases reliability of the latch mechanism 280, for example, to protect a user from harm, protect the cassette contents, or prevent misuse. The inner sleeve locking arrangement 290 provides improved resistance to motion or locking of the inner sleeve 220 during an impact caused, for example, by a free fall, transportation, and/or handling. Further, the inner sleeve locking arrangement 290 improves impact energy absorption to prevent damage to cassette components. Still further, the inner sleeve locking arrangement 290 provides improved retention of the inner sleeve 220 in the needle-concealed position during removal of the needle shield to prevent exposure of the injection needle to the environment outside the outer housing of the cassette 200. In addition, the inner sleeve locking arrangement 290 more accurately and repeatedly places the inner sleeve 220 in a position for interfacing with the autoinjector.

Figure 6C:
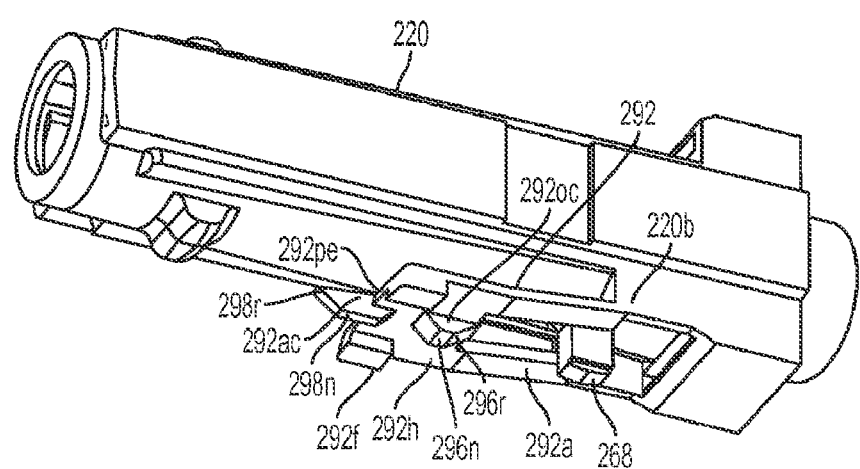
FIG. 6C is a bottom up front perspective view of an embodiment of an inner sleeve of the cassette shown in FIG. 3 showing certain elements of the inner sleeve latch mechanism and the inner sleeve locking arrangement.

As shown in FIG. 6C, various embodiments of the inner sleeve locking arrangement may comprise a cantilever lock arm 292, which is constructed to be unlocked by the insertion drive of the autoinjector. The cantilever lock arm 292 may comprise a hand member 292h and two flexible arm members 292a connecting the hand member 292h to a portion of the inner sleeve 220. The hand member 292h may include one or more locking feet, one or more opening cams, and one or more assembly cams. In the shown embodiment, the hand member 292h includes two locking feet 292f, one opening cam 292oc, and one assembly cam 292ac. The two locking feet 292 may be spaced apart from one another and disposed at or marginally adjacent to the leading or proximal edge 292pe of the hand member 292h. The opening cam 292oc may be disposed distal to the locking feet 292f and the assembly cam 292ac may extend proximally from the proximal edge 292pe of the hand member 292h. In the shown embodiment, the cantilever lock arm 292 extends from a marginally distal, bottom portion 220b of the inner sleeve, or any other portion of the sleeve which is capable of interfacing with the autoinjector's insertion drive.

As shown in FIG. 6B, various embodiments of the inner sleeve locking arrangement 290 may further comprise one or more locking feet receiving slots 294 provided in the bottom wall 210b of the cassette outer housing 210, or any other wall of the housing that interfaces with the cantilever lock arm 292 of the inner sleeve 220. Each of the one or more locking feet receiving slots 294 may be provided at the ends of a pair of elongated slots 282, which define the latch arms 280a of the latch mechanism 280. Each of the locking feet receiving slots 294 is operative for receiving a corresponding one of the locking feet 292f of the cantilever locking arm 292 to effect locking of the inner sleeve locking arrangement 290.

Figure 6D:
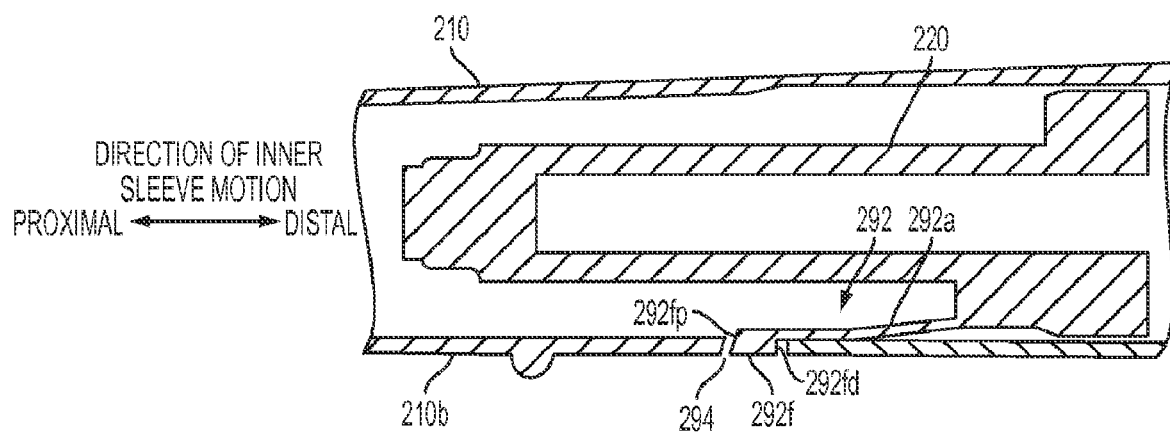
FIG. 6D is a sectional side view of the cassette of FIG. 6A, showing the operation of a locking foot of the inner sleeve locking arrangement.

As shown in FIG. 6D, various embodiments of the locking foot/feet 292f may comprise proximal and/or distal faces 292fp and 292fd, respectively. The proximal and/or distal faces 292fp, 292fd can be disposed at an angle, which is generally 90 degrees, less than 90 degrees (angled forward), or greater than 90 degrees (angled back), relative to the wall of the cassette outer housing 210 defining the locking feet receiving slots 294, to facilitate locking of the inner sleeve locking arrangement. The corresponding surfaces of the locking feet receiving slot 294, which engage the proximal and distal faces 292fp, 292fd of the locking feet 292f, may be constructed with angles that are complimentary to the angles of the proximal and distal faces 292fp, 292fd of the locking feet 292f. When the proximal face 292fp of the locking foot 292f is angled back as shown in FIG. 6D, and the inner sleeve 220 is forced proximally against the cantilever lock arm 292, the locking foot 292 may be drawn deeper into receiving slot 292 of the outer cassette housing wall resulting in a bias toward self-locking. Accordingly, the cantilever lock arm 292 can provide a locking force that is high relative to the force required to unlock it. In various other embodiments, the proximal and/or distal faces 292fp, 292fd of the locking feet 292f can be angled forward, which may aid in the assembly of the inner sleeve 220 to the outer housing 210. The flexible arm member(s) 292a of the cantilever lock arm 292 may apply a biasing force, which hold each locking foot 292f in their corresponding receiving slot 294 in the cassette outer housing wall 210b. In other embodiments, the flexible arm member(s) 292a of the cantilever lock arm 292 may not apply a biasing force to hold each locking foot 292f in their corresponding receiving slot 294 in the cassette outer housing wall 210b. The flexible arm members 292a can bend to disengage the locking feet 292f from their receiving slots 294.

Referring to FIG. 6C, in various embodiments, the opening cam 292oc may be disposed distal to the locking feet 292f so that it bends the cantilever lock arm 292 away from the cassette outer housing during the insertion cycle of the autoinjector. The bending of the cantilever lock arm 292 disengages the locking foot/feet 292f from the receiving slot(s) 294 in the outer housing and prevents them from contacting and sliding on the outer housing, thereby allowing the inner sleeve 220 to move freely without interference from the cantilever lock arm 292 during the insertion cycle. Various embodiments of the opening cam 292oc may comprise a male-shape member having a distal ramp face 296r that merges with a nose face 296n. The distal ramp face 296r may be angled back (e.g. where the angle of the distal ramp face 296r may be less than 270 degrees and greater than 180 degrees relative to the nose face 296n) where it is engaged by the autoinjector's insertion drive, as will be explained further on. In other embodiments, the opening cam 292oc may be configured as a female member.

Referring still to FIG. 6C, various embodiments of the assembly cam 292ac may extend proximally from the proximal edge 292pe of the hand member 292h so that it can bend the cantilever lock arm 292 away from the cassette outer housing wall 210b as the inner sleeve 220 is inserted into the outer housing 210 during cassette assembly. Various embodiments of the assembly cam 292ac may comprise a male-shape member having a proximal ramp face 298r that merges with a nose face 298n. The proximal ramp face 298r may be angled back (e.g. where the angle of the proximal ramp face 298r may be less than 270 degrees and greater than 180 degrees relative to the nose face 298n) where it contacts the distal edge of the outer housing bottom wall 210b when the inner sleeve 220 is inserted therein during assembly of the cassette 200. In other embodiments, the assembly cam 292ac may be configured as a female member.

It should be understood that in various other embodiments, the components of the inner sleeve locking arrangement shown as part of the outer housing in FIG. 6B can be provided on the inner sleeve, and the components of the inner sleeve locking arrangement shown as part of the inner sleeve in FIG. 6C, can be provided on the outer housing. In various other embodiments, the number of locking feet, slots, arm members, and/or cams can be more or less than described above. In still various other embodiments, the cantilever lock arm opening cam can be provided on the insertion rack of the autoinjector's insertion drive.

Figure 7A:
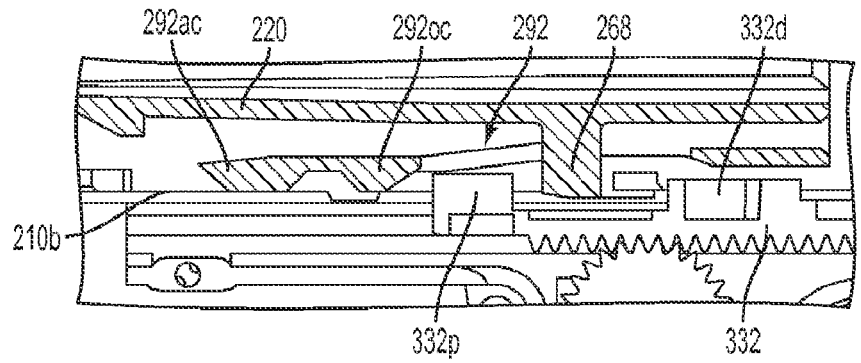
FIGS. 7A-7E are internal side views of the cassette of FIG. 6A showing the operation of an opening cam of the inner sleeve locking arrangement.

Referring to FIGS. 7A-7E, various embodiments of the inner sleeve locking arrangement may operate in the following manner during the insertion cycle of the autoinjector. FIG. 7A shows the cantilever lock arm 292 after the autoinjector door containing the cassette has just closed. As shown, the opening cam 292oc of the lock arm 292 may be proximally spaced from a proximal tab 332p of the autoinjector insertion rack 332, such that the inner sleeve locking arrangement is in the locked position (i.e., the locking foot/feet of the cantilever arm are engaged with their corresponding receiving slot(s) in the cassette outer housing wall as shown in FIG. 6D). In addition, when the cassette is loaded and the door is closed, the autoinjector will move the rack 332 so that the drive post 268 of the inner sleeve 220 is placed between proximal tab 332p and distal tab 332d.

Figure 7B:
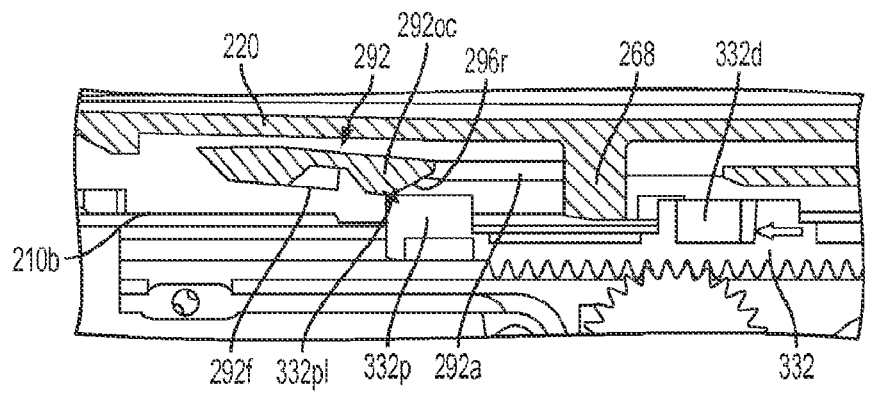

FIG. 7B shows the operation of the opening cam 292oc of the cantilever lock arm 292 after the insertion cycle of the autoinjector has just commenced. As shown, the proximal tab 332p of the insertion rack 332 has moved proximally to engage the distal ramp face 296r of the opening cam 292oc, which bends the arms 292a of cantilever lock arm 292 and lifts the lock arm 292 toward the inner sleeve 220, thereby disengaging the locking foot/feet 292f from the receiving slot(s) (not visible) in the outer housing bottom wall 210b. As also shown, the distal tab 332d of the insertion rack 332 has not engaged the drive post 268 of the inner sleeve 220, however, the resilient arms 280a of the latch mechanism 280 are about to be unlatched by distal tab 332d of the insertion rack 332.

Figure 7C:
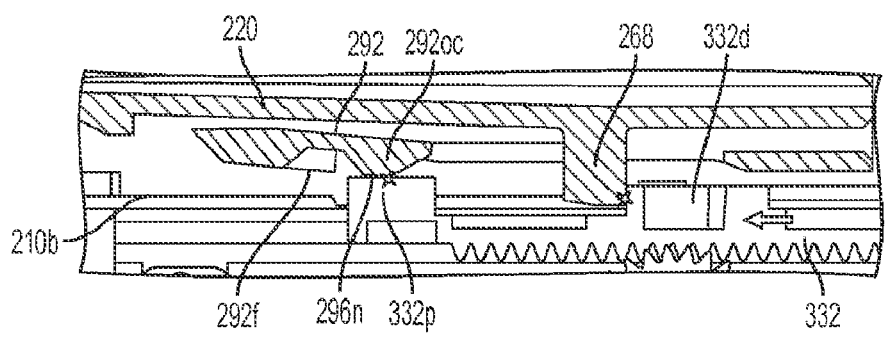

FIG. 7C shows the operation of the opening cam 292oc of the cantilever lock arm 292 after the proximal tab 332p of the insertion rack 332 has moved further proximally. As shown, the proximal tab 332p of the insertion rack 332 has slid under the operating cam 292oc and is engaged with its nose face 296n, which fully lifts the cantilever lock arm 292 toward the inner sleeve 220 and, therefore, the locking foot/feet 292f, so they disengage from the receiving slots (not visible) in the outer housing bottom wall 210b. Further, the distal tab 332d of the insertion rack 332 has moved proximally and has opened the arms 280a of the latch mechanism 280, thereby unlatching the drive post 268 of the inner sleeve 220 from the latch mechanism 280. The distal tab 332d then engages the drive post 268.

Figure 7D:
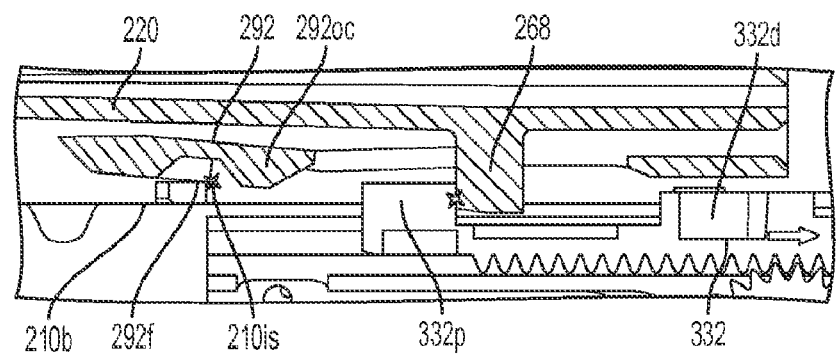

FIG. 7D shows the cantilever arm 292 after needle insertion has been completed and the needle retraction has begun. As shown, the proximal tab 332p of the insertion rack 332 has moved distally, thereby sliding off the opening cam 292oc of the lock arm 292 and has engaged the drive post 268 of the inner sleeve 220. Because the proximal tab 332p of the insertion rack no longer engages the opening cam 292oc, and is moving the drive post 268 distally, the arms 292a of the cantilever arm 292 bias it down toward the cassette outer housing wall 210b, thereby allowing the locking foot/feet 292f of the lock arm 292 to slide against the interior surface 210is of cassette outer housing bottom wall 210b while holding the assembly cam 292ac off the interior surface of the cassette outer housing wall 210b, as the inner sleeve 220 is driven back to the distal, needle-concealed position in the housing 210.

Figure 7E:
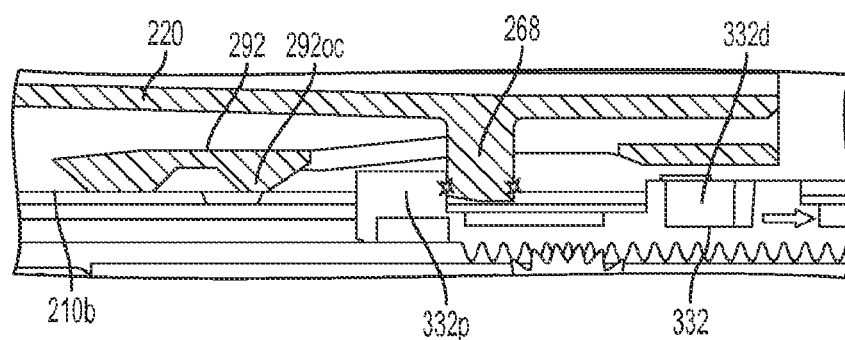

FIG. 7E shows the cantilever lock arm 292 after the locking foot/feet have lockingly engaged their corresponding receiving slots 294 (not visible), thereby placing the inner sleeve locking arrangement back in the locked position and re-latching the drive post 268 of the inner sleeve 220 in the latch mechanism (not visible).

Figure 8A:
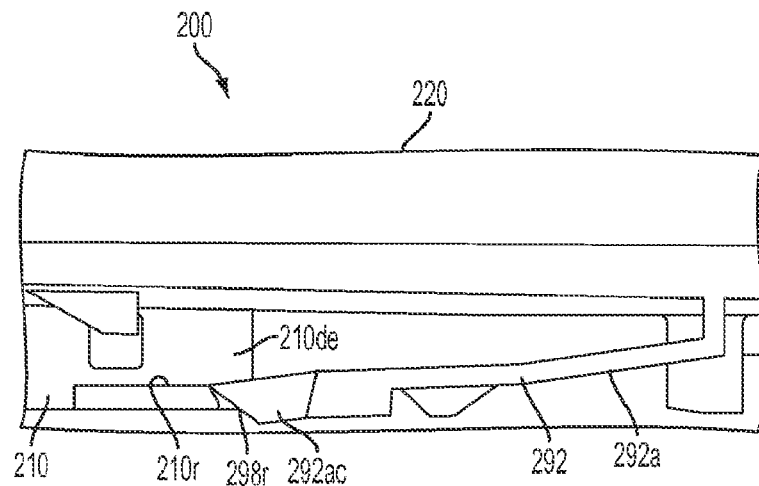
FIGS. 8A and 8B are internal side view of the cassette of FIG. 6A showing the operation of an assembly cam of the inner sleeve locking arrangement.

Various embodiments of the inner sleeve locking arrangement may operate to facilitate the assembly of the cassette 200, as will now be described with reference to FIGS. 8A and 8B. FIG. 8A shows the cantilever lock arm 292 as the inner sleeve 220 is first being inserted into the distal open end 210de of the outer cassette housing 210 during assembly of the cassette 200. As shown, the cantilever lock arm 292 is in a fully down position with the arms 292a relaxed in neutral, unbiased position, and the angled back proximal ramp surface 298p of the assembly cam 292ac is contacting a lift ramp 210r just inside the distal open end 210de of the cassette outer housing 210.

Figure 8B:
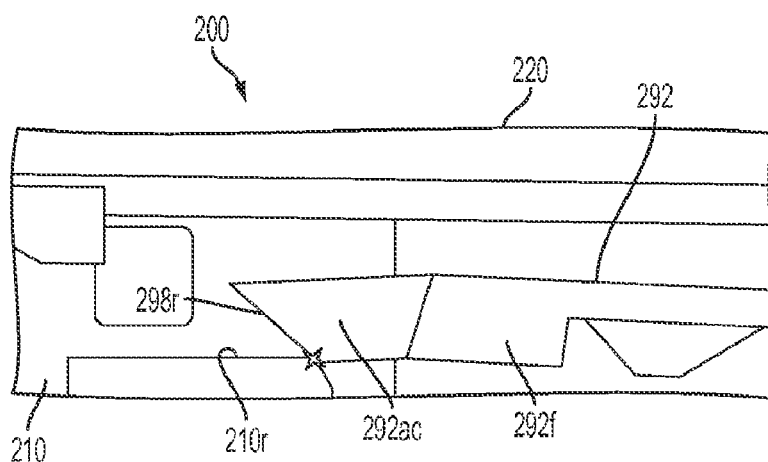

FIG. 8B shows the cantilever lock arm 292 after the inner sleeve 220 has been inserted further into the cassette outer housing 210. As shown, the assembly cam 292ac has slid up onto the lift ramp 210r of the cassette outer housing 210 facilitated by the angled back proximal ramp face 298r, thereby bending the arms (not visible) of the lock arm 292 and lifting it toward the inner sleeve 220. The lifting of the cantilever lock arm 292 prevents the locking foot/feet 292f from contacting and thus, interfering with the cassette outer housing 210 as the inner sleeve 220 is fully inserted into cassette outer housing 210.

In the above-described embodiments, the inner sleeve locking arrangement provides inner sleeve locking when the cantilever lock arm is in an unbiased state. In various other embodiments, the cantilever lock arm of the inner sleeve locking arrangement can be constructed to provide inner sleeve locking in a biased, actuated position. Such embodiments may be desirable, for example, to hold the inner sleeve and thus, the drug container, in a fixed position at a desired time. In addition, because the motor of the insertion drives the sleeve containing the drug container, the depth of the injection needle can be controlled. This feature can be used in conjunction with the locking feet receiving slots and/or with cassette identification arrangement described further on.

Figure 9A:
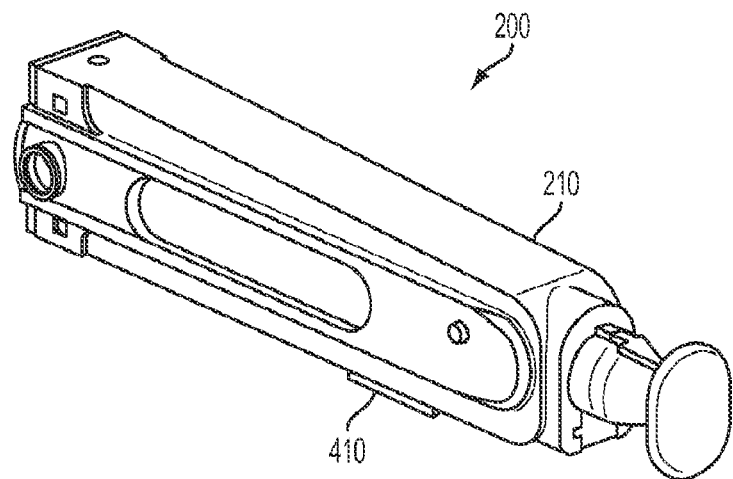
FIGS. 9A and 9B are top down and bottom down front perspective views, respectively, of an embodiment of the cassette with a cassette identification arrangement.
Figure 9B:
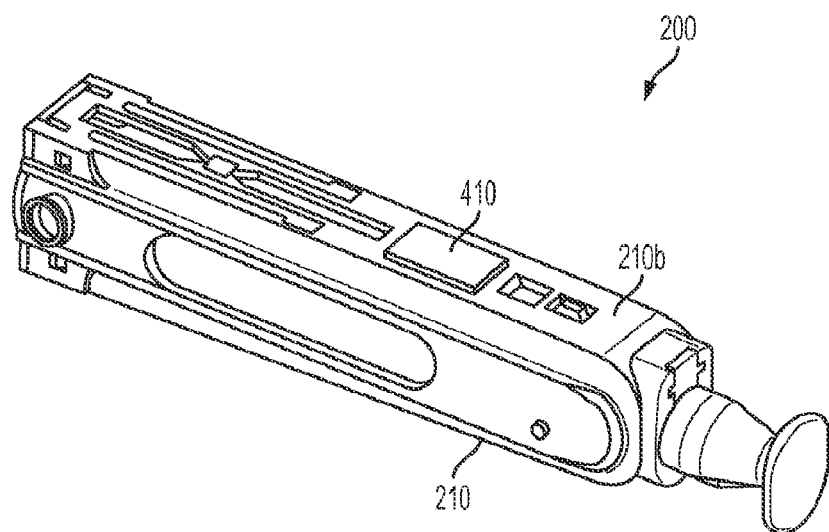

Referring collectively now to FIGS. 9A and 9B, various embodiments of the cassette 200 may further comprise a cassette identification arrangement 410, which may be constructed to communicate information about the cassette 200 to the autoinjector. The cassette identification arrangement 410 may be provided on an exterior surface of the bottom wall 210bs of the cassette outer housing 210 or any other portion of the cassette 200 that is capable of being detected and interpreted by the autoinjector. In some embodiments the information communicated by the cassette identification arrangement 410 may be in the form of a code. Specifically, the cassette identification arrangement 410 may be constructed to generate one of a plurality of different codes, each of which corresponds to certain characteristics of a particular cassette 200. The code allows a suitably adapted autoinjector to determine the type of cassette 200 inserted into the autoinjector, i.e, whether the cassette is a training cassette (i.e., contains no drug receptacle or contains an empty drug receptacle) or a drug cassette containing the drug container prefilled with a drug. Further, the code communicated by the cassette identification arrangement 410 can tell the autoinjector what the drug contained in the drug receptacle is and/or other cassette/drug container characteristics. Still further, the code may provide information that allows the autoinjector to determine, whether the cassette 200 has been inserted into the autoinjector in the proper orientation. The autoinjector can be constructed to automatically select an appropriate operating program and/or adjust its various operational parameters based on the information communicated by the cassette identification arrangement 410 (e.g., with a microprocessor as described earlier). For example, if the autoinjector detects the insertion of a training cassette, the autoinjector can automatically select a training program to train the user on the use of the autoinjector. In another example, if the autoinjector detects the insertion of a drug cassette that contains a drug container prefilled with a certain drug, the autoinjector can automatically select appropriate operating parameters for injecting that drug, such as injection speed, needle insertion speed, pre and post-injection wait time, needle insertion depth, temperature limits, etc. Available speed ranges may be dependent upon the drug container fill volume and drug characteristics, such as viscosity. Automatic selection by the autoinjector of its operating parameters eliminates the need for the user to have to determine the appropriate operating parameters for a given drug and then manually input them into the autoinjector.

Figure 10A:
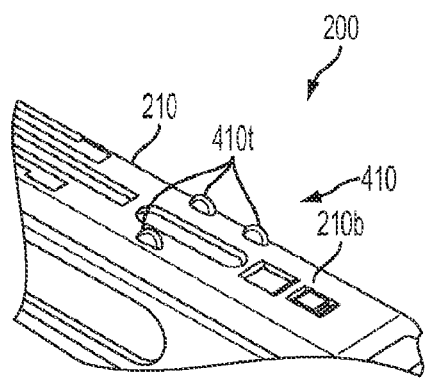
FIG. 10A is a bottom down perspective view of a portion of the cassette showing an embodiment of the cassette identification arrangement.
Figure 10B:
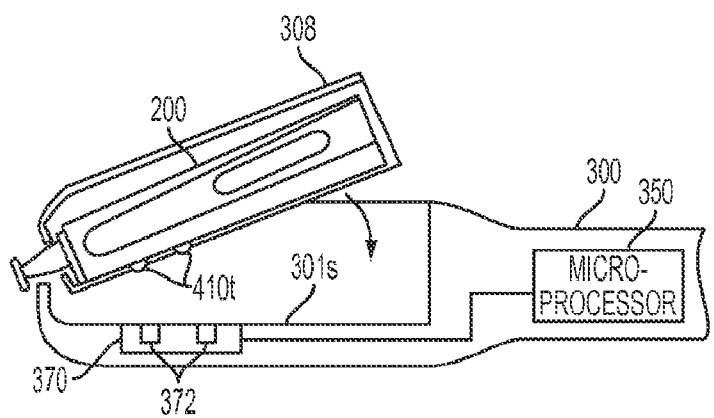
FIG. 10B is a sectional side view of the cassette of FIG. 10A being inserted into an autoinjector constructed to detect and decipher the cassette identification arrangement embodied in FIG. 10A.

As shown in FIG. 10A, various embodiments of the cassette identification arrangement 410 may comprise one or more projections or tabs 410t provided on or in the bottom wall 210b of the cassette outer housing 210. The number and location of the tabs 410t may define the code or at least a portion of the code, which represents information about the cassette 200. As shown in FIG. 8B, the cassette identification arrangement 410 may further comprise a detector 370 that may be provided on or in the cassette support surface 301s of the autoinjector 300 to sense the number and location of the tabs 410t when the cassette 200 engages the cassette support surface 301s as the autoinjector door 308 is closed. The detector 370 may be communicatively coupled to a microprocessor 350 contained within the autoinjector 300, thereby enabling the autoinjector 300 to detect the tabs 410t and obtain the code representing the information about the cassette 200. In various embodiments, the detector 370 may comprise a plurality of conventional, flat-flush mounted, momentary, push-button switches 372. The switches 372 may be arranged to engage corresponding ones of the tabs 410t. None, some, or all of the switches 372 may be actuated by the tabs 410t of the cassette 200, depending upon the arrangement of tabs 410t and the code they represent, when the cassette 200 is supported on the cassette support surface 301s of the autoinjector 300. Therefore, the code defined by the tabs 410t and the information that the code represents about the cassette 200 can be communicated to the microprocessor 350 of the autoinjector 300 for deciphering.

The tabs 410t can be differentiated from each other by their individual location on or in the cassette housing 210. By utilizing the presence or absence of tabs 410t, multiple combination codes can be created such that each code identifies a particular cassette 200 or characteristics of the cassette. Although the cassette identification arrangement 410 shown in the embodiment of FIG. 8A comprises three tabs 410t, various other embodiments of the cassette identification arrangement 410 may comprise more or less than three tabs in order to increase or decrease the number of programming codes available. In the embodiment shown in FIG. 8A, the presence and/or absence of one or more of the three tabs 410t provides up to eight (8) different possible cassette identification codes, which can be detected and deciphered by the autoinjector 300. As mentioned earlier, the information represented by each code can be used to define one of a plurality of programming instructions for the autoinjector 300 and/or to communicate secondary information to the autoinjector 300, such as, but not limited to, verifying that the cassette 200 is an authorized OEM device, and/or verifying the proper insertion of the cassette 200 into the autoinjector 300.

Various other embodiments of the tabs 410t of the cassette identification arrangement 410 may have different heights. In such embodiments, the autoinjector's push-button switches 372 and microprocessor 350 can be constructed to allow them to differentiate between tabs 410t of the different heights, for example, but not limitation, by how far in a button (not shown) of the push-button switch 372 is depressed into the switch 370 by the tab 410t. Embodiments comprising both short and tall tabs 410t can provide each possible tab location on the cassette outer housing 210 with one of three possible states, e.g.:

State 1: no tab present
State 2: short tab present
State 3: tall tab present

If the cassette identification arrangement 410 comprises, for example, up to three tabs 410t where each such tab 410t is short or tall, the autoinjector could detect up to twenty-seven (27) different tab states to increase the number of possible codes.

Figure 11A:
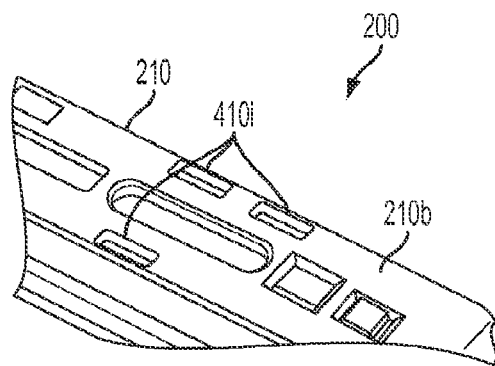
FIG. 11A is a bottom down perspective view of a portion of the cassette showing another embodiment of the cassette identification arrangement.
Figure 11B:
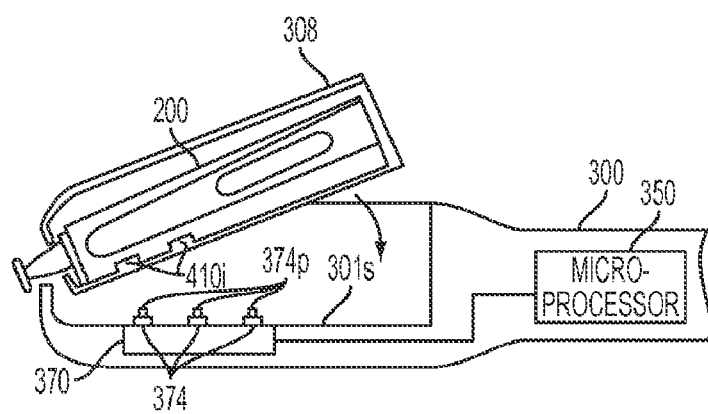
FIG. 11B is a sectional side view of the cassette of FIG. 11A being inserted into an autoinjector constructed to detect and decipher the cassette identification arrangement embodied in FIG. 11A.

As shown in FIG. 11A various other embodiments of the cassette identification arrangement 410 may comprise one or more indentations 410i provided in the bottom wall 210b of the outer housing 210 of the cassette 200. As shown in FIG. 11B, in such embodiments of the cassette identification arrangement 410, the detector 370 of the autoinjector 300 may comprise a plurality of conventional pogo-pin switches 374n to detect the presence or absence of the indentations 410i. The coding, detection, deciphering, and parameter control functions are generally the same as described above with respect to the tabs 410t.

Various other embodiments of the indentations 410i of the cassette identification arrangement 410 can have different depths. In such embodiments, the autoinjector's pogo-pin switches 374 and microprocessor 350 can be constructed to allow them to differentiate between indentations of the different depths by how far in a pin 374p of the pogo-pin switch 374 is depressed into the switch by the indentation, to increase the number of possible different codes.

In various further embodiments, the cassette identification arrangement 410 of the cassette may comprise a combination of the above-described tabs 410t and indentations 410i. The autoinjector, in such embodiments may then be constructed to include corresponding push-button and pogo-pin switches 372, 374.

The codes defined by the tabs 410t and/or indentations 410t of the cassette identification arrangement 410 communicate information about the cassette 200 to the autoinjector 300, which can then use this information to automatically adjust its programming, etc. For example, but not limitation, one tab 410t or indentation 410i may define a code that indicates that the cassette 200 contains a drug container filled with 1 mL of a drug and two tabs 410t or indentations 410i may define a code that indicates that the cassette 200 contains a drug container filled with 0.5 mL of a drug. An additional tab 410t or indentation 410i in the same cassette identification arrangement may provide a code that identifies the drug and/or characteristics of the drug. In another example, the code for a training cassette may comprise the presence of all the possible tabs 410t and/or indentations 410i. In a further example, the absence of one of the tabs 4105t and/or indentations 410i may define a code for a certain drug. Different combinations of tabs 410t and/or indentations 410i can be used to differentiate between different drugs or to indicate the absence of the drug container, for the purpose of controlling the autoinjector parameters.

Figure 12A:
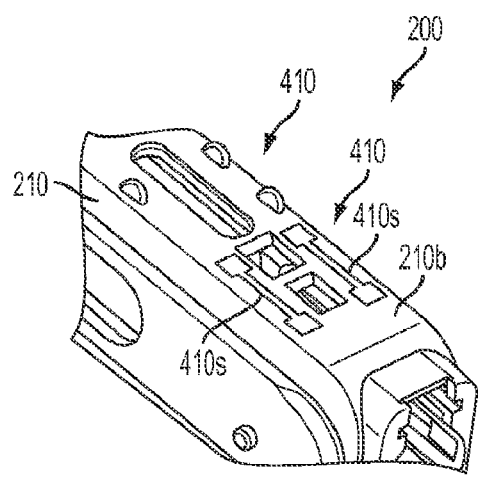
FIG. 12A is a bottom down front perspective view of a portion of the cassette showing another embodiment of the cassette identification arrangement.
Figure 12B:
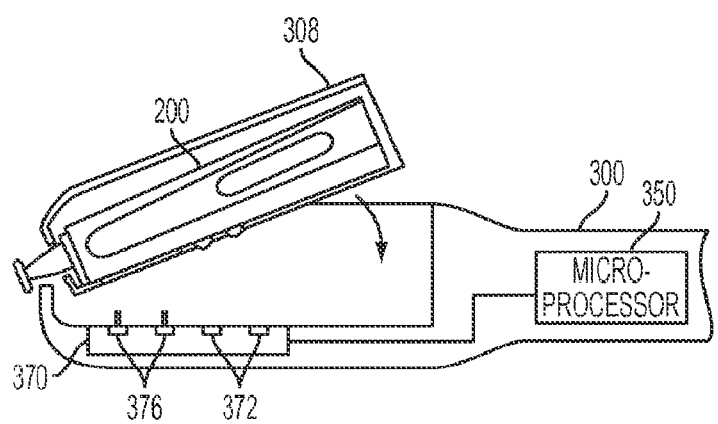
FIG. 12B is a sectional side view of the cassette of FIG. 12A being inserted into an autoinjector constructed to detect and decipher the cassette identification arrangement embodied in FIG. 12A.

As shown in FIG. 12A, various other embodiments of the cassette identification arrangement 410 may comprise one or more flat, electrically conductive traces or strips 410s provided on the outer surface of the bottom wall 210b of the outer housing 210. In such embodiments of the cassette identification arrangement 410, as shown in FIG. 12B, the detector 370 of the autoinjector 300 can be constructed with pogo-pin connectors 376 that contact the conductive strips 410s when the cassette 200 is inserted into the autoinjector 300. The conductive strips 410s can be molded into the exterior surface of the cassette's bottom wall 210b, screen-printed onto that surface, or comprise a separate component, such as a flex-cable material, affixed to that surface with pressure sensitive adhesive or any other suitable means.

In various embodiments, the one or more conductive strips 410s can be operative as a cassette presence sensor, where each of the conductive strip 410s may operate to close an electrical circuit of the detector 370 between two pogo-pin connectors 376 when the cassette 200 is mounted on the support surface 301s of the autoinjector 300. In some embodiments, the conductive strips 410s can be constructed to form a straight path (e.g., as show in FIG. 12A) to connect inline arranged pogo-pin connectors, or constructed to form a tortuous path to connect pogo-pin connectors that require jagged or tortuous path to connect. In other embodiments, the conductive strips 410s can be constructed to have a specific electrical resistance, capacitance, inductance, etc, which would define a code capable of detection via the electrical circuit of the detector 370, which in turn would communicate the code and, therefore, the associated cassette information to the microprocessor 350 of autoinjector 300, such as drug, fill volume, injection speed, etc.

As further shown in FIGS. 12A and 12B, various embodiments of the cassette identification arrangement 410 may combine the one or more conductive strips 410s with the one or more tabs 410t (and/or indentions 410i) described earlier. In such embodiments of the cassette identification arrangement 410, the detector 370 and microprocessor 350 of the autoinjector 300 can be constructed to have the appropriate push-button switches 372 and pogo-pin switches 374 (and/or pogo-pin connectors 376). It should be understood, however, that the cassette identification arrangement 410 may only comprise the one or more conductive strips 410s.

Figure 13A:
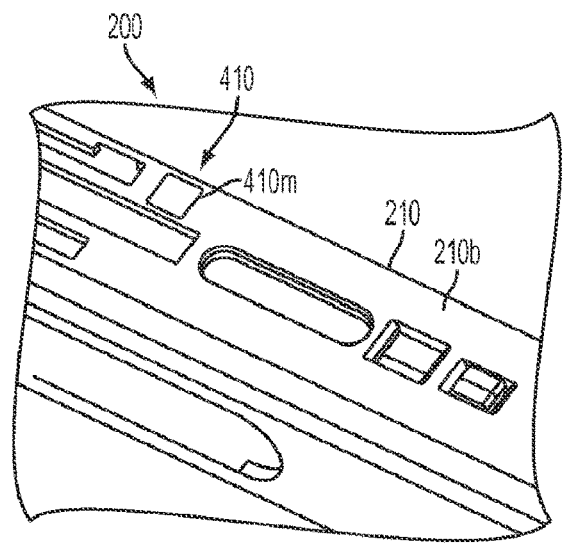
FIG. 13A is a bottom down perspective view of a portion of the cassette showing a further embodiment of the cassette identification arrangement.

As shown in FIG. 13A, various other embodiments of the cassette identification arrangement 410 may comprise one or more magnets 410m embedded in the bottom wall 210b of the cassette outer housing 210 or provided on the exterior or interior surface of the bottom wall 210b of the cassette outer housing 210. In such embodiments of the cassette identification arrangement 410, the detector 370 of the autoinjector 300 (e.g., FIGS. 10B-12B) can be constructed as a Magnetic Resonance (MR) sensor or other magnetic-sensing sensor that is activated by the one or more magnets when the cassette 200 is inserted into the autoinjector 300. The one or more magnets 410m should be of sufficient strength to activate the MR sensor. The magnet and MR sensor arrangement can be used alone or combined with any of the other previously described cassette identification arrangements 410.

Figure 13B:
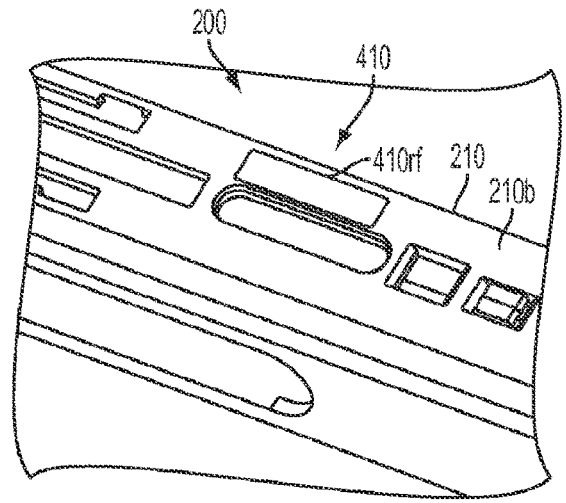
FIG. 13B is a bottom down perspective view of a portion of the cassette showing still another embodiment of the cassette identification arrangement.

As shown in FIG. 13B, various further embodiments of the cassette identification arrangement 410 may comprise a radio-frequency (RF) electromagnetic field (EMF) emitting device 410rf, such as RF identification (RFID) chip. The detector 370 of the autoinjector 300 (e.g., FIGS. 10B-12B) can be constructed as an EMF receiving device, such as an RFID chip reader, that is activated by the RF EMF device 410rf when the cassette 200 is inserted into the autoinjector 300. The RF EMF device 410rf can be molded into or attached to the bottom wall 210b of cassette outer housing 210 or any other suitable portion of the cassette 200 that allows the RF EMF device 410rf to communicate with the detector 370 of the autoinjector 300.

Figure 13C:
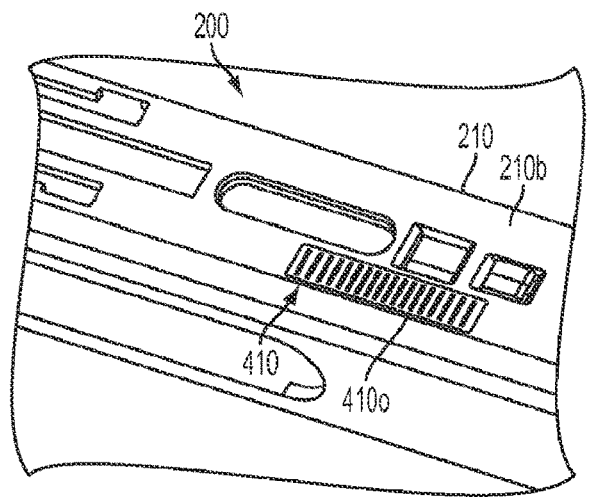
FIG. 13C is a bottom down perspective view of a portion of the cassette showing yet another embodiment of the cassette identification arrangement.

As shown in FIG. 13C, various other embodiments of the cassette identification arrangement 410 may comprise one or more optical machine-readable (OMR) identifiers 410o. The one or more OMR identifiers 410o may comprise, without limitation, one or more bar-code labels, one or more color-coded labels, one or more other suitable OMR identifiers, or any combination thereof. OMR identifiers 410o embodied as bar-code labels may comprise, but arc not limited to, 1-dimensional and 2-dimensional matrix codes. The detector 370 of the autoinjector 300 (e.g., FIGS. 10B-12B), in such embodiments, can be constructed as an optical scanner. The OMR identifier 410o may be provided on the exterior surface of the bottom wall 210b of the cassette's outer housing 210 or any other suitable portion or area of the cassette 200 that is capable of interfacing with the detector 370 of the autoinjector 300.

The RF EMF device 410rf and one or more OMR identifier labels 410o can be applied to the cassette before or after it is assembled with the prefilled drug container. This allows the RF EMF device 410rf and/or one or more OMR identifier labels 410o to include additional information or programming, such as the date of manufacture, location of manufacture, expiration date of drug, drug temperature stabilization time in order to allow the drug to reach an optimal temperature prior to injection), and autoinjector verification that the cassette 200 and drug are OEM components.

Figure 13D:
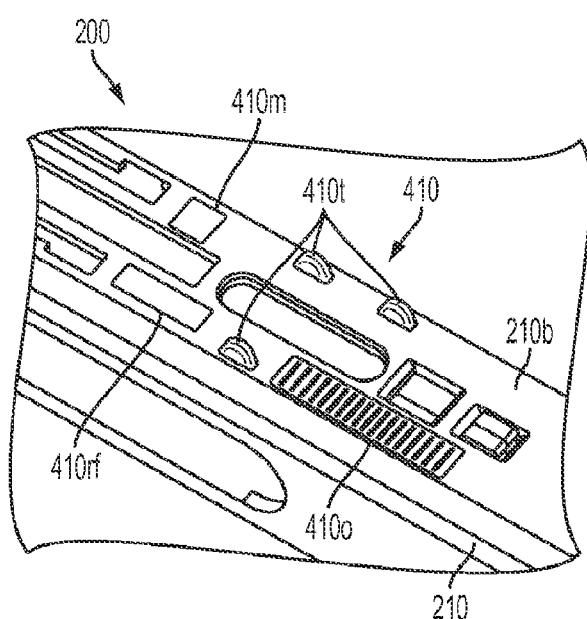
FIG. 13D is a bottom down perspective view of a portion of the cassette showing another embodiment of the cassette identification arrangement.

As shown in FIG. 13D, various other embodiments of the cassette identification arrangement 410 may comprise the one or more magnets 410m, the RF EMF emitter device 410rf, the one or more OMR identifiers 410o and the tabs 410t (and/or indentations 410i) described earlier, each defining a portion of the code provided by the arrangement 410. In such embodiments of the cassette identification arrangement, the detector 370 of the autoinjector can be constructed with the appropriate switches, sensors, receivers, and/or scanners (e.g. FIGS. 10B-12B) to detect the corresponding cassette elements of the cassette identification arrangement 410.

Figure 14:
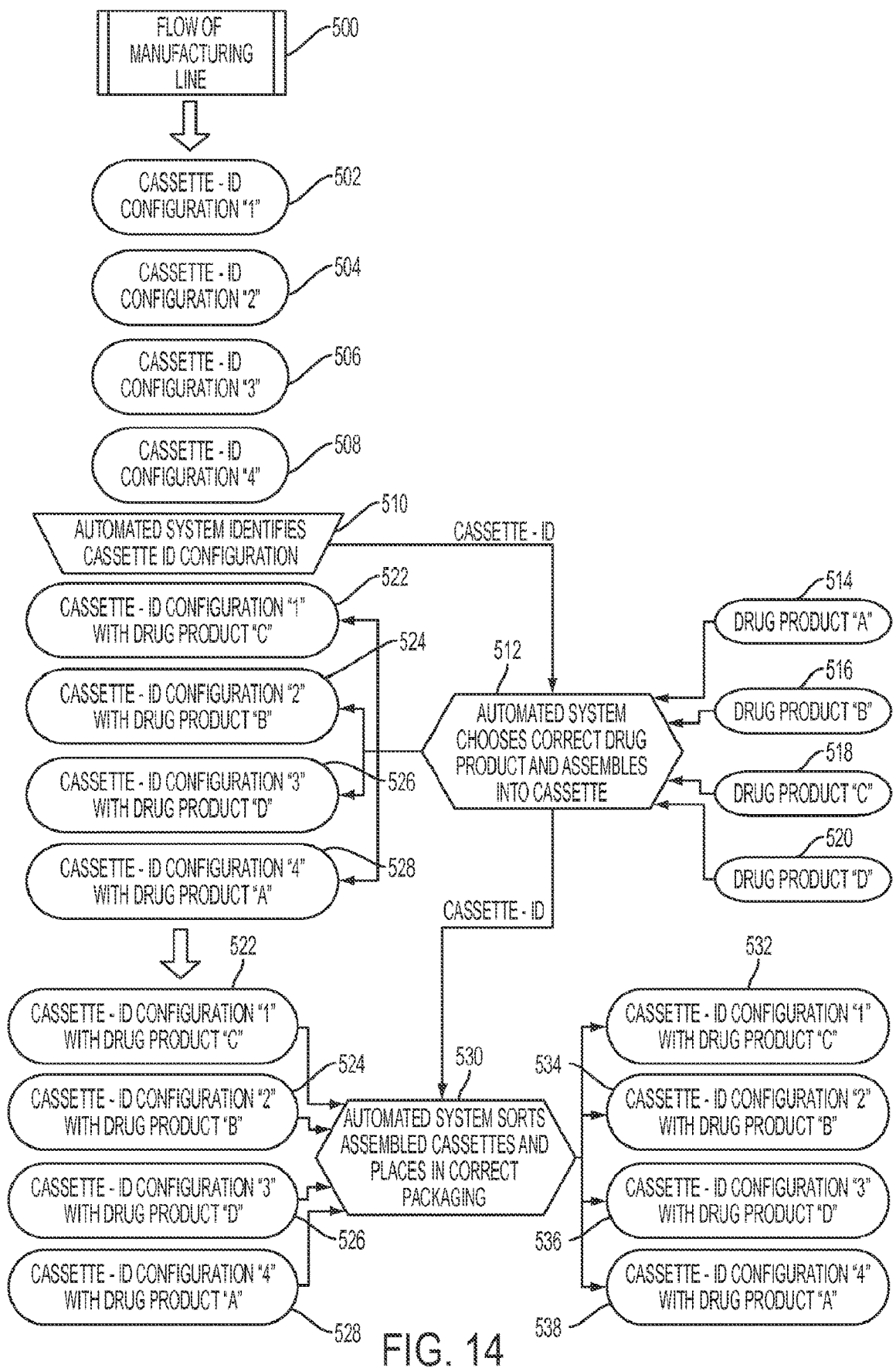
FIG. 14 is a flow chart showing an embodiment of a method for assembling different product lines on a single manufacturing line using the cassette identification arrangement to control the assembly of prefilled drug containers (containing a range of different drugs and/or fill levels) and to rout the assembled cassettes to the appropriate packaging stations.

The cassette identification arrangement 410 may also be used to control aspects of the cassette manufacturing and packaging processes. FIG. 14 shows a flow chart which shows an example of how a single production or manufacturing line may be used to assemble different product lines using the cassette identification arrangement to control the assembly of the prefilled drug containers (containing a range of different drugs and/or fill levels) and then rout the assembled cassettes to the appropriate packaging stations. Block 500 represents a single manufacturing line which may comprise a computer controlled manufacturing system and blocks 502, 504, 506, and 508 may represent four unassembled cassettes in the line each having it own cassette identification arrangement configuration (1, 2, 3, or 4) of tabs, indentations, etc. Each of the unassembled cassettes 502, 504, 506, and 508 are to be assembled with a drug container having one of four different drugs (A, B, C, or D) that matches the cassette identification arrangement configuration (cassette ID configuration). In the embodiment shown in FIG. 14, the manufacturing system may be programmed such that cassette ID configuration 1 identifies drug C, cassette ID configuration 2 identifies drug B, cassette ID configuration 3 identifies drug D, and cassette ID configuration identifies drug A.

In block 510, the manufacturing system of the line identifies the cassette ID configuration of each of the unassembled cassettes 502, 504, 506, and 508. For each of the unassembled cassettes 502, 504, 506, and 508, the system in block 512 selects a matching one of the drug containers 514, 516, 518, and 518 prefilled with drugs A, B, C, and D, respectively, using the identified cassette ID and assembles it with the unassembled cassette 502, 504, 506, and 508. Therefore, in block 512, unassembled cassette 502 with cassette ID configuration 1 may be assembled with drug container 518 prefilled with drug C to generate assembled cassette 522, unassembled cassette 504 with cassette ID configuration 2 may be assembled with drug container 516 prefilled with drug B to generate assembled cassette 524, unassembled cassette 506 with cassette ID configuration 3 may be assembled with drug container 520 prefilled with drug D to generate assembled cassette 526, and unassembled cassette 508 with cassette ID configuration 4 may be assembled with drug container 514 prefilled with drug A to generate assembled cassette 528.

In block 530, the manufacturing system sorts assembled cassettes 522, 524, 526, and 528 using their cassette ID configurations 1, 2, 3, and 4, respectively, and places them in packages 532, 534, 536, and 538 for drugs C, B, D, and A, respectively.

Figure 15A:
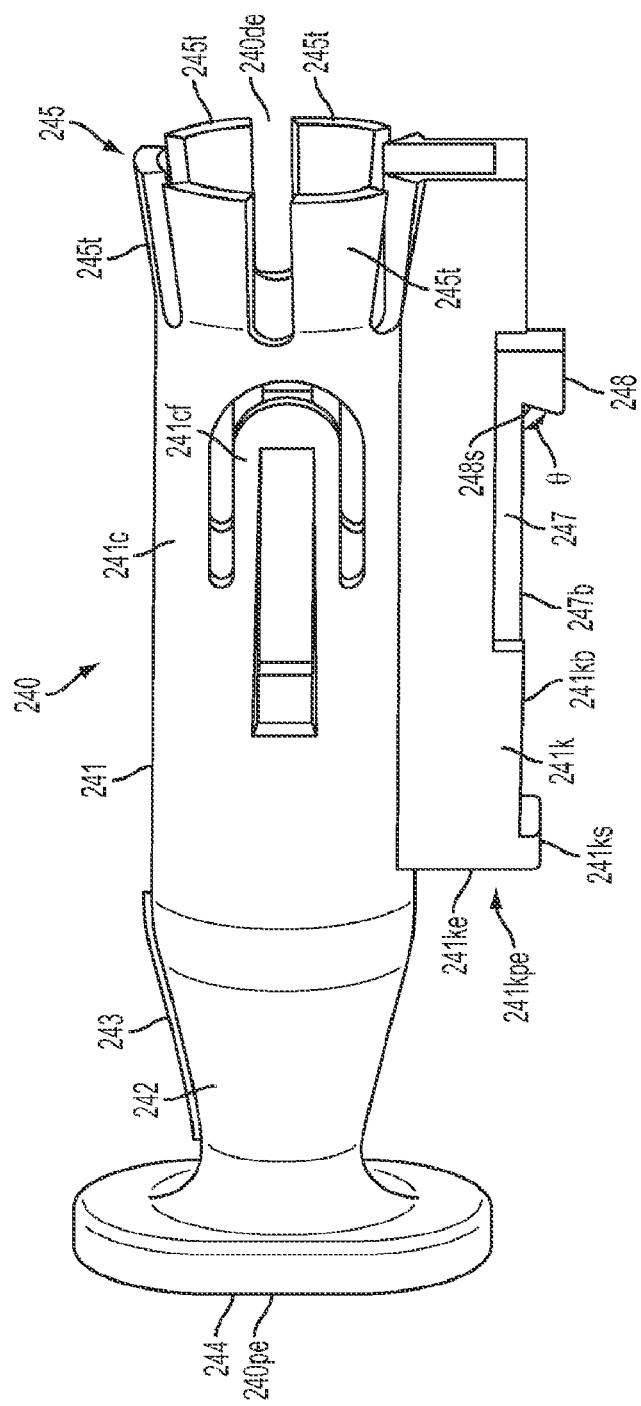
FIG. 15A is a perspective rear view of an embodiment of a cassette cap of the cassette.
Figure 15B:
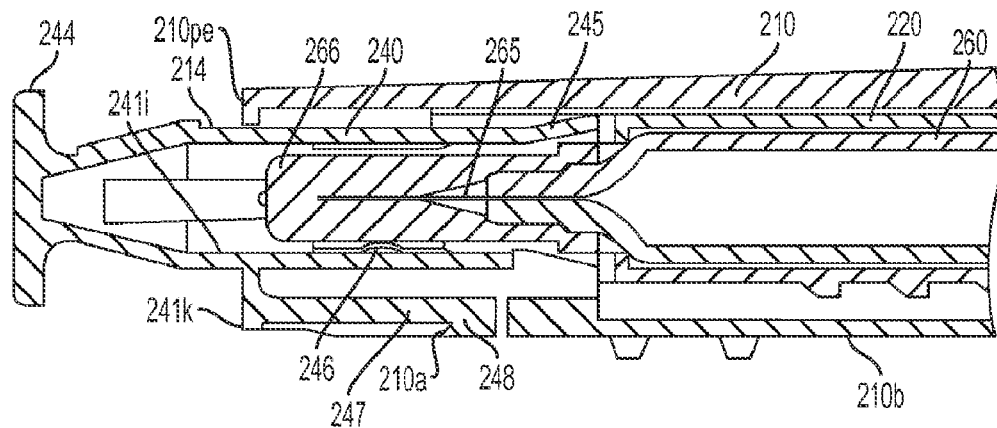
FIG. 15B is a sectional side view of the proximal end of a cassette showing the cassette cap of FIG. 15A coupled to a needle shield of a drug container provided in the cassette.

FIGS. 15A and 15B collectively show an embodiment of the cassette cap 240 of the cassette 200. The cassette cap 240 may function as a needle shield remover by engaging and gripping the needle shield 266 of the drug container 260 in a manner that allows the user to remove the needle shield 266 from the drug container 260, prior to operating the autoinjector. Further, the cassette cap 240 may lockingly engage the cassette outer housing 210 so that it cannot be easily withdrawn from the cassette 200 unless the cassette 200 is properly installed in the autoinjector. This prevents the needle shield 266 from being inadvertently removed from the drug container 260 when, for example, the cassette 200 is handled by the user. In addition, the presence of the shield remover 240 provides an indication that the cassette 200 has not been previously used or tampered with.

As shown in FIG. 15A, various embodiments of the cassette cap 240 may comprise a hollow body 241 formed by a generally cylindrical portion 241c and a generally rectangular, key portion (key) 241k disposed lateral to and merging with the cylindrical portion 241c. The cassette cap 240 may further comprise a tapered portion 242 that extends proximally from the cylindrical portion 241c of the body 241. An outwardly extending flange 244 terminates the tapered portion 242 and closes the cassette cap 240 at a proximal end 240pe thereof. The flange 244 may function as a finger gripping member that allows a user to grip and pull the cassette cap 240 out of the cassette 200 to remove the needle shield 266 from the drug container 260 after the cassette has been properly installed in the autoinjector. To facilitate gripping and pulling of the cassette cap 240, the flange 244 may have a generally oblong shape which is easily gripped by users with dexterity problems. An "arrow" icon 243 may be provided on the tapered portion 242 of the cassette cap 240 to indicate the proper direction and orientation for inserting the cassette into the cassette door of the autoinjector.

Figure 15C:
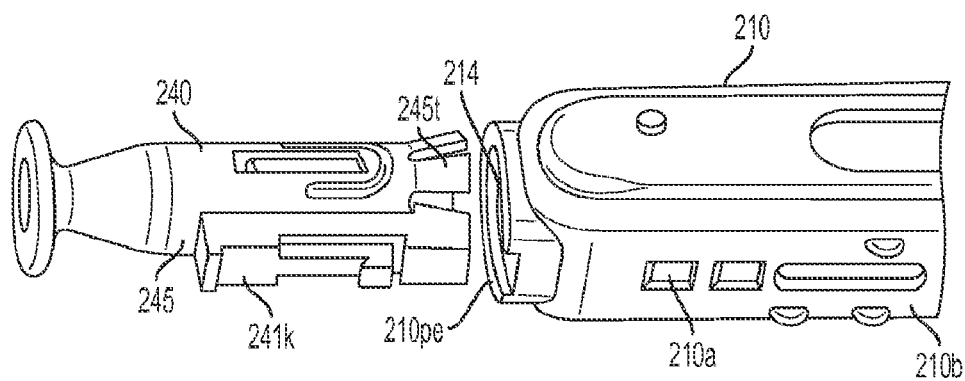
FIG. 15C is a bottom up front perspective view of a portion of the cassette with the cassette cap removed from the cassette.

The cylindrical portion 241c and the key 241k are open at a distal end 240de of the cassette cap 240. The open distal end of the cylindrical portion 241c may be formed by a plurality of flexible, outwardly flared tongues 245t that define an expandable collar structure 245, which merges with the open distal end of the key 241k. The expandable collar structure 245 prevents the cassette cap 240 from being reinserted into the cassette as shown in FIG. 15C. The cylindrical portion 241c may include flexible members 241cf that allow the cylindrical portion 241c to accept a metal insert 246 (FIG. 15B) that help engage and grip needle shield.

Referring again to FIG. 15A, the key 241k may include an end wall 241kc that closes the proximal end thereof. The end wall 241ke may extend slightly beyond a bottom wall 241kb of the key 241k, thereby forming a stop 241ks.

Figure 16A:
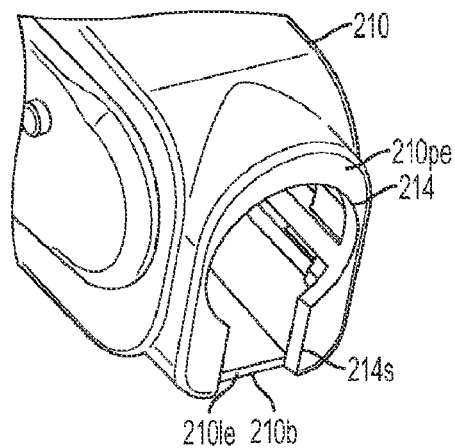
FIG. 16A is a top down front perspective view of a proximal portion of the outer housing of the cassette with the cassette cap removed, showing an embodiment of a slot for receiving a key portion of the cassette cap embodied in FIG. 15A.
Figure 16B:
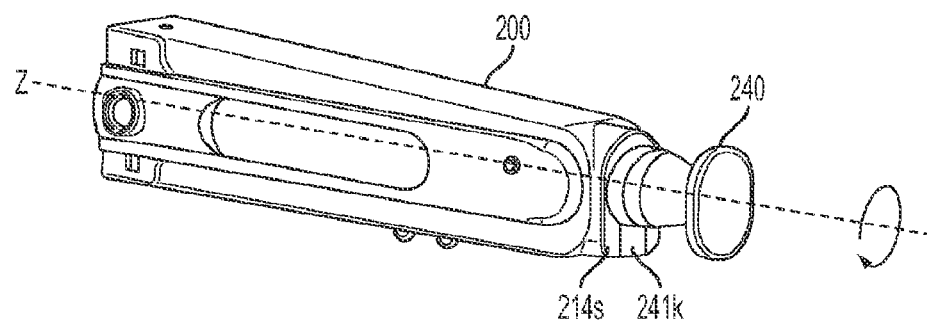
FIG. 16B is a top down front perspective view of the cassette showing how an anti-rotation structure formed by the slot of the outer housing and the key of the cassette cap prevents the cassette cap from being rotated or twisted around its longitudinal axis Z when the cassette cap is in the cassette (prior to needle shield removal) and thus, prevents rotation of the needle shield.

As shown in FIG. 16A, the proximal end wall 210pe of the cassette outer housing 210 may include a slot 214s that extends from the aperture 214 toward the bottom wall 210b of the housing 210. The slot 214s may be sized and shaped so that it mates with the key 241k of the cassette cap 240 with the leading edge 210le of the outer housing bottom wall 210b engaging the stop 241ks of the cassette cap key 241k, when the cassette cap 240 is in the cassette 200, thereby forming a cassette cap anti-rotation structure. As shown in FIG. 16B, the anti-rotation structure formed by the slot 214s and key 241k prevents the cassette cap 240 from being rotated or twisted around its longitudinal axis Z when the cassette cap 240 is in the cassette 200 (prior to needle shield removal) and thus, prevents rotation of the needle shield. This is important because rotation of the needle shield can result in cutting or coring of the needle shield by the sharp end of the injection needle. Accordingly, the anti-rotation structure protects the needle shield from being damaged by the injection needle when the cassette cap 240 is in the cassette 200. The stop 241ks of the cassette cap key 241k can limit cassette cap 240 from being pushed along the longitudinal axis Z distal towards the syringe, which also prevents the injection needle from penetrating and thereby damaging the needle shield.

Referring again to FIGS. 15A-15C, the bottom wall 241kb of the key 241k may define a cassette cap locking structure formed by a distally extending cantilever spring member 247 and a downwardly extending projection or lock tab 248 provided at the free end of the spring member 247. The lock tab 248 may comprise an undercut formed by an inclined surface 248s that defines an acute angle $\theta$ with the bottom surface 247b of the spring member 247.

As shown in FIGS. 15B and 15C, a metal tubular insert 246 may be provided on an interior surface 241i of the cylindrical body portion 241c for gripping the outer surface of the needle shield 266 so that it can be withdrawn with the cassette cap 240. In various other embodiments, the metal tubular insert 246 may be replaced by gripping teeth (not shown) formed on the interior surface 241i of the cylindrical body portion 241c. The cassette cap 240 may extend through the aperture 214 formed in the proximal end wall 210pe of the outer housing 210 of the cassette 200, which locates the flange or gripping member 244 of the cassette cap 240 outside of the cassette 200. The locking structure of the cassette cap 240, formed by the cantilever spring member 247 and lock tab 248, may be disposed within the marginal proximal portion of the outer cassette housing 210, such that it locks the cassette cap 240 in place in the cassette 200, in a tamper-resistant manner. Locking may be facilitated by the cantilever spring member 247, which forces or biases the tab 248 into a lock aperture 210a (FIG. 15C) that may be defined in the bottom wall 210b of the outer housing 210 of the cassette 200. The lock tab 248 engaged with the lock aperture 210a of the cassette outer housing 210, substantially prevents withdrawal of the cassette cap 240 from the cassette 200, unless the cassette 200 is properly installed within the autoinjector. Because the cassette cap 240 is attached to the needle shield 266 and locked within the cassette 200, the needle shield 266 may not be inadvertently removed from the syringe 260, prior to proper installation in the autoinjector. The presence of the cassette cap 240 also provides an indication that the cassette 200 has not been previously used or tampered with.

As shown in FIG. 15C, once the cassette cap 240 has been removed, the tongues 245t of the expandable partial collar structure 245 expand or spread outwardly to prevent the cassette cap 240 and the needle shield 266 attached thereto (not visible) from being re-inserted into the aperture 214 in the proximal end wall 210pe of the cassette outer housing 210. The absence of the cassette cap 240, therefore, provides an indication to the user that the cassette 200 has already been used or has been tampered with.

Figure 15D:
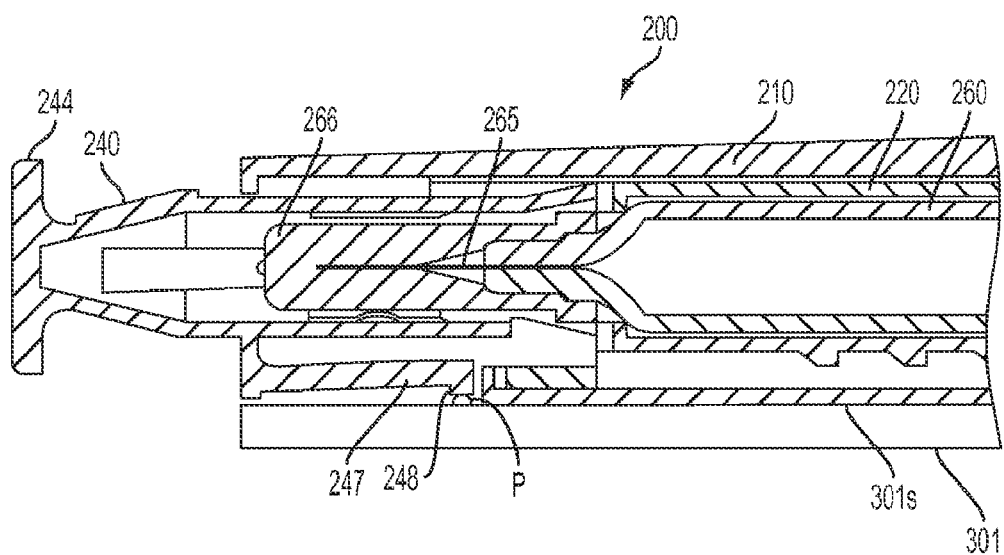
FIG. 15D is a sectional side view of the proximal portion of the cassette installed in the autoinjector showing the operation of a cantilever lock arm of the cassette cap.

FIG. 15D shows the cassette 200 after the access door of the autoinjector (both not visible) has been closed. As shown, the cassette 200 is mounted on the support surface 301s of the autoinjector chassis 301. The chassis 301 may include a pin switch P, which is coupled to the microprocessor of the autoinjector in a manner that allows signals or data to be communicated to the microprocessor. Closure of the autoinjector cassette door may cause the pin switch P to press on the lock tab 248 (if certain conditions regarding the cassette are met as will be explained further on), thereby bending the cantilever spring member 247 up, and releasing it from the lock tab 248 from the lock tab receiving aperture 210a (FIG. 15C) in the bottom wall 210B of the outer cassette housing 210, thereby unlocking the cassette cap 240 from the cassette 200. With the locking tab 248 unlocked, a user can now grasp the gripping member 244 of the cassette cap 240 and withdraw it from the cassette 200 and the autoinjector, thereby removing the needle shield 266 and uncovering the injection needle 265. When the pin switch P engages the lock tab 248, it may also signal the autoinjector's microprocessor so that the autoinjector knows that the cassette 200 has been installed.

Figure 17A:
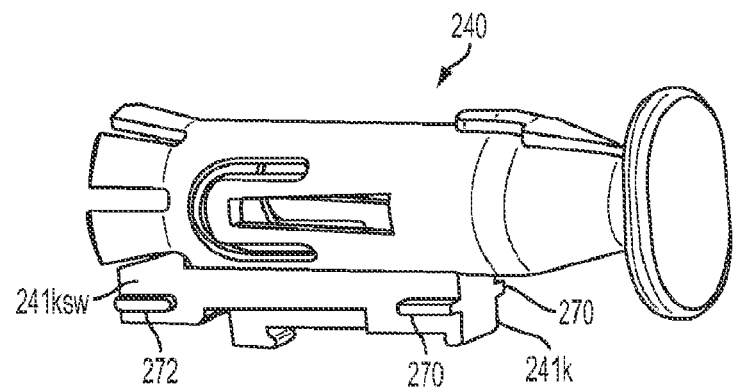
FIG. 17A is a top down front perspective view of another embodiment of the cassette cap having a key portion comprising first and second pairs of tabs.
Figure 17B:
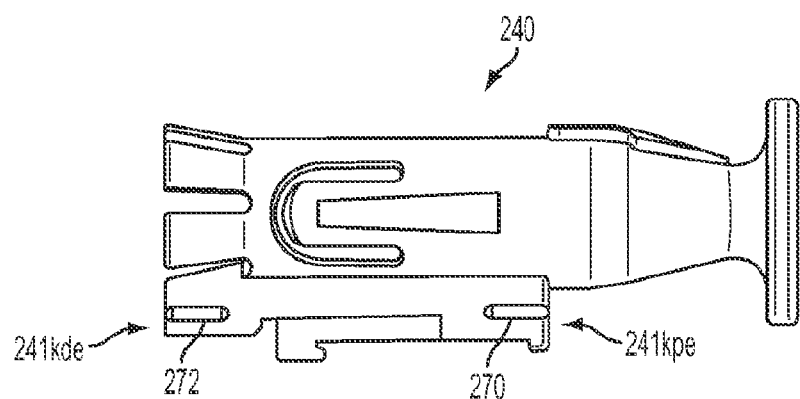
FIG. 17B is a side view of the cassette cap of FIG. 17A.

As shown in FIG. 17A, various embodiments of the key 241k may further include first and second pairs of arms or tabs 270 and 272, respectively extending out from the exterior side wall surfaces 241ksw of the key 241k. As shown in FIG. 17B, the first pair of arms 270 may be disposed at or near the proximal end 241kpe of the key 241 and the second pair of arms may be disposed at or near the distal end of the key 241kde. The arms on each side of the key 241k may be arranged in an inline manner, as shown in FIG. 17B.

Figure 18A:
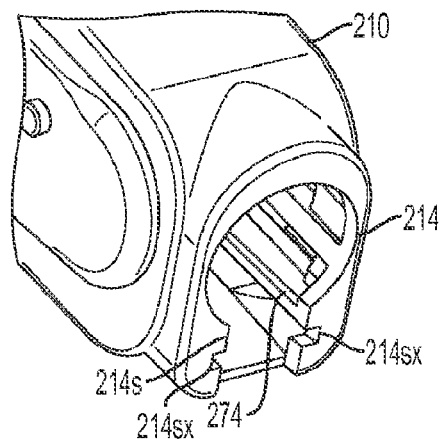
FIG. 18A is a top down front perspective view of a proximal portion of the outer housing of the cassette with the cassette cap removed, showing another embodiment of a slot for receiving the tabs of the key portion of the cassette cap embodied in FIG. 17A and ribs disposed in the outer housing for engaging the tabs provided on the key portion of the cassette cap of FIG. 17A.
Figure 18B:
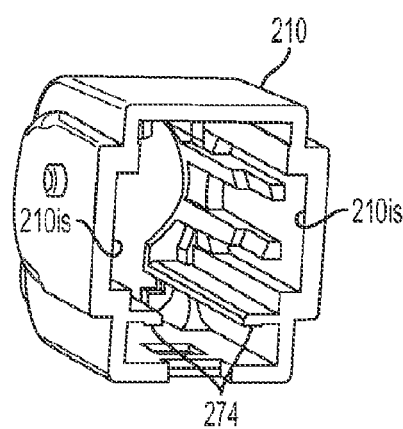
FIG. 18B is a top down rear perspective view of a proximal portion of the cassette outer housing showing the interior thereof and the ribs.

Referring collectively to FIGS. 18A and 18B, various embodiments of the cassette outer housing 210 may comprise a pair of ribs 274 provided on the interior side wall surfaces 210is thereof. As shown in FIG. 18B, the key receiving slot 214s formed in the proximal end wall 210pe of the outer housing 210 may include slot extensions 214sx that allow the first and second pairs of tabs 270 and 272, respectively to pass through the proximal end wall 210pe of the cassette outer housing 210 when the cassette cap 240 is removed from the cassette 200. The slot extensions 214sx may be disposed immediately below the ribs 274 so that the tabs 270, 272 engage the ribs 272, as will be explained below in further detail.

Figure 19A:
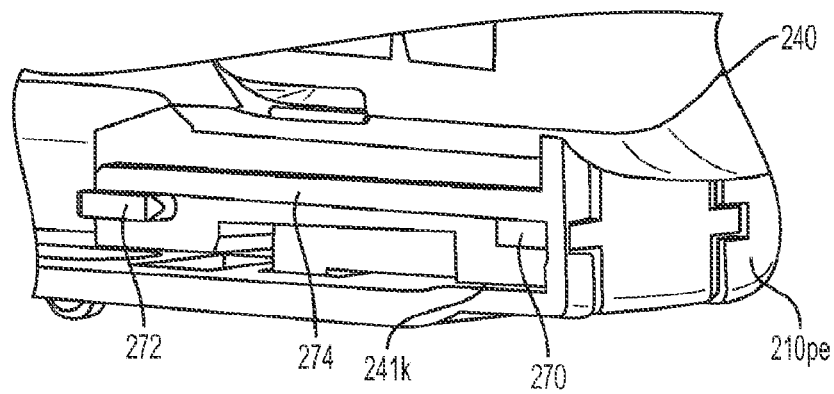
FIG. 19A is a front perspective view of an interior portion of the cassette with the cassette cap installed, which shows the tabs on one side of the cassette cap key portion engaged with one of the ribs in the cassette outer housing.
Figure 19B:
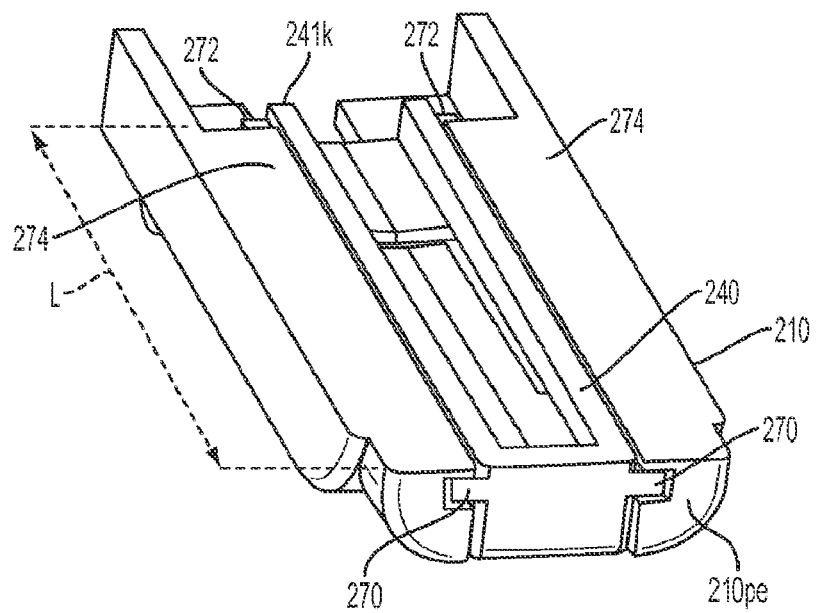
FIG. 19B is a sectional bottom view of a proximal portion of the cassette outer housing with the cassette cap installed, which shows the tabs on the cassette cap key portion engaged with the ribs in the cassette outer housing.

As shown collectively in FIGS. 19A and 19B, the ribs 274 may extend longitudinally from the proximal end wall 210pe of the cassette outer housing 210 and have a length L which allows the ribs to engage both pairs of tabs 270, 272 when the cassette cap 240 is disposed in the cassette outer housing 200. As shown in FIG. 19A, the upper surfaces of the key tabs 270, 272 may engage the lower surfaces of the outer housing ribs 274 when the cassette key 241k is disposed in the cassette outer housing 210, thereby forming a cassette cap anti-bending structure. In other embodiments, the key tabs 270, 272 and ribs 267 may also be constructed so that the lower surfaces of the key tabs 270, 272 engage the upper surfaces of the outer housing ribs 274.

Figure 20:
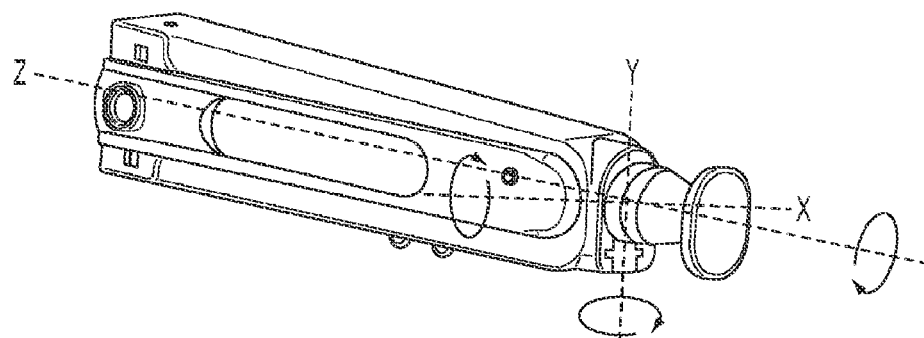
FIG. 20 is a top down front perspective view of the cassette showing how an anti-bending structure formed by the key tabs of the cassette cap and the ribs of the cassette outer housing prevent flexing or bending of the cassette cap in the vertical axis (X-axis) and horizontal axis (Y-Axis.).

As shown in FIG. 20, the anti-bending structure prevents the cassette cap 240 from being flexed or bent in the vertical axis (X-axis) and horizontal axis (Y-Axis.). The flexing or bending in the vertical or horizontal axis may bend or damage the injection needle of the drug container, therefore, the anti-bending structure prevents such bending of or damage to the injection needle.

Figure 21:
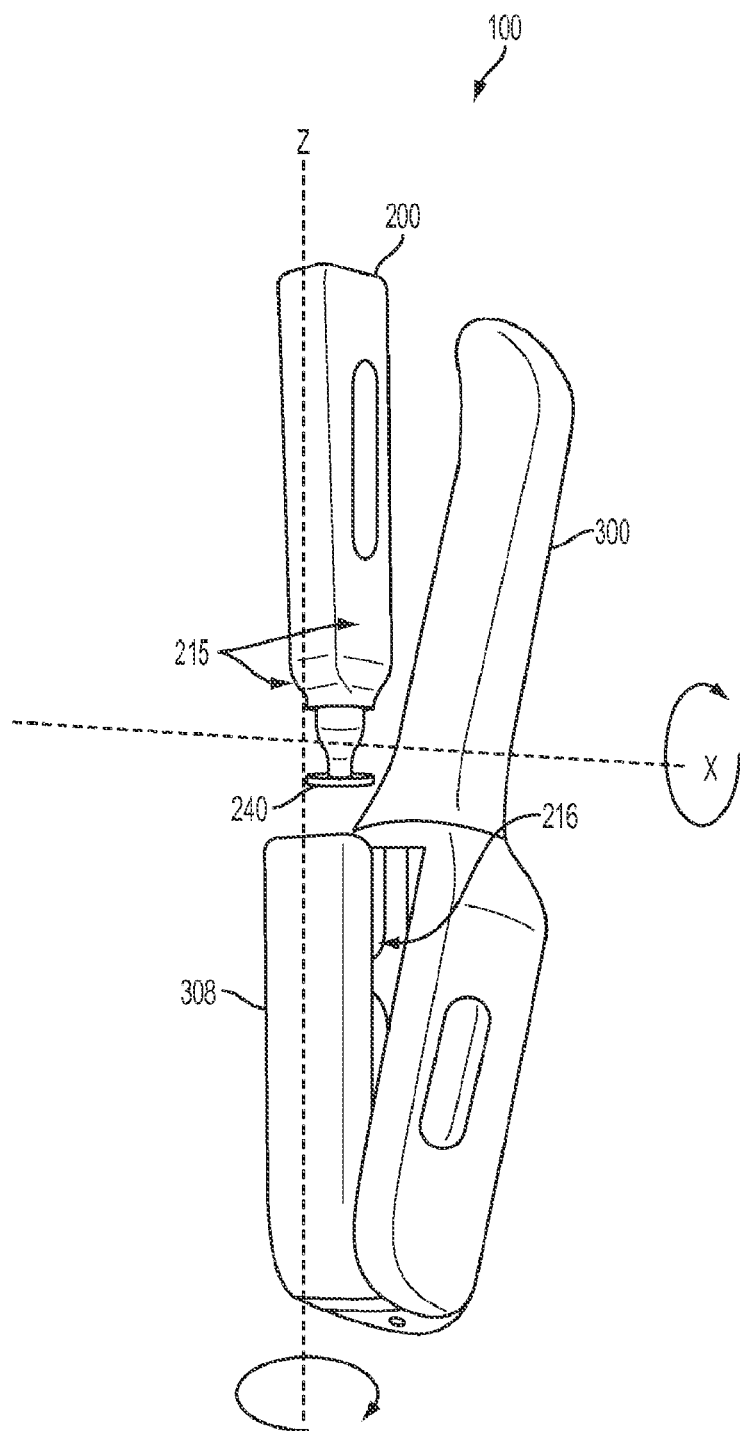
FIG. 21 is a bottom up perspective view of the autoinjector of the autoinjector apparatus or system showing the installation of a cassette into the autoinjector.

Referring now to FIG. 21, the autoinjector system 100 may be constructed to force users to execute the steps of the injection process in a safe and reliable order, which simplifies the operation of the autoinjector system 100. By controlling the sequence of actions performed by the user, the injection process can be made more reliable. Accordingly, in various embodiments, the autoinjector system 100 is constructed to force or cause the user to perform the following steps in sequence: inserting the cassette 200 into the autoinjector 300; preparing the autoinjector system 100 for injection; placing the autoinjector 300 on skin and starting the injection process; and disposing of the used cassette 200 and storing the autoinjector 300 for future use. Performing these steps in sequence ensures autoinjector system reliability and user safety.

As described above, various embodiments of the autoinjector 300 and cassette 200 can comprise mechanical, electromechanical, and other structures that provide feedback signals to the microprocessor (not shown) of the autoinjector 300. The microprocessor may be programmed with instructions (e.g., algorithm), which when executed thereby, allow these signals to be evaluated by the microprocessor in order to enable the autoinjector 300 to move through discrete logic "states" where the autoinjector system 100 is in a known configuration.

Figure 22:
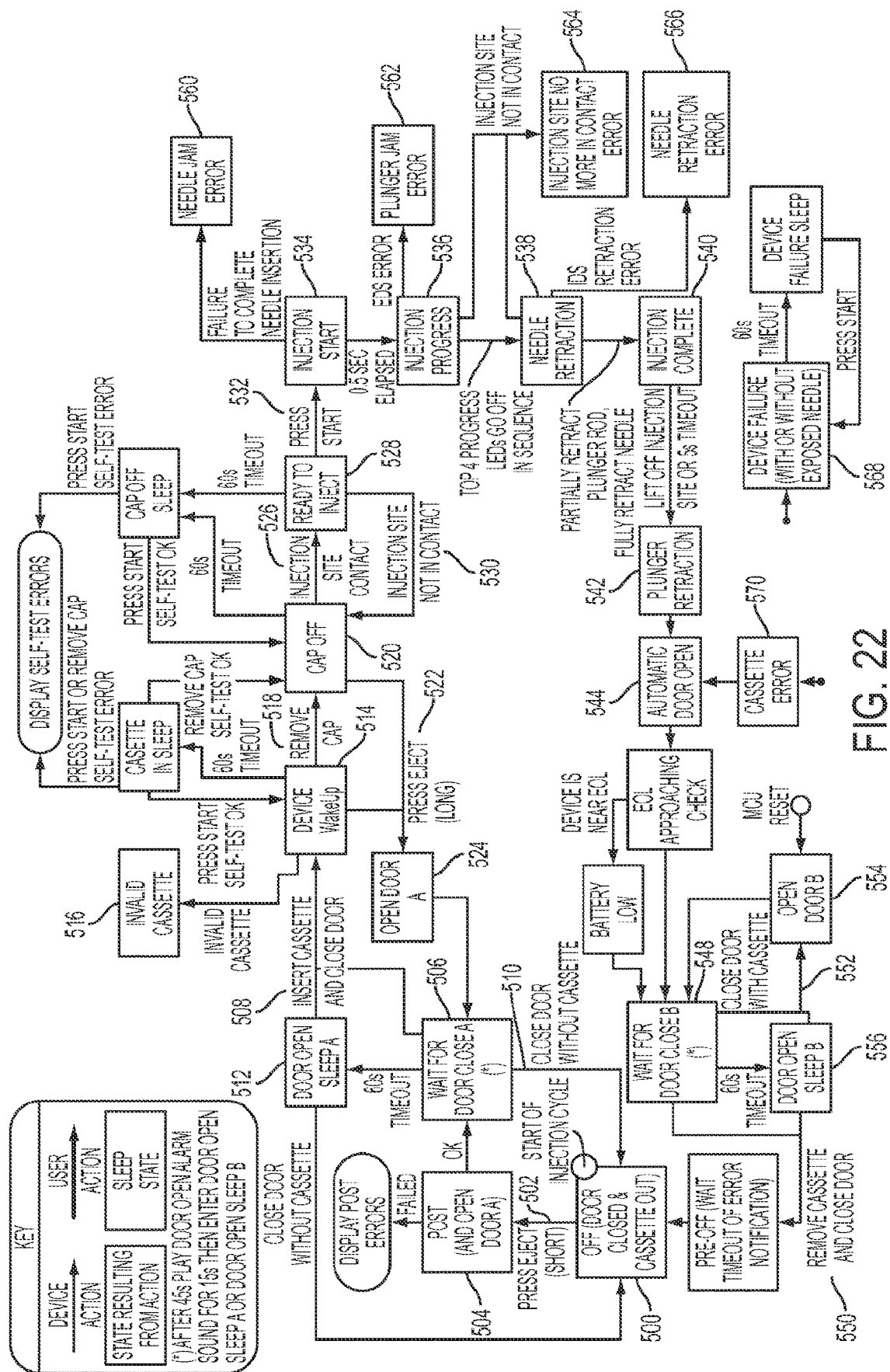
FIG. 22 is a flow chart showing an embodiment of the decision logic for forcing a user to execute the steps of an injection process in a safe and reliable order.

Referring now to FIG. 21 in conjunction with the flow chart of FIG. 22, an embodiment of the decision logic for controlling the various functions of the autoinjector system 100, will be described. The decision logic forces the user to perform, in sequence, the steps of: inserting the cassette 200 into the autoinjector 300; preparing the autoinjector system 100 for injection; placing the autoinjector 300 on skin and starting the injection process; and disposing of the used cassette 200 and storing the autoinjector 300 for future use.

Insertion of the Cassette into the Autoinjector

In block 500 (Off, Door Close, Cassette Out), prior to use, the autoinjector system 100 may be in a state where the only button that is active is the one to initiate cassette door opening (eject button) and all other buttons are deactivated. This may force the autoinjector system 100 only to respond to a single user action of pressing the eject button at arrow 502 and all other actions may be ignored or may not be possible. Once the cassette door 308 of the autoinjector 300 opens in block 504, the user may insert the cassette 200 into the door. In various embodiments, the autoinjector 300 and cassette 200 may comprise certain structures that allow the insertion of the cassette 200 only in the correct orientation, such as one or more pins 215 on the cassette 200, which interacts with a corresponding slot or pin 216 in the cassette door 308 of the autoinjector 300, as shown in FIG. 22, to allow insertion only in the correct orientation and prevent insertion in orientations about the insertion axis (z axis). The cassette 200 may also have a tapered shape or other structure, which matches with the cassette door 308 of the autoinjector 300 to prevent rotation about the x axis.

While waiting for the user to insert the cassette 200, the autoinjector 300 may transition to a known state in block 506 (Wait for Door Close A) where all other actions from the user with the exception of closing the door may be ignored such as pressing of start and eject buttons, etc.

This may force the user to either close the cassette door 308 with a cassette 200 at arrow 508 to proceed with the injection process, or close the door at arrow 510 without a cassette 200 as the autoinjector system 100 moves to the previous known state of block 500. If the user chooses not to perform the required action, the autoinjector system 100 continues to remain in the same state in block 512 (Door Open).

If the user inserts a cassette 200 of either an unknown configuration and/or a used cassette 200 into the cassette door 308 and closes at arrow 508, the autoinjector system 100 detects this state using, for example the cassette identification arrangement described earlier, and does not allow the process to continue to the next state in block 516. Accordingly, the user is forced to insert a valid cassette 200 (known configuration and unused) in the correct orientation into the autoinjector 300 in order to proceed.

Preparing the Autoinjector System for Injection

Once the cassette door 308 of the autoinjector 300 has been closed with a valid cassette 200, the autoinjector system 100 may move to an active state in block 514 (Device Wakeup). The next step by the user in this configuration is to remove the cassette cap 240 at arrow 518. As described above, the autoinjector system 100, in various embodiments, may be capable of detecting the presence or absence of the cassette cap 240, and may also capable of monitoring a transition in the state of a cassette cap remover switch that may be provided in the autoinjector 300 from presence to absence. This transition may be used by the autoinjector system 100 to detect the removal of the cassette cap 240 by the user and moving the autoinjector system 100 to the state of block 520 (Cap Off). This may force the user to either remove the cassette cap 240 at arrow 518 to proceed with the injection process, or abort the process by pressing the eject button at arrow 522, which opens the door at block 524 (Open Door A) to allow the cassette 200 to be removed and returns the autoinjector system 100 to the last known state at block 506 (Wait for Door Close A). If the user chooses not to perform the required actions, the autoinjector system 100 continues to remains in the same state at block 515 (Cassette in Sleep).

To ensure that these actions are truly intended by the user and not accidentally initiated, the cassette cap removal and abort process may require a committed action. Cassette cap removal may have a minimum pull off force and pull off direction such that a user or patient needs to purposefully hold and pull off the cassette cap in order to remove the needle shield. In other words, there is minimum removal force and direction for removal (pulling straight down) such that the cassette cap cannot be accidentally removed by normal handling. For the abort process, this may be achieved by requiring the user to press and hold the eject button for a set time period at arrow 522 before the eject process is initiated.

Place on Skin and Start the Injection Process

With a valid cassette 200 inserted into the autoinjector 300, the cassette cap 240 removed, and the autoinjector system 100 in the state of block 520 (Cap Off), the user may place the autoinjector 300 on the injection site (skin) at arrow 526. As described above, various embodiments of the autoinjector 300 may include a skin sensor to allow the autoinjector system 100 to detect proximity to the injection site. Therefore, the autoinjector system 100 can allow the user to proceed with the injection process only when the injection site is detected. As described above, the microprocessor may be programmed with instructions, which allow the injection site presence to be indicated only when it detects a continuous positive signal from the skin sensor. This ensures that the user is committed to the process and has a stable contact with the injection site in order to move to the state of block 534 (Ready to Inject). As described above, various embodiments of the cassette cap 240 may have a structure that does not allow it to be reinserted into the cassette 200 once removed, thereby preventing the user from reinserting the cassette cap 240 and moving back to the prior state of block 514 (Device Wakeup).

This forces the user to either hold the autoinjector 300 with a stable contact at the injection site in order to proceed with the injection process at block 534 or abort the process by pressing the eject button at arrow 522, which opens the door at block 524 to allow cassette removal and returns the autoinjector system 100 to the last known state after door opening at block 506 (Wait for Door Close A). If no stable signal is obtained at arrow 530, the autoinjector system 100 may continue to remain in the state of block 520 (Cap Off). If injection site contact is lost at any point in time, the autoinjector system 100 may return to the state of block 520 (Cap Off).

Once the above conditions are met and the autoinjector system 100 is in the state of block 526 (Ready to Inject), the user in this configuration activates the injection at arrow 532. Once initiated, the autoinjector system 100 may reconfirm the cassette identification arrangement, skin sensor and the like, to confirm its expected configuration and once confirmed, it may automatically execute in sequence, needle injection and drug extrusion in block 536 (Injection Progress), (Needle Retraction) in block 538, (Injection Complete) in block 540, (Plunger Retraction) in block 542 and (Automatic Door Open) in block 544, to allow for cassette removal and disposal at block 548 (Wait for Door Close B). Immediately after injection initiation by the user, all other buttons and switches on the autoinjector 300 may be disabled to prevent unintentional activation of the buttons by the user during the injection process.

During the injection process, the autoinjector system 100 constantly continuously monitors the status of the injection site contact in block 564. The process may be terminated if at any point in time there is a loss in injection site contact for a predetermined time (e.g., the user intentionally removes the autoinjector 300 from the injection site or adjusts the position in such a way that a reliable delivery process cannot be ensured). In addition, autoinjector system 100 may check for various mechanical errors during the injection process in block 560 (Needle Jam Error), block 562 (Plunger Jam Error), block 566 (Needle Retraction Error), block 568 (Device Failure), and block 570 (Cassette Error).

Disposal of the Used Cassette and Storing the Autoinjector for Future Use

Once the injection process is complete and the autoinjector system 100 is in the state of block 548 (Wait for Door Close B), the user is expected to remove and disposed of the used cassette 200 and close the cassette door 308 of the autoinjector 300 at arrow 550. In order to force the user to do this, the autoinjector system 100 logic may be configured so that the user cannot close the cassette door 308 of the autoinjector 300 with a cassette 200 in the state of block 548. If door closure is attempted at arrow 552, the autoinjector system 100 may detect the cassette 200 and immediately reopen the door at block 554. This may force the user to close the cassette door 308 without a cassette 200 in order for the autoinjector system 100 to move to the state of block 550 (Off) and store the autoinjector 300 for future use. If the user chooses not to perform the required action, the autoinjector system 100 may continues to remain in the same state in block 556 (Door Open Sleep B).

The drug container of the cassette may be filled for treatment or be prefilled with a pharmaceutical product, such as an erythropoiesis stimulating agent (ESA), which may be in a liquid or a lyophilized form. An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins comprise erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins comprise, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (comprising EMP1/Hematide), and mimetic antibodies. Exemplary erythropoiesis stimulating proteins comprise erythropoietin, darbepoetin, erythropoietin agonist variants, and peptides or antibodies that bind and activate erythropoietin receptor.

The term erythropoiesis stimulating protein comprises without limitation Epogen® (epoetin alfa), Aranesp® (darbepoetin alfa), Dynepo® (epoetin delta), Mircera® (methyoxy polyethylene glycol-epoetin beta), Hematide™ (peginesatide), MRK-2578, INS-22, Retacrit® (epoetin zeta), Neorecormon® (epoetin beta), Silapo™ (epoetin zeta), Binocrit® (epoetin alfa), epoetin alfa Hexal, Abseamed™ (epoetin alfa), Ratioepo™ (epoetin theta), Eporatio™ (epoetin theta), Biopoin™ (epoetin theta), epoetin alfa, epoetin beta, epoetin zeta, epoetin theta, and epoetin delta.

The term erythropoiesis stimulating protein further comprises the molecules or variants or analogs as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,830,851; 5,856,298; 5,955,422; 5,986,047; 6,030,086; 6,310,078; 6,391,633; 6,583,272; 6,586,398; 6,900,292; 6,750,369; 7,030,226; 7,084,245; and 7,271,689; U.S. Publ. Nos. 2002/0155998; 2003/0077753; 2003/0082749; 2003/0143202; 2003/0215444; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0040858; 2006/0088906; and 2006/0111279; and PCT Publ. Nos. WO 91/05867; WO 95/05465; WO 96/40772; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076;

WO 2005/100403; WO 2005/092369; WO 2006/50959; WO 2006/02646; WO 2006/29094; and WO 2007/136752.

Alternatively, the drug container of the cassette may also be filled for treatment or be prefilled with other products. Examples of other pharmaceutical products that may be used may comprise, but are not limited to, therapeutics such as a biological (e.g., Enbrel® (etanercept, TNF-receptor/Fc fusion protein, TNF blocker), anti-TNF antibodies such as adalimumab, infliximab, certolizumab pegol, and golimumab; anti-IL-12 antibodies such as ustekinumab, other Fc fusions such as CTL4A:Fc also known as abacept; Neulasta® (pegylated filgastrim, pegylated G-CSF, pegylated hu-met-G-CSF), Neupogen® (filgrastim, G-CSF, hu-met-G-CSF), Nplate® (romiplostim), Vectibix® (panitumumab), Sensipar® (cinacalcet), and Xgeva® and Prolia® (each denosamab, AMG 162); as well as other small molecule drugs, a therapeutic antibodies, a polypeptides, proteins or other chemicals, such as an iron (e.g., ferumoxytol, iron dextrans, ferric glyconate, and iron sucrose). The therapeutic may be in liquid form, or reconstituted from lyophilized form.

Among particular illustrative proteins that can be used in the drug container of the cassette are antibodies, peptibodies, pegylated proteins, polypeptides, and related proteins (comprising fusions, fragments, analogs, variants or derivatives thereof) for example, proteins that specifically bind to: OPGL; IL-4 receptor; interleukin 1-receptor 1 ("IL1-R1"); angiopoietin-2 (Ang2); NGF; CD22; IGF-1; B-7 related protein 1 (B7RP1); IL-15; IL-17 Receptor A: IFN gamma; TALL-1; parathyroid hormone ("PTH"); thrombopoietin receptor ("TPO-R"); hepatocyte growth factor ("HGF"); TRAIL-R2; Activin A; TGF-beta; amyloid-beta; c-Kit; α4β7: and IL-23 or one of its subunits; and other therapeutic proteins.

The drug container of the cassette may also be filled for treatment or be prefilled with OPGL specific antibodies, peptibodies, and related proteins, and the like (also referred to as RANKL specific antibodies, peptibodies and the like), comprising fully humanized and human OPGL specific antibodies, particularly fully humanized monoclonal antibodies, comprising but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, comprising the OPGL specific antibodies having either the light chain of SEQ ID NO: 2 therein as set forth in FIG. 2 therein and/or the heavy chain of SEQ ID NO:4 therein, as set forth in FIG. 4 therein, each of which is individually and specifically incorporated by reference herein in its entirety fully as disclosed in the foregoing Publication.

The drug container of the cassette may also be filled for treatment or be prefilled with myostatin binding proteins, peptibodies, and related proteins, and the like, comprising myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, comprising but not limited to peptibodies of the mTN8-19 family, comprising those of SEQ ID NOS: 305-351, comprising TN8-19-1 through TN8-19-40, TN8-19 con1 and TN8-19 con2; peptibodies of the mL2 family of SEQ ID NOS: 357-383 therein; the mL15 family of SEQ ID NOS: 384-409; the mL17 family of SEQ ID NOS: 410-438 therein; the mL20 family of SEQ ID NOS: 439-446 therein; the mL21 family of SEQ ID NOS: 447-452 therein; the mL24 family of SEQ ID NOS: 453-454 therein; and those of SEQ ID NOS: 615-631 therein, each of which is individually and specifically incorporated by reference herein in their entirety fully as disclosed in the foregoing publication.

The drug container of the cassette may also be filled for treatment or be prefilled with IL-4 receptor specific antibodies, peptibodies, and related proteins, and the like, particularly those that inhibit activities mediated by binding of IL-4 and/or IL-13 to the receptor, comprising those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; LIH8; L1H9; LIHIO; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

The drug container of the cassette may also be filled for treatment or be prefilled with IL1-R1 specific antibodies, peptibodies, and related proteins, and the like, comprising but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication.

The drug container of the cassette may also be filled for treatment or be prefilled with Ang2 specific antibodies, peptibodies, and related proteins, and the like, comprising but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and comprising but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also comprising anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication.

The drug container of the cassette may also be filled for treatment or be prefilled with NGF specific antibodies, peptibodies, and related proteins, and the like comprising, in particular, but not limited to those described in US Publ. No. 2005/0074821 and U.S. Pat. No. 6,919,426, which are incorporated herein by reference in their entirety particularly as to NGF-specific antibodies and related proteins in this regard, comprising in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

The drug container of the cassette may also be filled for treatment or be prefilled with CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, comprising but not limited to humanized and fully human monoclonal antibodies, particularly comprising but not limited to human CD22 specific IgG antibodies, such as, for instance, a dimer of a human-mouse monoclonal hLL2 gamma-chain disulfide linked to a human-mouse monoclonal hLL2 kappa-chain, comprising, but limited to, for example, the human CD22 specific fully humanized antibody in Epratuzumab, CAS registry number 501423-23-0;

The drug container of the cassette may also be filled for treatment or be prefilled with IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, comprising but not limited to the TGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication.

Also among non-limiting examples of anti-IGF-1R antibodies for use in the methods and compositions of the present invention are each and all of those described in: (i) US Publ. No. 2006/0040358 (published Feb. 23, 2006), 2005/0008642 (published Jan. 13, 2005), 2004/0228859 (published Nov. 18, 2004), comprising but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; (ii) PCT Publ. No. WO 06/138729 (published Dec. 28, 2006) and WO 05/016970 (published Feb. 24, 2005), and Lu et al., 2004, J Biol. Chem. 279:2856-65, comprising but not limited to antibodies 2F8, A12, and IMC-A12 as described therein; (iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003); (iv) US Publ. No. 2005/0084906 (published Apr. 21, 2005), comprising but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; (v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, comprising but not limited to antibody EM164, resurfaced EM164, humanized EM164, huEM164 v1.0, huEM164 v1.1, huEM164 v1.2, and huEM164 v1.3 as described therein; (vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, comprising but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; (vii) US Publ. Nos. 2005/0136063 (published Jun. 23, 2005) and 2004/0018191 (published Jan. 29, 2004), comprising but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), comprising but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

The drug container of the cassette may also be filled for treatment or be prefilled with B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, comprising but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication.

The drug container of the cassette may also be filled for treatment or be prefilled with IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, comprising peptibodies, comprising particularly, for instance, but not limited to, HuMax IL-15 antibodies and related proteins, such as, for instance, 146B7.

The drug container of the cassette may also be filled for treatment or be prefilled with pharmaceutical compositions comprising antagonistic human monoclonal antibodies against human IL-17 Receptor A. The characterization, cloning, and preparation of IL-17 Receptor A are described in U.S. Pat. No. 6,072,033, issued Jun. 6, 2000, which is incorporated herein by reference in its entirety. The amino acid sequence of the human IL-17RA is shown in SEQ ID NO:10 of U.S. Pat. No. 6,072,033 (GenBank accession number NM 014339). Such antibodies may comprise those disclosed in WO 2008/054603, which is incorporated by reference in its entirety or the antibodies claimed in U.S. Pat. No. 7,767,206, issued Aug. 3, 2010, and in U.S. Ser. No. 11/906,094, which are incorporated by reference in their entirety.

The drug container of the cassette may also be filled for treatment or be prefilled with IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies comprise those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ TD NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein.

The drug container of the cassette may also be filled for treatment or be prefilled with TALL-1 specific antibodies, peptibodies, and related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B therein, each of which is individually and specifically incorporated by reference herein in its entirety fully as disclosed in the foregoing US Publications.

The drug container of the cassette may also be filled for treatment or be prefilled with PTH specific antibodies, peptibodies, and related proteins, and the like, such as those described in U.S. Pat. No. 6,756,480, which is incorporated herein by reference in its entirety, particularly in parts pertinent to proteins that bind PTH.

The drug container of the cassette may also be filled for treatment or be prefilled with TPO-R specific antibodies, peptibodies, and related proteins, and the like, such as those described in U.S. Pat. No. 6,835,809, which is herein incorporated by reference in its entirety, particularly in parts pertinent to proteins that bind TPO-R.

The drug container of the cassette may also be filled for treatment or be prefilled with HGF specific antibodies, peptibodies, and related proteins, and the like, comprising those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF.

The drug container of the cassette may also be filled for treatment or be prefilled with TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2.

The drug container of the cassette may also be filled for treatment or be prefilled with Activin A specific antibodies, peptibodies, related proteins, and the like, comprising but not limited to those described in US Publ. No. 2009/0234106, which is herein incorporated by reference in its entirety, particularly in parts pertinent to proteins that bind Activin A.

The drug container of the cassette may also be filled for treatment or be prefilled with TGF-beta specific antibodies, peptibodies, related proteins, and the like, comprising but not limited to those described in U.S. Pat. No. 6,803,453 and US Publ. No. 2007/0110747, each of which is herein incorporated by reference in its entirety, particularly in parts pertinent to proteins that bind TGF-beta.

The drug container of the cassette may also be filled for treatment or be prefilled with amyloid-beta protein specific antibodies, peptibodies, related proteins, and the like, comprising but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication.

The drug container of the cassette may also be filled for treatment or be prefilled with c-Kit specific antibodies, peptibodies, related proteins, and the like, comprising but not limited to those described in Publ. No. 2007/0253951, which is incorporated herein by reference in its entirety, particularly in parts pertinent to proteins that bind c-Kit and/or other stem cell factor receptors.

The drug container of the cassette may also be filled for treatment or be prefilled with OX40L specific antibodies, peptibodies, related proteins, and the like, comprising but not limited to those described in U.S. application Ser. No. 11/068,289, which is incorporated herein by reference in its entirety, particularly in parts pertinent to proteins that bind OX40L and/or other ligands of the OXO40 receptor.

The drug container of the cassette may also be filled for treatment or be prefilled with other exemplary proteins comprising but are not limited to Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (ctancrcept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP 1lIb/IIia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-B. anthracis Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab), BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2; a sclerostin antibody, such as but not limited to romosozumab, blosozumab, or BPS 804 (Novartis). Also included can be therapeutics such as rilotumumab, bixalomer, trebananib, ganitumab, conatumumab, motesanib diphosphate, brodalumab, vidupiprant, panitumumab, denosumab, romosozumab NPLATE, PROLIA, VECTIBIX or XGEVA. Additionally, included in the AI can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

The drug container of the cassette may also be filled for treatment or be prefilled with antibodies comprising, but not limited to, those that recognize any one or a combination of proteins comprising, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

Additional examples of known antibodies that may be contained in the drug container of the cassette can comprise but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtomomab, pertuzumab, ranibizumab, rituximab, rovelizumab, tocilizumab, tositumomab, trastuzumab, ustekinumab, zalutumumab, and zanolimumab.

Although the autoinjector system, cassette, and autoinjector, have been described in terms of exemplary embodiments, it is not limited thereto. Rather, the appended claims should be construed broadly, to comprise other variants and embodiments of same, which may be made by those skilled in the art without departing from the scope and range of equivalents of the autoinjector system, cassette, and autoinjector and their elements.

What is claimed is:

1. A cassette for an injector, the cassette comprising:
   a housing;
   a sleeve movably disposed within the housing, the sleeve for directly or indirectly holding a drug container;
   a locking arrangement for interlocking the sleeve with the housing, the locking arrangement comprising:
     a spring-biased member associated with one of the housing and the sleeve,
     a fixed member associated with the other one of the housing and the sleeve, wherein the fixed member defines an opening and the spring-biased member comprises a locking foot biased for interlocking with the opening of the fixed member in a locked position, and
     a cam of the spring-biased member for unlocking the spring-biased and fixed members.

2. The cassette according to claim 1, wherein the locking foot comprises a pair of spaced locking feet and the opening comprises a pair of openings, the pair of spaced locking feet each engaging one of the pair of openings in a locked position, to interlock the sleeve with the housing.

3. The cassette according to claim 1, wherein the locking foot is disposed on a hand member.

4. The cassette according to claim 3, wherein the hand member is connected to the one of the housing and the sleeve by at least one flexible arm member, the at least one flexible arm member biasing the hand member.

5. The cassette according to claim 4, wherein the at least one flexible arm member biases the hand member in an unlocked position where the locking foot is disengaged from the opening.

6. The cassette according to claim 4, wherein the at least one flexible arm member biases the hand member in the locked position where the locking foot is engaged with the opening.

7. The cassette according to claim 4, wherein the cam is disposed on the hand member.

8. The cassette according to claim 1, wherein the cam is configured to be actuated by the injector during a needle-insertion cycle of the injector.

9. The cassette according to claim 1, wherein the opening comprises a first angled surface; and the locking foot has a second angled surface configured to engage the first angled surface if the locking foot is engaged with the opening, to facilitate self-locking or self-unlocking thereof, depending upon the angle of the first and second angled surfaces.

10. The cassette according to claim 1, wherein the cam prevents the spring-biased member from interfering with the assembly of the sleeve to the housing.

11. The cassette according to claim 10, wherein the spring-biased member comprises a hand member having the locking foot disposed thereon; and the cam is disposed on the hand member.

12. The cassette according to claim 11, wherein the cam extends forward of a leading edge of the hand member.

13. The cassette according to claim 1, further comprising a latch mechanism comprising a first member associated with the housing and a second member associated with the sleeve.

14. The cassette according to claim 1, further comprising a cassette identification arrangement (cassette ID) defining a code containing information about the cassette, the code being detectable and decipherable by the injector, the cassette ID disposed on the housing, embedded within the housing, provided on or in a separate structure contained within the housing, or any combination thereof.

15. The cassette according to claim 1, wherein the housing includes an aperture; and further comprising:
   the drug container disposed in the sleeve, the drug container having an injection needle and a needle shield disposed over the injection needle;
   a cassette cap for removing the needle shield, the cassette cap comprising a generally cylindrical body portion and a key portion disposed adjacent to the cylindrical body portion, the cylindrical body portion engaging the needle shield, the cylindrical body portion having a portion extending through the aperture in the housing configured to be gripped to withdraw the cassette cap from the housing to remove the needle shield; and
   an anti-bending structure for preventing bending or flexing of the cassette cap, the anti-bending structure having at least a first member associated with the key portion and at least a second member associated with the housing for interacting with the first member.

16. The cassette according to claim 1, wherein the sleeve contains the drug container filled for treatment or prefilled with a drug.

17. The cassette according to claim 16, wherein the drug comprises a therapeutic product.

18. The cassette according to claim 17, wherein the therapeutic product is selected from the group consisting of epoetin alfa, darbepoetin alfa, etanercept, pegylated filgastrim, filgrastim, romiplostim, panitumumab, cinacalcet, and denosamab.

19. The cassette according to claim 17, wherein the therapeutic product is one of (a) an antibody to IL-17 Receptor A, (b) an antagonist of angiopoietin-2, or (c) a TNF blocker or inhibitor.

20. The cassette according to claim 19, wherein the therapeutic product is a TNF blocker or inhibitor and the TNF blocker or inhibitor is etanercept, adalimumab, certolizumab, golimumab, or infliximab.

21. The cassette according to claim 17, wherein the therapeutic product has (a) a viscosity of about 19 centipoise at room temperature, (b) a viscosity ranging between about 1 centipoise and about 320 centipoise, at room temperature, (c) a viscosity ranging between about 5 centipoise and about 40 centipoise, at room temperature, (d) a viscosity ranging between about 10 centipoise and about 35 centipoise, at room temperature, (e) a viscosity ranging between about 15 centipoise and about 30 centipoise, at room temperature, (f) a viscosity ranging between about 20 centipoise and about 25 centipoise, at room temperature, (g) a viscosity ranging between about 16 centipoise and about 42 centipoise, at room temperature, or (h) a viscosity ranging between about 1 centipoise and about 29 centipoise, at room temperature.

\* \* \* \* \*